US011554178B2

(12) United States Patent
Berlin et al.

(10) Patent No.: US 11,554,178 B2
(45) Date of Patent: Jan. 17, 2023

(54) COMPOSITIONS AND METHODS OF MODULATING MACROPHAGE ACTIVITY

(71) Applicant: CITY OF HOPE, Duarte, CA (US)

(72) Inventors: Jacob Berlin, Monrovia, CA (US); Tom Haber, Pasadena, CA (US); Yvonne Cornejo, Ontario, CA (US)

(73) Assignee: CITY OF HOPE, Duarte, CA (US)

( * ) Notice: Subject to any disclaimer, the term of this patent is extended or adjusted under 35 U.S.C. 154(b) by 279 days.

(21) Appl. No.: 16/625,099

(22) PCT Filed: Jun. 29, 2018

(86) PCT No.: PCT/US2018/040405
§ 371 (c)(1),
(2) Date: Dec. 20, 2019

(87) PCT Pub. No.: WO2019/006371
PCT Pub. Date: Jan. 3, 2019

(65) Prior Publication Data
US 2020/0222557 A1 Jul. 16, 2020

Related U.S. Application Data

(60) Provisional application No. 62/527,531, filed on Jun. 30, 2017.

(51) Int. Cl.
A61K 47/69 (2017.01)
A61K 47/54 (2017.01)
(Continued)

(52) U.S. Cl.
CPC ........ A61K 47/6923 (2017.08); A61K 9/0019 (2013.01); A61K 9/51 (2013.01);
(Continued)

(58) Field of Classification Search
CPC .................................................. A61K 47/6923
See application file for complete search history.

(56) References Cited

U.S. PATENT DOCUMENTS 4,861,760 A 8/1989 Mazuel et al.
4,911,920 A 3/1990 Jani et al.
(Continued)

FOREIGN PATENT DOCUMENTS

WO WO-2015/077657 A2 5/2015
WO WO-2017/004357 A1 1/2017

OTHER PUBLICATIONS

Hee-Kyung Na et al. "Efficient Functional Delivery of siRNA using Mesoporous Silica Nanoparticles with Ultralarge Pores." Small, vol. 8 No. 11, 2012, pp. 1752-1761. (Year: 2012).*
(Continued)

*Primary Examiner* — Isaac Shomer
(74) *Attorney, Agent, or Firm* — Irina E. Britva; Mintz, Levin, Cohn, Ferris, Glovsky and Popeo, P.C.

(57) ABSTRACT

Disclosed herein, inter alia, are compositions and methods of modulating macrophage activity. Provided is a method of treating a disease (e.g., a macrophage-associated disease, autoimmune disease, inflammatory disease, or a cancer of an organ in the intraperitoneal cavity), the method including intraperitoneally administering to a subject in need thereof a therapeutically effective amount of a nanoparticle composition or pharmaceutical composition. Provided is a silica nanoparticle non-covalently bound to a plurality of nucleic acids, wherein the silica nanoparticle has a net positive charge in the absence of the plurality of nucleic acids. Provided is a pharmaceutical composition including a nanoparticle composition as described herein, and a pharmaceutically acceptable excipient.

8 Claims, 27 Drawing Sheets

Specification includes a Sequence Listing.

(51) Int. Cl.
| | |
|---|---|
| A61K 9/00 | (2006.01) |
| A61K 9/51 | (2006.01) |
| A61K 31/542 | (2006.01) |
| A61K 38/19 | (2006.01) |
| A61K 38/21 | (2006.01) |
| C12N 15/113 | (2010.01) |

(52) U.S. Cl.
CPC .......... *A61K 9/5115* (2013.01); *A61K 9/5153* (2013.01); *A61K 31/542* (2013.01); *A61K 38/191* (2013.01); *A61K 38/193* (2013.01); *A61K 38/21* (2013.01); *A61K 47/549* (2017.08); *C12N 15/113* (2013.01)

(56) References Cited

U.S. PATENT DOCUMENTS

| | | | |
|---|---|---|---|
| 5,034,506 | A | 7/1991 | Summerton et al. |
| 5,212,162 | A | 5/1993 | Missel et al. |
| 5,235,033 | A | 8/1993 | Summerton et al. |
| 5,403,841 | A | 4/1995 | Lang et al. |
| 2010/0055189 | A1* | 3/2010 | Hubbell .................. B82Y 5/00 424/489 |
| 2010/0104632 | A1* | 4/2010 | Ishii ................... A61K 31/7088 424/450 |
| 2010/0160368 | A1* | 6/2010 | Gregory .................. A61P 15/00 514/293 |
| 2010/0196462 | A1* | 8/2010 | Bardot .................... A61P 31/16 424/451 |
| 2011/0104293 | A1* | 5/2011 | Pulendran ............... A61K 39/12 424/490 |
| 2012/0207795 | A1 | 8/2012 | Zink et al. |
| 2013/0344003 | A1 | 12/2013 | Daldrup-Link |
| 2014/0127287 | A1* | 5/2014 | Xiong .................. A61K 9/1277 514/183 |
| 2014/0242108 | A1* | 8/2014 | Lioux .................... A61K 31/52 424/194.1 |
| 2015/0064282 | A1* | 3/2015 | Josefowitz ........... A61K 31/196 560/126 |
| 2015/0118318 | A1 | 4/2015 | Fahmy et al. |
| 2018/0161318 | A1* | 6/2018 | Kim ........................ A23L 33/10 |
| 2018/0296850 | A1* | 10/2018 | Wang ................. A61K 41/0052 |
| 2018/0318409 | A1* | 11/2018 | Valiante ............... A61K 9/5123 |
| 2018/0346417 | A1* | 12/2018 | Jung ...................... C07C 323/52 |
| 2021/0046156 | A1* | 2/2021 | Stephan ............. A61K 38/1709 |
| 2022/0047512 | A1* | 2/2022 | Sigalov .................. A61K 47/64 |

OTHER PUBLICATIONS

Francesca Brugnolo et al. "The novel synthetic immune response modifier R-848 (Resiquimod) shifts human allergen-specific CD4+ TH2 lymphocytes into IFN-γ-producing cells." Journal of Allergy and Clinical Immunology, vol. 111, No. 2, Feb. 2003, pp. 380-388. (Year: 2003).*

Fang Ma, Jianhua Zhang, Jian Zhang and Cai Zhang. "The TLR7 agonists imiquimod and gardiquimod improve DC-based immunotherapy for melanoma in mice." Cellular and Molecular Immunology, vol. 7, 2010, pp. 381-388. (Year: 2010).*

Creative Biolabs. "Conventional Liposome Development Service." https://www.creative-biolabs.com/lipid-based-delivery/conventional-liposome-development-service.htm accessed Jan. 25, 2022, pp. 1-5. (Year: 2022).*

Saijie Zhu, Mengmeng Niu, Hannah O'Mary, and Zhengrong Cui. "Targeting of Tumor-Associated Macrophages Made Possible by PEG-Sheddable, Mannose-Modified Nanoparticles." Molecular Pharmaceutics, vol. 10, 2013, pp. 3525-3530. (Year: 2013).*

Rae Sung Chang et al. "Reduced dose-limiting toxicity of intraperitoneal mitoxantrone chemotherapy using cardiolipin-based anionic liposomes." Nanomedicine: Nanotechnology, Biology, and Medicine, vol. 6 (2010), pp. 769-776. (Year: 2010).*

Gere S. diZerega, Kathleen E. Rodgers. "The Peritoneum." Springer-Verlag, ISBN 0-387-97830-5, 1992, pp. i-xi and 1-378. (Year: 1992).*

CAS Registry record for CAS Nos. 99011-02-6, 144875-48-9, and 196618-13-0, accessed on Apr. 28, 2022, 11 printed pages. (Year: 2022).*

John L. Chollet et al. "Development of a Topically Active Imiquimod Formulation." Pharmaceutical Development and Technology, vol. 4(1), 1999, pp. 35-43. (Year: 1999).*

Yuxin Lin, Jianxin Xu, and Huiyin Lan. "Tumor-associated macrophages in tumor metastasis: biological roles and clinical therapeutic applications." Journal of Hematology and Oncology, vol. 12:76, 2019, pp. 1-16. (Year: 2019).*

Max Tsai, Ze Lu, Jie Wang, Teng-Kuang Yeh, M. Guillaume Wientjes, and Jessie L.-S. Au. "Effects of Carrier on Disposition and Antitumor Activity of Intraperitoneal Paclitaxel." Pharmaceutical Research, vol. 24, No. 9, Sep. 2007, pp. 1691-1701. (Year: 2007).*

Al-Muhammed, J. et al. (May-Jun. 1996). "In-vivo studies on dexamethasone sodium phosphate liposomes," *J Microencapsul* 13(3):293-306.

Anselmo, A.C. et al. (Jun. 3, 2016, e-collection Mar. 2016). "Nanoparticles in the clinic," *Bioeng Transl Med* 1(1):10-29.

Armstrong, D.K. (2002). "Relapsed ovarian cancer: challenges and management strategies for a chronic disease," *Oncologist* 7 Suppl 5:20-28.

Berge, S.M. et al. (Jan. 1977). "Pharmaceutical salts" *J Pharm Sci* 66(1)1-19.

Caltagirone, C. et al. (Jul. 21, 2015). "Silica-based nanoparticles: a versatile tool for the development of efficient imaging agents," *Chem Soc Rev* 44(14):4645-4671.

Cao, P. et al. (Jun. 21, 2017, e-published May 18, 2017). "Intraperitoneal Administration of Neural Stem Cell-Nanoparticle Conjugates Targets Chemotherapy to Ovarian Tumors," *Bioconjug Chem* 28(6):1767-1776.

Chonn, A. et al. (Dec. 1995). "Recent advances in liposomal drug-delivery systems," *Curr Opin Biotechnol* 6(6):698-708.

Colby, A.H. et al. (Feb. 28, 2017, e-published Feb. 1, 2017). "Highly Specific and Sensitive Fluorescent Nanoprobes for Image-Guided Resection of Sub-Millimeter Peritoneal Tumors," *ACS Nano* 11(2):1466-1477.

Di Pasqua, A.J. et al. (Jan. 2013, e-published Oct. 25, 2012). "Neutron-activatable holmium-containing mesoporous silica nanoparticles as a potential radionuclide therapeutic agent for ovarian cancer," *J Nucl Med* 54(1):111-116.

Eyles, J.E. et al. (Jul. 1997). "Oral delivery and fate of poly(lactic acid) microsphere-encapsulated interferon in rats," *J Pharm Pharmacol* 49(7):669-674.

Feng, J. et al. (May 1, 2013). "Effects of size and targeting ligand on biodistribution of liposome nanoparticles in tumor mice," *J Nucl Med Meeting Abstracts* 1339.

Foley, O.W. et al. (Apr. 2013). "Recurrent epithelial ovarian cancer: an update on treatment," *Oncology* 27(4):288-294, 298.

Franklin, R.A. et al. (May 23, 2014, e-published May 8, 2014). "The cellular and molecular origin of tumor-associated macrophages," *Science* 344(6186)921-925.

Gao, Z.H. et al. (Jun. 1995). "Controlled release of a contraceptive steroid from biodegradable and injectable gel formulations: in vitro evaluation," *Pharm Res* 12(6):857-863.

Grivennikov, S I. et al. (Mar. 19, 2010). "Immunity, Inflammation, and Cancer," *Cell* 140(6):883-899.

Iacob, M. et al. (2016, e-published Dec. 28, 2016). "From iron coordination compounds to metal oxide nanoparticles," *Beilstein J Nanotechnol* 7:2074-2087.

International Search Report dated Sep. 20, 2018, for PCT Application No. PCT/US2018/040405, filed Jun. 29, 2018, 4 pages.

Kamei, T. et al. (Jan. 2011, e-published Oct. 13, 2010). "Spatial distribution of intraperitoneally administrated paclitaxel nanoparticles solubilized with poly (2-methacryloxyethyl phosphorylcholine-co n-butyl methacrylate) in peritoneal metastatic nodules," *Cancer Sci* 102(1):200-205.

(56) References Cited

OTHER PUBLICATIONS

Lisi, L. et al. (Apr. 3, 2017, e-published Mar. 2, 2017). "Expression of iNOS, CD163 and ARG-1 taken as M1 and M2 markers of microglial polarization in human glioblastoma and the surrounding normal parenchyma," *Neurosci Lett* 645:106-112.

Lu, Z. et al. (Dec. 2008, e-published Sep. 9, 2008). "Tumor-penetrating microparticles for intraperitoneal therapy of ovarian cancer," *J Pharmacol Exp Ther* 327(3):673-682.

Marcus-Sakura, C.J. (Aug. 1, 1988). "Techniques for using antisense oligodeoxyribonucleotides to study gene expression," Anal. Biochem. 172(2):289-295.

Mignogna, C. et al. (Jun. 2016, e-published Feb. 24, 2016). "A reappraisal of macrophage polarization in glioblastoma: Histopathological and immunohistochemical findings and review of the literature," *Pathol Res Pract* 212(6):49-499.

Ostro, M.J. et al. (Aug. 1989). "Use of liposomes as injectable-drug delivery systems," *Am J Hosp Pharm* 46(8):1576-1587.

"Survival rates for ovarian cancer" (Apr. 11, 2018). <located at http://www.cancer.org/cancer/ovariancancer/overyiewguide/ovarian-cancer-overview-survival> 15 pages.

Phillips, E. et al. (Oct. 29, 2014). "Clinical translation of an ultrasmall inorganic optical-PET imaging nanoparticle probe," *Sci Transl Med* 6(260):260ra149.

Qian, B.Z. et al. (Apr. 2, 2010). "Macrophage diversity enhances tumor progression and metastasis," *Cell* 141(1):39-51.

Rao, K.P. (1995). "Recent developments of collagen-based materials for medical applications and drug delivery systems," *J Biomater Sci Polym Ed* 7(7):623-645.

Soma, D. et al. (Oct. 2009, e-published Jun. 26, 2009). "Intraperitoneal administration of paclitaxel solubilized with poly(2-methacryloxyethyl phosphorylcholine-co n-butyl methacrylate) for peritoneal dissemination of gastric cancer," *Cancer Sci* 100(10):1979-1985.

Van Dam, G.M. et al. (Sep. 18, 2011). "Intraoperative tumor-specific fluorescence imaging in ovarian cancer by folate receptor-α targeting: first in-human results," *Nat Med* 17(10):1315-1319.

Weintraub, H.M. et al. (Jan. 1990). "Antisense RNA and DNA," *Sci Am* 262(1):40-46.

Written Opinion dated Sep. 20, 2018, for PCT Application No. PCT/US2018/040405, filed Jun. 29, 2018, 12 pages.

Wynn, T.A. et al. (Apr. 25, 2013). "Macrophage biology in development, homeostasis and disease," *Nature* 496(7446):445-455.

Zeisberger, S.M. et al. (Aug. 7, 2016, e-published Jul. 11, 2006). "Clodronate-liposome-mediated depletion of tumour-associated macrophages: a new and highly effective antiangiogenic therapy approach," *British Journal of Cancer* 95(3):272-281.

Zhang, Q. et al. (Mar. 31, 2016, e-published Jan. 21, 2016). "Serum-resistant CpG-STAT3 decoy for targeting survival and immune checkpoint signaling in acute myeloid leukemia," *Blood* 127(13):1687-1700.

Zivanovic, O. et al. (Sep. 2008). "Surgical resection and reconstruction for advanced and recurrent gynecologic malignancies," *Expert Review of Obstetrics & Gynecology* 3(5): 15 pages.

\* cited by examiner

FIG. 1A
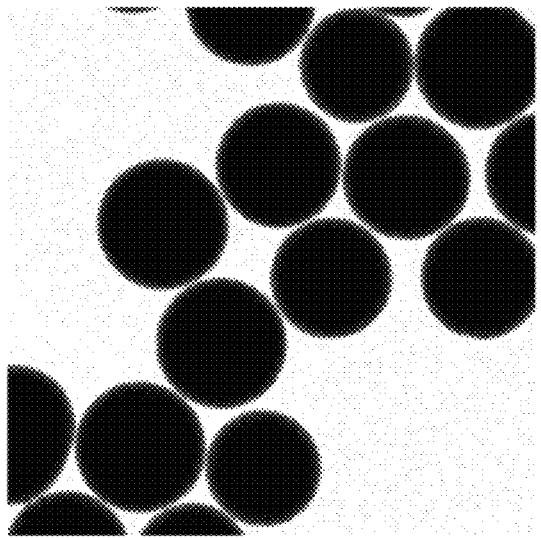
FIG. 1B
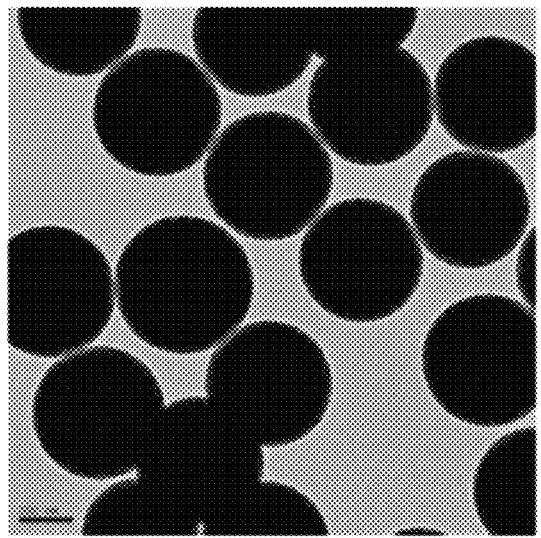
FIG. 1C
| Run | Mobility | Zeta Potential (mV) | Rel. Residual |
|---|---|---|---|
| 1 | 3.08 | 39.37 | 0.0126 |
| 2 | 2.92 | 37.43 | 0.0219 |
| 3 | 3.12 | 39.93 | 0.0144 |
| 4 | 3.12 | 39.92 | 0.0171 |
| 5 | 2.84 | 36.38 | 0.0280 |
| 6 | 2.71 | 34.67 | 0.0209 |
| 7 | 2.33 | 29.81 | 0.0092 |
| 8 | 2.18 | 27.86 | 0.0097 |
| 9 | 1.81 | 23.10 | 0.0165 |
| 10 | 1.44 | 18.46 | 0.0115 |
| Mean | 2.55 | 32.69 | 0.0162 |
| Std. Error | 0.19 | 2.39 | 0.0019 |
| Combined | 2.54 | 32.56 | 0.0049 |
FIG. 1D
| Run | Mobility | Zeta Potential (mV) | Rel. Residual |
|---|---|---|---|
| 1 | -0.97 | -12.36 | 0.0153 |
| 2 | -1.16 | -14.88 | 0.0124 |
| 3 | -1.14 | -14.59 | 0.0353 |
| 4 | -1.43 | -18.35 | 0.0108 |
| 5 | -1.59 | -20.34 | 0.0149 |
| 6 | -2.14 | -27.35 | 0.0152 |
| 7 | -2.20 | -28.15 | 0.0141 |
| 8 | -2.19 | -28.07 | 0.0125 |
| 9 | -2.34 | -29.93 | 0.0096 |
| 10 | -2.32 | -29.63 | 0.0134 |
| Mean | -1.75 | -22.37 | 0.0154 |
| Std. Error | 0.17 | 2.21 | 0.0023 |
| Combined | -1.75 | -22.42 | 0.0062 |

Stat3 inhibition activate the tumor associated macrophages (Flow cytometry)

FIG. 11A
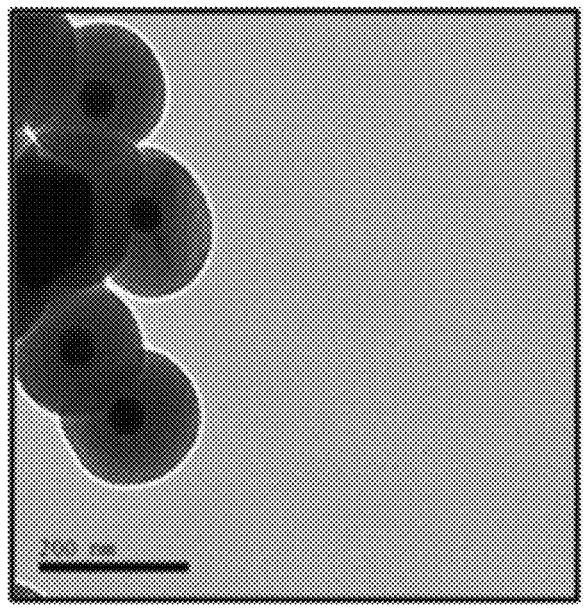
FIG. 11B
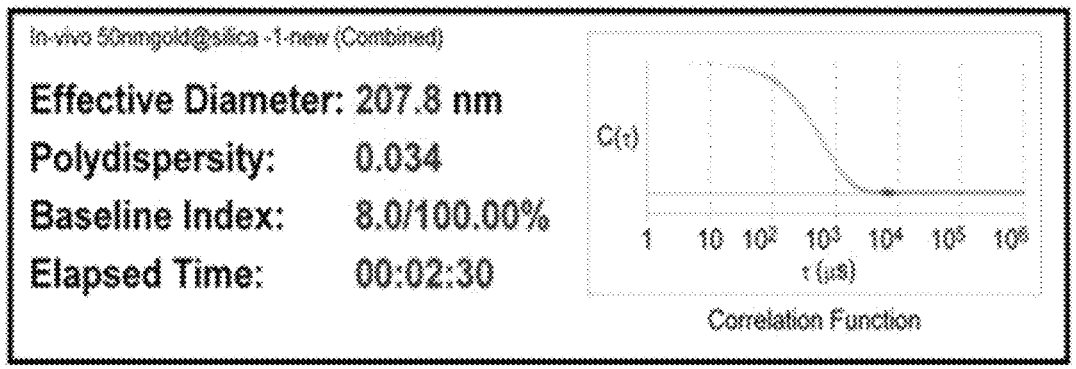
FIG. 11C
| Run | Mobility | Zeta Potential (mV) | Rel. Residual |
|---|---|---|---|
| 1 | -3.58 | -45.85 | 0.0168 |
| 2 | -3.43 | -43.84 | 0.0282 |
| 3 | -3.50 | -44.81 | 0.0151 |
| 4 | -3.56 | -45.61 | 0.0174 |
| 5 | -3.36 | -42.98 | 0.0292 |
| 6 | -3.58 | -45.79 | 0.0218 |
| 7 | -3.42 | -43.74 | 0.0166 |
| 8 | -3.26 | -41.76 | 0.0246 |
| 9 | -3.71 | -47.43 | 0.0150 |
| 10 | -3.80 | -48.59 | 0.0271 |
| Mean | -3.52 | -45.04 | 0.0212 |
| Std. Error | 0.05 | 0.65 | 0.0018 |
| Combined | -3.52 | -45.01 | 0.0121 |

| Hydroxyl-Silica-NP | Amine-Silica-NP | PEG-Silica-NP |
|---|---|---|
|  |  |  |
| $\zeta$-potential (mV): -55.74<br>HD (nm): 443.9 | $\zeta$-potential (mV): +22.88<br>HD (nm): 464.4 | $\zeta$-potential (mV): +10.58<br>HD (nm): 397.3 |

% TAMs out of total red positive cells in NPs mice

40mg/mL PLGA 5% PVA with Imiquimod (2.5mg/mL)

PLGA IMQ Original Recipe (Combined)

Effective Diameter: 507.8 nm
Polydispersity: 0.241
Baseline Index: 8.2/100.00%
Elapsed Time: 00:07:30

Correlation Function

COMPOSITIONS AND METHODS OF MODULATING MACROPHAGE ACTIVITY

CROSS-REFERENCES TO RELATED APPLICATIONS

This application is the national stage filing under USC 371 of international application PCT/US2018/040405, filed Jun. 29, 2018, which claims the benefit of U.S. Provisional Application No. 62/527,531, filed on Jun. 30, 2017, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant number R01 CA197359 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048440-640N01US Sequence Listing_ST25.txt, created Dec. 18, 2019, 10,602 bytes, machine format IBM-PC, MS Windows operating system, is hereby incorporated by reference.

BACKGROUND

A goal of nanomedicine is to design and synthesize drug delivery vehicles that can carry sufficient drug loads, efficiently cross physiological barriers to reach target sites, and safely and sustainably treat diseases. Disclosed herein, inter alia, are solutions to these and other problems in the art.

BRIEF SUMMARY OF THE INVENTION

In an aspect is provided a method of modulating an immune response in a subject in need thereof, the method including intraperitoneally administering a therapeutically effective amount of a nanoparticle composition to the subject.

In an aspect is provided a method of delivering an intracellular modulating agent to a cell in a subject, the method including intraperitoneally administering to the subject an effective amount of the nanoparticle composition or the pharmaceutical composition as described herein, including embodiments.

In an aspect is provided a method of modulating the activity of a macrophage in a subject, the method including intraperitoneally administering an effective amount of a nanoparticle composition to the subject.

In another aspect is provided a method of treating a disease (e.g., a macrophage-associated disease, autoimmune disease, inflammatory disease, or a cancer of an organ in the intraperitoneal cavity), the method including intraperitoneally administering to a subject in need thereof a therapeutically effective amount of a nanoparticle composition or pharmaceutical composition.

In an aspect is provided a silica nanoparticle non-covalently bound to a plurality of nucleic acids, wherein the silica nanoparticle has a net positive charge in the absence of the plurality of nucleic acids.

In another aspect, is provided a pharmaceutical composition including a nanoparticle composition as described herein, and a pharmaceutically acceptable excipient.

BRIEF DESCRIPTION OF THE DRAWINGS

FIGS. 1A-1D. Characterization of particles before and after loading. The size is unchanged by the thin layer of CpG-STAT3Decoy absorbed (compare FIG. 1A to FIG. 1B), but the zeta (i.e. measured charge) is inverted as observed in FIG. 1C which corresponds to the nanoaprticles found in FIG. 1A (i.e., the functionalized silica nanoparticles) and FIG. 1D which corresponds to the nanoparticles in FIG. 1B (i.e. the CpG-STAT3 coated nanoparticles). The scale bar in the lower left corner is 200 nm.

(FIG. 6A) Wide field imaging (Spectral Ami-X) of the organ block demonstrates selective accumulation of SiNPs (red) at ovarian tumor foci (green), Scale bar: 1 cm. (FIG. 6B) Confocal images of the sectioned tumors (SiNPs red, tumors green/dense blue nuclei, Scale bar: 100 m).

FIGS. 11A-C. Characteristics of Au@SiNPs. (11A) TEM images of 50 nm gold cores in 75 nm silica shell Scale bar=200 nm). (11B) Hydrodynamic size (nm) of Au@SiNPs and (11C) Zeta potential of Au@SiNPs (mV).

(FIG. 17A) Confocal image of representative sectioned tumor 4 days after IP injection of red fluorescently polystyrene NPs. (FIG. 17B) Polystyrene NPs red, tumors green, DAPI stained nuclei blue. Anti-CD45, Anti-CD11b and Anti-F4/80 antibody staining yellow to identify TAMs. Note merged images in far right panels showing co-localization of polystyrene NPs and macrophages at tumor surface. Scale Bar=50 am.

FIG. 18A and FIG. 18B are the results of the same experiment in different mice.

(FIG. 30A) Leica Z16 dissection macroscope images of the IP cavity organs 4 days after IP injection of 500 nm red fluorescent-labeled SiNPs (EGFP tumors green) before any surgery, after the surgery done with the naked eye and after image guided surgery. Scale bar=1.0 cm (FIG. 30B) Quantification of % tumor area comparing surgical resection of tumors by the naked eye versus an additional image guided surgery with red fluorescent SiNPs. The symbols, diamond and square, represent two separate measurements (i.e. two different mice). The average was taken to determine if there is a difference between a surgery with NPs (image guided surgery) or without the NPs (with the naked eye). There is a significant statistical difference between the groups. ($p<0.05$)

(FIG. 33A) Red fluorescent labeled SiNPs, (FIG. 33B) Red fluorescent labeled polystyrene NPs. Secondary antibody Alexa Fluor 647 goat anti-rat (Invitrogen) yellow. eGFP tumors green, DAPI nuclei blue. Scale bar=50 μm.

DETAILED DESCRIPTION

Figure 2:
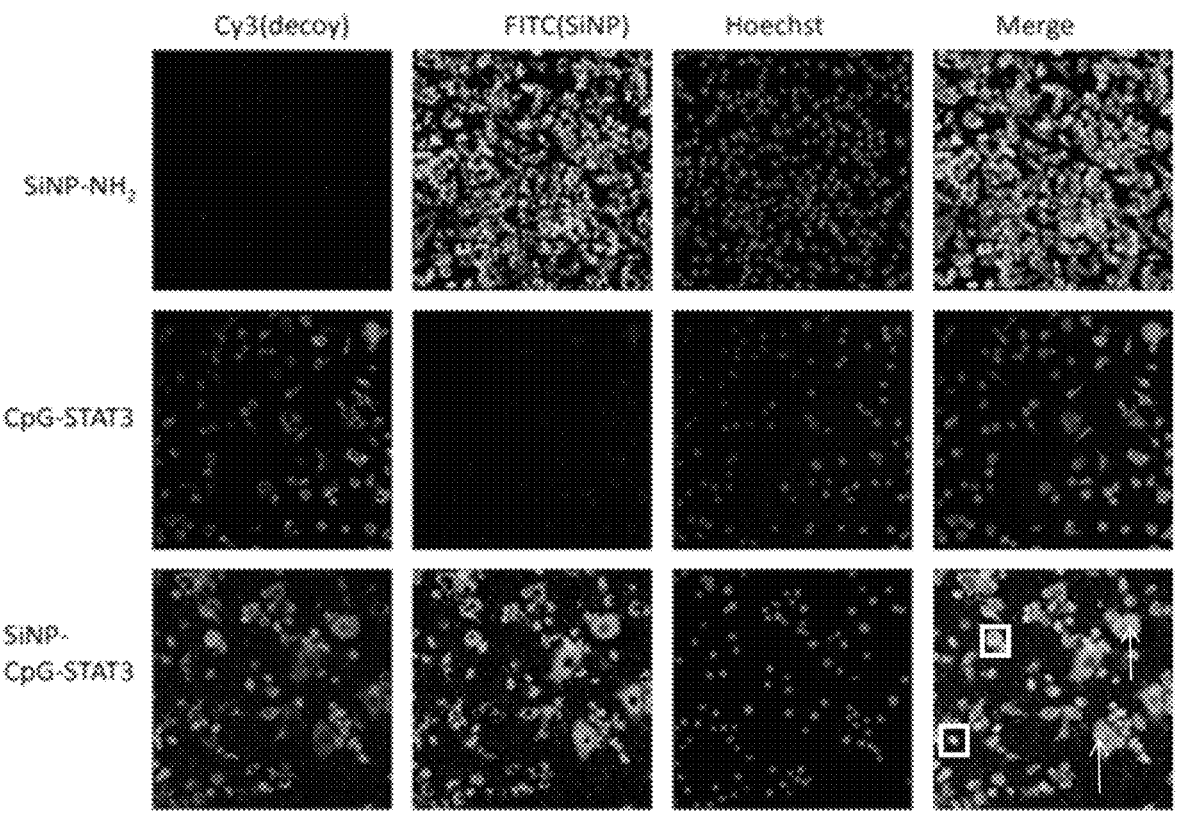
FIG. 2. In cell culture, following cell uptake, the particles and CpG-STAT3Decoy sometimes stay together (square in bottom right image) and in other cases, separate inside the cell (arrows). This suggests delivery is accomplished by the particle-bound material and dissociation occurs in the cells.

Tumor associated macrophages (TAMs) are macrophages that are associated with the tumor microenvironment, and are found in close proximity or within the tumor. TAMs are involved both in pro-tumor as well as in anti-tumor processes. Typically, the presence of TAMs in the tumor microenvironment has been associated with shorter patient survival, cancer progression and poor prognosis. Disclosed herein, among other compositions, are nanoparticles that can target TAMs when administered via intraperitoneal injection. The use of such targeted delivery system for TAMs can be used as selective therapeutic delivery treatments.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g. O, N, P, Si, and S), and wherein the nitrogen and sulfur atoms may optionally be oxidized, and the nitrogen heteroatom may optionally be quaternized. The heteroatom(s) (e.g. O, N, P, S, and Si) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—S—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —C—H=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in addition to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form ($CH_2$)$_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

Each of the above terms (e.g., "alkyl", "heteroalkyl", "cycloalkyl", "heterocycloalkyl", "aryl", and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —NR'SO$_2$R", —NR'C(O)R", —NR'C(O)—OR", or —NR'OR" in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", or —NR'OR", in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$F, —OCH$_2$I, —N$_3$, unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$ alkyl), unsubstituted heteroalkyl (e.g., 2 to 20 membered, 2 to 12 membered, 2 to 8 membered, 2 to 6 membered, 4 to 6 membered, 2 to 3 membered, or 4 to 5 membered heteroalkyl), unsubstituted cycloalkyl (e.g., $C_3$-$C_{10}$, $C_3$-$C_8$, $C_3$-$C_6$, $C_4$-$C_6$, or $C_5$-$C_6$ cycloalkyl), unsubstituted heterocycloalkyl (e.g., 3 to 10 membered, 3 to 8 membered, 3 to 6 membered, 4 to 6 membered, 4 to 5 membered, or 5 to 6 membered heterocycloalkyl), unsubstituted aryl (e.g., $C_6$-$C_{12}$ aryl, $C_6$-$C_{10}$ aryl, or phenyl), or unsubstituted heteroaryl (e.g., 5 to 12 membered, 5 to 10 membered, 5 to 9 membered, or 5 to 6 membered heteroaryl), and (B) alkyl (e.g., $C_1$-$C_{20}$, $C_1$-$C_{12}$, $C_1$-$C_8$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from:

(i) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2F$, —$OCH_2I$, —$N_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$ alkyl), unsubstituted heteroalkyl (e.g., 2 to 20 membered, 2 to 12 membered, 2 to 8 membered, 2 to 6 membered, 4 to 6 membered, 2 to 3 membered, or 4 to 5 membered heteroalkyl), unsubstituted cycloalkyl (e.g., $C_3$-$C_{10}$, $C_3$-$C_8$, $C_3$-$C_6$, $C_4$-$C_6$, or $C_5$-$C_6$ cycloalkyl), unsubstituted heterocycloalkyl (e.g., 3 to 10 membered, 3 to 8 membered, 3 to 6 membered, 4 to 6 membered, 4 to 5 membered, or 5 to 6 membered heteroalkyl), unsubstituted aryl (e.g., $C_6$-$C_{12}$ aryl, $C_6$-$C_{10}$ aryl, or phenyl), or unsubstituted heteroaryl (e.g., 5 to 12 membered, 5 to 10 membered, 5 to 9 membered, or 5 to 6 membered heteroaryl), and (ii) alkyl (e.g., $C_1$-$C_{20}$, $C_1$-$C_{12}$, $C_1$-$C_8$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from:

(a) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2F$, —$OCH_2I$, —$N_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$ alkyl), unsubstituted heteroalkyl (e.g., 2 to 20 membered, 2 to 12 membered, 2 to 8 membered, 2 to 6 membered, 4 to 6 membered, 2 to 3 membered, or 4 to 5 membered heteroalkyl), unsubstituted cycloalkyl (e.g., $C_3$-$C_{10}$, $C_3$-$C_8$, $C_3$-$C_6$, $C_4$-$C_6$, or $C_5$-$C_6$ cycloalkyl), unsubstituted heterocycloalkyl (e.g., 3 to 10 membered, 3 to 8 membered, 3 to 6 membered, 4 to 6 membered, 4 to 5 membered, or 5 to 6 membered heterocycloalkyl), unsubstituted aryl (e.g., $C_6$-$C_{12}$ aryl, $C_6$-$C_{10}$ aryl, or phenyl), or unsubstituted heteroaryl (e.g., 5 to 12 membered, 5 to 10 membered, 5 to 9 membered, or 5 to 6 membered heteroaryl), and (b) alkyl (e.g., $C_1$-$C_{20}$, $C_1$-$C_{12}$, $C_1$-$C_8$, $C_1$-$C_6$, $C_1$-$C_4$, or $C_1$-$C_2$ alkyl), heteroalkyl (e.g., 2 to 20 membered, 2 to 12 membered, 2 to 8 membered, 2 to 6 membered, 4 to 6 membered, 2 to 3 membered, or 4 to 5 membered heteroalkyl), cycloalkyl (e.g., $C_3$-$C_{10}$, $C_3$-$C_8$, $C_3$-$C_6$, $C_4$-$C_6$, or $C_5$-$C_6$ cycloalkyl), heterocycloalkyl (e.g., 3 to 10 membered, 3 to 8 membered, 3 to 6 membered, 4 to 6 membered, 4 to 5 membered, or 5 to 6 membered heterocycloalkyl), aryl (e.g., $C_6$-$C_{12}$ aryl, $C_6$-$C_{10}$ aryl, or phenyl), or heteroaryl (e.g., 5 to 12 membered, 5 to 10 membered, 5 to 9 membered, or 5 to 6 membered heteroaryl), substituted with at least one substituent selected from: oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2F$, —$OCH_2I$, —$N_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$ alkyl), unsubstituted heteroalkyl (e.g., 2 to 20 membered, 2 to 12 membered, 2 to 8 membered, 2 to 6 membered, 4 to 6 membered, 2 to 3 membered, or 4 to 5 membered heteroalkyl), unsubstituted cycloalkyl (e.g., $C_3$-$C_{10}$, $C_3$-$C_8$, $C_3$-$C_6$, $C_4$-$C_6$, or $C_5$-$C_6$ cycloalkyl), unsubstituted heterocycloalkyl (e.g., 3 to 10 membered, 3 to 8 membered, 3 to 6 membered, 4 to 6 membered, 4 to 5 membered, or 5 to 6 membered heterocycloalkyl), unsubstituted aryl (e.g., $C_6$-$C_{12}$ aryl, $C_6$-$C_{10}$ aryl, or phenyl), or unsubstituted heteroaryl (e.g., 5 to 12 membered, 5 to 10 membered, 5 to 9 membered, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compositions, intracellular modulating agents, therapeutic agents) that may be in a prodrug form. Prodrugs of the compounds described herein are those compounds that readily undergo chemical changes under select physiological conditions to provide the final agents (e.g. compositions, intracellular modulating agents, therapeutic agents). Additionally, prodrugs can be converted to agents (e.g. compositions, intracellular modulating agents, therapeutic agents) by chemical or biochemical methods in an ex vivo environment. Prodrugs described herein include compounds that readily undergo chemical changes under select physiological conditions to provide agents (e.g. compositions, intracellular modulating agents, therapeutic agents) to a biological system (e.g. in a subject).

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The symbol " $\sim\!\!\sim$ " denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat hyperproliferative disorders, such as cancer (e.g., cancer of the intraperitoneal organs). For example, certain methods herein treat cancer by decreasing or reducing or preventing the occurrence, growth, metastasis, or progression of cancer or by decreasing or reducing or preventing a symptom of cancer. Symptoms of cancer (e.g., cancer of the intraperitoneal organs) would be known or may be determined by a person of ordinary skill in the art. The term "treating" and conjugations thereof, include prevention of an injury, pathology, condition, or disease (e.g. preventing the development of one or more symptoms of cancer (e.g. cancer of the intraperitoneal organs).

The terms "treating" or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The term "treating" and conjugations thereof, may include prevention of an injury, pathology, condition, or disease. In embodiments, treating is preventing. In embodiments, treating does not include preventing.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound, pharmaceutical composition, or method provided herein include ovarian cancer, lymphoma, sarcoma, bladder cancer, bone cancer, brain cancer, brain tumor, cervical cancer, colon cancer, esophageal cancer, gastric cancer, head and neck cancer, kidney cancer, myeloma, thyroid cancer, leukemia, prostate cancer, breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma, cisplatin resistant lung cancer, carboplatin resistant lung cancer, platinum-based compound resistant lung cancer), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer. In embodiments "cancer" refers to a cancer resistant to an anti-cancer therapy (e.g. treatment with an anti-cancer agent).

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cutaneous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis *nodosa*, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As used herein, the term "inflammatory disease" refers to a disease or condition characterized by aberrant inflammation (e.g. an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays.

As is well known in the art, therapeutically effective amounts for use in humans can also be determined from animal models.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time.

The term "associated" or "associated with" in the context of a substance or substance activity or function associated with a disease (e.g. cancer, ovarian cancer, bladder cancer, head and neck cancer, brain cancer, breast cancer, lung cancer, cervical cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example cancer may be treated with a composition (e.g. compound, composition, nanoparticle, all as described herein) effective for inhibiting DNA replication.

In this disclosure, "comprises," "comprising," "containing" and "having" and the like can have the meaning ascribed to them in U.S. Patent law and can mean "includes," "including," and the like. "Consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents, which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor (e.g., composition described herein). In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. In embodiments, inhibition refers to a decrease in DNA replication or transcription. In some embodiments inhibition refers to reduction of a disease or symptoms of disease (e.g. cancer, stomach cancer, duodenum cancer, jejunum cancer, ileum cancer, cecum cancer, appendix cancer, colon cancer, liver cancer, spleen cancer, pancreatic cancer, or ovarian cancer). Thus, inhibition may include, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation). For example a JAK2 inhibitor is a compound that negatively affects (e.g. decreases) the activity or function of JAK2 relative to the activity or function of JAK2 in the absence of the inhibitor.

As defined herein, the term "activation", "activate", "activating", "activator" and the like in reference to a protein-activator (e.g. agonist) interaction means positively affecting (e.g. increasing) the activity or function of the protein relative to the activity or function of the protein in the absence of the activator (e.g. composition described herein). In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein decreased in a disease (e.g., a protein, which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "modulator" refers to a composition that increases or decreases the level of a target molecule or the function of a target molecule relative to the level of a target molecule or the function of a target molecule in the absence of the composition.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In embodiments, the subject is human.

"Disease" or "condition" refer to a state of being or health status of a patient or subject capable of being treated with a compound, pharmaceutical composition, or method provided herein. In embodiments, the disease is cancer. In embodiments, the disease is cancer of an organ in the intraperitoneal cavity (e.g., stomach cancer, duodenum cancer, jejunum cancer, ileum cancer, cecum cancer, appendix cancer, colon cancer, liver cancer, spleen cancer, pancreatic cancer, or ovarian cancer). In embodiments, the disease is inflammation.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. By "co-administer" it is meant that a composition described herein is administered at the same time, just prior to, or just after the administration of one or more additional therapies. The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present disclosure can also be delivered as nanoparticles.

Pharmaceutical compositions provided by the present invention include compositions wherein the active ingredient (e.g. compounds described herein, including embodiments or examples) may be contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any composition described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compositions described herein can be used in combination with one another, with other active agents (e.g. anti-cancer agents) known to be useful in treating a disease described herein (e.g., a macrophage-associated disease or a cancer of an organ in the intraperitoneal cavity), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent (e.g. anti-cancer agent). Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

"Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodeaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Vanadocene acetylacetonate, Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, Diazonamide A, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alphainterferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/ PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, or the like.

"Analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g. —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive groups used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding; and (m) metal bonding to reactive phosphorus groups (e.g. phosphines) to form, for example, phosphate diester bonds.

(n) azides coupled to alkynes using copper catalyzed cycloaddition click chemistry.

(o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

The term "bound" as used herein is used in accordance with its plain and ordinary meaning and refers to the association between atoms or molecules. The association can be direct or indirect. For example, bound atoms or molecules may be direct, e.g., by covalent bond or linker (e.g. a first linker or second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like).

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics, which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

An "antisense nucleic acid" as referred to herein is a nucleic acid (e.g., DNA or RNA molecule) that is complementary to at least a portion of a specific target nucleic acid and is capable of reducing transcription of the target nucleic acid (e.g. mRNA from DNA), reducing the translation of the target nucleic acid (e.g. mRNA), altering transcript splicing (e.g. single stranded morpholino oligo), or interfering with the endogenous activity of the target nucleic acid. Weintraub, *Scientific American*, 262:40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid. In embodiments, the antisense nucleic acid hybridizes to the target nucleic acid in vitro. In embodiments, the antisense nucleic acid hybridizes to the target nucleic acid in a cell. In embodiments, the antisense nucleic acid hybridizes to the target nucleic acid in an organism. In embodiments, the antisense nucleic acid hybridizes to the target nucleic acid under physiological conditions. Antisense nucleic acids may comprise naturally occurring nucleotides or modified nucleotides such as, e.g., phosphorothioate, methylphosphonate, and -anomeric sugar-phosphate, backbonemodified nucleotides.

In the cell, the antisense nucleic acids hybridize to the corresponding RNA forming a double-stranded molecule. The antisense nucleic acids interfere with the endogenous behavior of the RNA and inhibit its function relative to the absence of the antisense nucleic acid. Furthermore, the double-stranded molecule may be degraded via the RNAi pathway. The use of antisense methods to inhibit the in vitro translation of genes is well known in the art (Marcus-Sakura, *Anal. Biochem.*, 172:289, (1988)). Further, antisense molecules which bind directly to the DNA may be used. Antisense nucleic acids may be single or double stranded nucleic acids. Non-limiting examples of antisense nucleic acids include siRNAs (including their derivatives or pre-cursors, such as nucleotide analogs), short hairpin RNAs (shRNA), micro RNAs (miRNA), saRNAs (small activating RNAs) and small nucleolar RNAs (snoRNA) or certain of their derivatives or pre-cursors.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanidine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

The term "STAT" or "STAT transcription factor" are used interchangeably and refer to a "Signal transducer and activator of transcription" protein and homologs thereof (e.g. STAT1, STAT2, STAT3, STAT4, STAT5A, STAT5B, or STAT6). In embodiments, "STAT transcription factor" refers to a human protein (e.g. STAT1, STAT2, STAT3, STAT4, STAT5A, STAT5B, or STAT6). Included in the term "STAT transcription factor" are the wildtype and mutant forms of the protein (e.g. STAT1, STAT2, STAT3, STAT4, STAT5A, STAT5B, or STAT6). In embodiments, "STAT transcription factor" refers to the wildtype protein (e.g. STAT1, STAT2, STAT3, STAT4, STAT5A, STAT5B, or STAT6). In embodiments, "STAT transcription factor" refers to a mutant protein (e.g. STAT1, STAT2, STAT3, STAT4, STAT5A, STAT5B, or STAT6). "Phosphorylated STAT" refers to a STAT protein (e.g. STAT1, STAT2, STAT3, STAT4, STAT5A, STAT5B, or STAT6) that is phosphorylated and activated by the phosphorylation. In embodiments, activation of a STAT transcription factor (e.g. STAT1, STAT2, STAT3, STAT4, STAT5A, STAT5B, or STAT6) means the STAT (e.g. STAT1, STAT2, STAT3, STAT4, STAT5A, STAT5B, or STAT6) is capable of activating transcription. In embodiments, activated STAT (e.g. STAT1, STAT2, STAT3, STAT4, STAT5A, STAT5B, or STAT6) is phosphorylated on STAT1 Y701, STAT2, Y690, STAT3 Y705, STAT4 Y693, STAT5A Y694, STAT5B Y694, STAT6 Y641, or a residue corresponding to one of those residues, forms dimers (e.g. homodimers or heterodimers), translocates to the nucleus, and activates transcription. In embodiments, activated STAT (e.g. STAT1, STAT2, STAT3, STAT4, STAT5A, STAT5B, or STAT6) forms homodimers. In embodiments, activated STAT (e.g. STAT1, STAT2, STAT3, STAT4, STAT5A, STAT5B, or STAT6) forms heterodimers. An example of a protein that phosphorylates STAT (e.g. STAT1, STAT2, STAT3, STAT4, STAT5A, STAT5B, or STAT6) and thereby activate a STAT (e.g. STAT1, STAT2, STAT3, STAT4, STAT5A, STAT5B, or STAT6) includes JAK.

The term "STAT-binding nucleic acid sequence" refers to a nucleic acid capable of binding to a STAT (e.g. STAT1, STAT2, STAT3, STAT4, STAT5A, STAT5B, or STAT6) or a nucleic acid that forms part of a STAT-binding substituent (e.g. STAT1-, STAT2-, STAT3-, STAT4-, STAT5A-, STAT5B-, or STAT6-binding substituent). A STAT3-binding nucleic acid sequence is a nucleic acid capable of binding to STAT3 or a nucleic acid that forms part of a STAT3-binding substituent (STAT3-binding nucleic acid substituent).

The term "STAT1" refers to a "Signal transducer and activator of transcription 1" protein and homologs thereof. In embodiments, "STAT1" refers to the protein associated with Entrez Gene 6772, OMIM 600555, UniProt P42224, and/or RefSeq (protein) NP_009330. In embodiments, the reference numbers immediately above refer to the protein, and associated nucleic acids, known as of the date of filing of this application.

The term "STAT2" refers to a "Signal transducer and activator of transcription 2" protein and homologs thereof. In embodiments, "STAT2" refers to the protein associated with Entrez Gene 6773, OMIM 600556, UniProt P52630, and/or RefSeq (protein) NP_005410. In embodiments, the reference numbers immediately above refer to the protein, and associated nucleic acids, known as of the date of filing of this application.

The term "STAT4" refers to a "Signal transducer and activator of transcription 4" protein and homologs thereof. In embodiments, "STAT4" refers to the protein associated with Entrez Gene 6775, OMIM 600558, UniProt Q14765, and/or RefSeq (protein) NP_001230764. In embodiments, the reference numbers immediately above refer to the protein, and associated nucleic acids, known as of the date of filing of this application.

The term "STAT5A" refers to a "Signal transducer and activator of transcription 5A" protein and homologs thereof. In embodiments, "STAT5A" refers to the protein associated with Entrez Gene 6776, OMIM 601511, UniProt P42229, and/or RefSeq (protein) NP_003143. In embodiments, the reference numbers immediately above refer to the protein, and associated nucleic acids, known as of the date of filing of this application.

The term "STAT5B" refers to a "Signal transducer and activator of transcription 5B" protein and homologs thereof. In embodiments, "STAT5B" refers to the protein associated with Entrez Gene 6777, OMIM 604260, UniProt P51692, and/or RefSeq (protein) NP_036580. In embodiments, the reference numbers immediately above refer to the protein, and associated nucleic acids, known as of the date of filing of this application.

The term "STAT6" refers to a "Signal transducer and activator of transcription 6" protein and homologs thereof. In embodiments, "STAT6" refers to the protein associated with Entrez Gene 6778, OMIM 601512, UniProt P42226, and/or RefSeq (protein) NP_001171549. In embodiments, the reference numbers immediately above refer to the protein, and associated nucleic acids, known as of the date of filing of this application.

The term "STAT3" refers to the protein "Signal transducer and activator of transcription 3" and homologs thereof. In embodiments, "STAT3" refers to the human protein. Included in the term "STAT3" are the wildtype and mutant forms of the protein. In embodiments, "STAT3" refers to the wildtype protein. In embodiments, "STAT3" refers to a mutant protein. In embodiments, "STAT3" refers to the protein associated with Entrez Gene 6774, OMIM 102582, UniProt P40763, and/or RefSeq (protein) NP_003141. In embodiments, the reference numbers immediately above refer to the protein, and associated nucleic acids, known as of the date of filing of this application.

As used herein, the term "TLR-binding nucleic acid substituent" refers to a substituent or moiety capable of binding to a toll-like receptor ("TLR") or activating a toll-like receptor, including at least one nucleic acid. In embodiments, a TLR-binding nucleic acid substituent is capable of binding a TLR. In embodiments, a TLR-binding nucleic acid substituent is capable of activating a TLR. In embodiments, a TLR-binding nucleic acid substituent is capable of activating a TLR without directly binding the TLR. In embodiments, a TLR-binding nucleic acid substituent is capable of binding a TLR without activating the TLR. In embodiments, a TLR-binding nucleic acid substituent is a nucleic acid. In embodiments, the TLR-binding nucleic acid substituent includes at least one nucleic acid analog. In embodiments, the TLR-binding nucleic acid substituent includes at least one nucleic acid analog having an alternate backbone (e.g. phosphodiester derivative (e.g. phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite), peptide nucleic acid backbone(s), LNA, or linkages). In embodiments, a TLR-binding nucleic acid substituent includes or is DNA. In embodiments, a TLR-binding nucleic acid substituent includes or is RNA. In embodiments, a TLR-binding nucleic acid substituent includes or is a nucleic acid having internucleotide linkages selected from phosphodiesters and phosphodiester derivatives (e.g. phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite, or combinations thereof).

As used herein, the term "CpG motif" refers to a 5' C nucleotide connected to a 3' G nucleotide through a phosphodiester internucleotide linkage or a phosphodiester derivative internucleotide linkage. In embodiments, a CpG motif includes a phosphodiester internucleotide linkage. In embodiments, a CpG motif includes a phosphodiester derivative internucleotide linkage.

As used herein, the term "Class A CpG ODN" or "A-class CpG ODN" or "D-type CpG ODN" or "Class A CpG DNA sequence" is used in accordance with its common meaning in the biological and chemical sciences and refers to a CpG motif including oligodeoxynucleotide including one or more of poly-G sequence at the 5', 3', or both ends; an internal palindrome sequence including CpG motif; or one or more phosphodiester derivatives linking deoxynucleotides. In embodiments, a Class A CpG ODN includes poly-G sequence at the 5', 3', or both ends; an internal palindrome sequence including CpG motif; and one or more phosphodiester derivatives linking deoxynucleotides. In embodiments, the phosphodiester derivative is phosphorothioate.

As used herein, the term "STAT-binding substituent" or "STAT-binding nucleic acid substituent" refers to a composition including one or more nucleic acids capable of binding to a STAT transcription factor (e.g. STAT1, STAT2, STAT3, STAT4, STAT5A, STAT5B, or STAT6). In embodiments, a STAT-binding substituent includes DNA (e.g. including phosphodiester internucleotide linkages, phosphodiester derivative internucleotide linkages, or a combination of phosphodiester and phosphodiester derivative internucleotide linkages). In embodiments, a STAT-binding substituent (e.g. STAT1-, STAT2-, STAT3-, STAT4-, STAT5A-, STAT5B-, or STAT6-binding substituent) includes a DNA sequence identical (except that it may include one or more phosphodiester derivative linkage(s)) to the genomic DNA sequence a STAT transcription factor (e.g. STAT1, STAT2, STAT3, STAT4, STAT5A, STAT5B, or STAT6) binds when modulating transcription. In embodiments, a STAT-binding substituent (e.g. STAT1-, STAT2-, STAT3-, STAT4-, STAT5A-, STAT5B-, or STAT6-binding substituent) is a DNA sequence identical (except that it may include one or more phosphodiester derivative linkage(s)) to the genomic DNA sequence a STAT transcription factor (e.g. STAT1, STAT2, STAT3, STAT4, STAT5A, STAT5B, or STAT6) binds when modulating transcription.

A "nanoparticle," as used herein, is a particle wherein the longest diameter is less than or equal to 1000 nanometers. The longest dimension of the nanoparticle may be referred to herein as the length of the nanoparticle. The shortest dimension of the nanoparticle may be referred to herein refer as the width of the nanoparticle. Nanoparticles may be composed of any appropriate material. For example, nanoparticle cores may include appropriate metals and metal oxides thereof (e.g., a metal nanoparticle core), carbon (e.g., an organic nanoparticle core), polymerizable monomer (e.g., polymeric nanoparticle), lipids (e.g., micelle), silicon and oxides thereof (e.g., a silicon nanoparticle core) or boron and oxides thereof (e.g., a boron nanoparticle core), or mixtures thereof. Nanoparticles may be composed of at least two distinct materials, one material (e.g., iron oxide) forms the core and the other material forms the shell (e.g., silica) surrounding the core. Nanoparticles may be specific shapes known commonly in the art such as spherical (e.g., nanosphere), rod-like (e.g., nanobar, nanorod, nanowire), 2D-polygonal (e.g., triangle, disc, pentagon), or 3-d polyhedral (e.g., cube, tetrahedron, icosahedron). In embodiments, the nanoparticle is an inorganic nanoparticle.

An "inorganic nanoparticle" refers to a nanoparticle without carbon. For example, an inorganic nanoparticle may refer to a metal or metal oxide thereof (e.g., gold nanoparticle, iron nanoparticle) silicon and oxides thereof (e.g., a nonporous or mesoporous silica nanoparticle), or titanium and oxides thereof (e.g., titanium dioxide nanoparticle). In embodiments, the inorganic nanoparticle is a silica nanoparticle. The inorganic nanoparticle may be a metal nanoparticle. When the nanoparticle is a metal, the metal may be titanium, zirconium, gold, silver, platinum, cerium, arsenic, iron, aluminum or silicon. The metal nanoparticle may be titanium, zirconium, gold, silver, or platinum and appropriate metal oxides thereof. In embodiments, the nanoparticle is titanium oxide, zirconium oxide, cerium oxide, arsenic oxide, iron oxide, aluminum oxide, or silicon oxide. The metal oxide nanoparticle may be titanium oxide or zirconium oxide. The nanoparticle may be titanium. The nanoparticle may be gold. In embodiments, the metal nanoparticle is a gold nanoparticle. In embodiments, the inorganic nanoparticle may further include an agent, which contains carbon (e.g., an intracellular modulating agent).

A "mesoporous nanoparticle" is used in accordance with its plain ordinary meaning and refers to a nanoparticle with pores having an average diameter between about 2 nm and 50 nm. In contrast, a "nonporous nanoparticle" is used in accordance with its plain ordinary meaning and refers to a nanoparticle, which does not exhibit pores, or has pores with an average diameter less than about 2 nm. In embodiments, nonporous nanoparticles have pores with an average diameter of about 1 nm. In embodiments, nonporous nanoparticles have pores, which are not visible by transmission electron microscopy (TEM).

The term "silica nanoparticle" is used according to its plain and ordinary meaning and refers to a nanoparticle containing Si atoms (e.g., in a tetrahedral coordination), typically with 4 oxygen atoms surrounding a central Si atom. A person of ordinary skill in the art would recognize that the silica nanoparticle typically includes terminal oxygen atoms (e.g., the oxygens on the surface of the nanoparticle) that are hydroxyl moieties. A silica nanoparticle is a particle wherein the longest diameter is typically less than or equal to 1000 nanometers comprising a matrix of silicon-oxygen bonds. In embodiments, a nanoparticle has a shortest diameter greater than or equal to 1 nanometer (e.g., diameter from 1 to 1000 nanometers). In embodiments, the silica nanoparticle is mesoporous. In embodiments, the silica nanoparticle is nonporous.

The term "gold nanoparticle" is used according to its plain and ordinary meaning and refers to a nanoparticle containing Au atoms. A gold nanoparticle is a particle wherein the longest diameter is typically less than or equal to 1000 nanometers comprising a matrix of gold atoms. Typically, gold nanoparticles are g are produced in a liquid by reduction of chloroauric acid (H[AuCl$_4$]). In embodiments, the gold nanoparticle may be functionalized with an organic ligand (e.g., citrate).

The terms "poly(lactic-co-glycolic acid) nanoparticle" or "PLGA nanoparticle" are used according to its plain and ordinary meaning and refers to a nanoparticle containing poly(lactic-co-glycolic acid) polymers. PLGA is a copolymer of poly lactic acid (PLA) and poly glycolic acid (PGA), and has the formula:

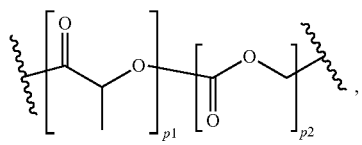

wherein p1 and p2 are each independently integers from 1 to 1000. Depending on the ratio of lactide to glycolide used for the polymerization, different forms of PLGA can be obtained: these are usually identified in regard to the molar ratio of the monomers used (e.g. PLGA 75:25 identifies a copolymer whose composition is 75% lactic acid and 25% glycolic acid). In embodiments the PLGA nanoparticle contains additional polymers (e.g., polyvinyl alcohol, or PEG). In embodiments, the PLGA nanoparticle is 50:50 lactic acid:glycolic acid. In embodiments, the PLGA nanoparticle is 75:25 lactic acid:glycolic acid. n embodiments, the PLGA nanoparticle is 95% PLGA and 5% polyvinyl alcohol (PVA).

The term "iron nanoparticle" is used according to its plain and ordinary meaning and refers to a nanoparticle containing Fe atoms. Iron nanoparticles, including iron oxide nanoparticles, typically contain addition atoms, such as O atom and/or OH. Iron nanoparticles can be synthesized by the reduction of Fe(II) or Fe(III) salt with sodium borohydride in an aqueous solution. In embodiments, the iron nanoparticle includes maghemite ($Fe_2O_3$), magnetite ($Fe_3O_4$), goethite, akaganeite, lepidocrocite, magnetite, or hematite. In embodiments, the iron nanoparticle is magnetic (e.g., superparamagnetic). In embodiments, the iron nanoparticle includes Fe, in combination with O, H, Ni, Co, Zn, Au, N, or C atoms. An iron nanoparticle is a particle wherein the longest diameter is typically less than or equal to 1000 nanometers comprising a matrix of iron-oxygen bonds. In embodiments, the iron nanoparticle is a nanoparticle described in Jacob et al (Iacob M, Racles C, Tugui C, et al. From iron coordination compounds to metal oxide nanoparticles. Sidorenko AS, ed. Beilstein Journal of Nanotechnology. 2016; 7:2074-2087) which is incorporated herein by reference in its entirety. In embodiments, the O/Fe atomic ratio of the iron nanoparticle is 1.50.

A functionalized nanoparticle, as used herein, may refer to the post hoc conjugation (i.e. conjugation after the formation of the nanoparticle) of a moiety to the surface (e.g., terminal hydroxyl moiety, gold atom, oxygen atom) of a nanoparticle. For example, a gold nanoparticle may be further functionalized to include additional atoms (e.g., sulfur) or chemical entities (e.g., sulfur containing polymeric moieties). A functionalized silica nanoparticle, as used herein, may refer to the post hoc conjugation (i.e. conjugation after the formation of the silica nanoparticle) of a moiety to the surface (e.g., terminal hydroxyl moiety) of a nanoparticle. For example, a silica nanoparticle may be further functionalized to include additional atoms (e.g., nitrogen) or chemical entities (e.g., polymeric moieties or bioconjugate group). For example, when the silica nanoparticle is further functionalized with a nitrogen containing compound, one of the surface oxygen atoms surrounding the Si atom may be replaced with a nitrogen containing moiety.

In contrast to a functionalized silica nanoparticle, an unmodified nanoparticle refers to a nanoparticle which has not been further functionalized. Thus, for example, an unmodified silica nanoparticle does not include a nitrogen containing moiety (e.g., terminal amine moieties). For example, an unmodified silica nanoparticle refers to a silica nanoparticle as synthesized without post hoc functionalization. Thus, in embodiments, the unmodified silica nanoparticles includes the following example:

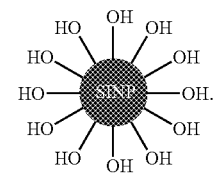

As used herein, the terms "bare silica nanoparticle" and "unmodified silica nanoparticle" are synonymous and interchangeable.

A "detectable agent", "detectable moiety", or "detectable compound" is a composition detectable by spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$CU, $^{64}$Cu, $^{67}$CU, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monocrystalline iron oxide nanoparticles, monocrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition (e.g., a nanoparticle or silica nanoparticle).

Examples of detectable agents include imaging agents, including fluorescent and luminescent substances, including, but not limited to, a variety of organic or inorganic small molecules commonly referred to as "dyes," "labels," or "indicators." Examples include fluorescein, rhodamine, acridine dyes, Alexa dyes, and cyanine dyes. Enzymes that may be used as imaging agents in accordance with the embodiments of the disclosure include, but are not limited to, horseradish peroxidase, alkaline phosphatase, acid phoshatase, glucose oxidase, 3-galactosidase, 3-glucoronidase or p3-lactamase. Such enzymes may be used in combination with a chromogen, a fluorogenic compound or a luminogenic compound to generate a detectable signal.

The term "polymeric" refers to a molecule including repeating subunits (e.g., polymerized monomers). For example, polymeric molecules may be based upon polyethylene glycol (PEG), poly(ethylene glycol)-block-poly(D,L-lactic acid) (PEG-b-PLA), poly[amino(1-oxo-1,6-hexanediyl)], poly(oxy-1,2-ethanediyloxycarbonyl-1,4-phenylenecarbonyl), tetraethylene glycol (TEG), polyvinylpyrrolidone (PVP), poly(xylene), poly(p-xylylene), poly(methyl methacrylate) (PMMA), or poly(lactic-co-glycolic acid) (PLGA). See, for example, "Chemistry of Protein Conjugation and Cross-Linking" Shan S. Wong CRC Press, Boca Raton, Fla., USA, 1993; "BioConjugate Techniques" Greg T. Hermanson Academic Press, San Diego, Calif., USA, 1996; "Catalog of Polyethylene Glycol and Derivatives for Advanced PEGylation, 2004" Nektar Therapeutics Inc, Huntsville, Ala., USA, which are incorporated by reference in their entirety for all purposes.

The term "polymerizable monomer" is used in accordance with its meaning in the art of polymer chemistry and refers to a compound that may covalently bind chemically to other monomer molecules (such as other polymerizable monomers that are the same or different) to form a polymer.

The term "branched polymer" is used in accordance with its meaning in the art of polymer chemistry and refers to a molecule including repeating subunits, wherein at least one repeating subunit (e.g., polymerizable monomer) is covalently bound to an additional subunit substituent (e.g., resulting from a reaction with a polymerizable monomer). For example a branched polymer has the formula:

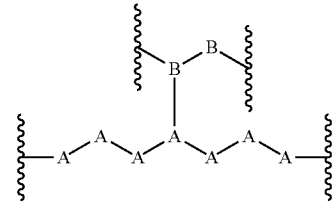

wherein 'A' is the first repeating subunit and 'B' is the second repeating subunit. In embodiments, the first repeating subunit (e.g., polyethylene glycol) is optionally different than the second repeating subunit (e.g., polymethylene glycol).

The term "block copolymer" is used in accordance with its ordinary meaning and refers to two or more portions (e.g., blocks) of polymerized monomers linked by a covalent bond. In embodiments, a block copolymer is a repeating pattern of polymers. In embodiments, the block copolymer includes two or more monomers in a periodic (e.g., repeating pattern) sequence. For example, a diblock copolymer has the formula: -B-B-B-B-B-B-A-A-A-A-A-, where 'B' is a first subunit and 'A' is a second subunit covalently bound together. A triblock copolymer therefore is a copolymer with three distinct blocks, two of which may be the same (e.g., -A-A-A-A-A-B-B-B-B-B-A-A-A-A-A-) or all three are different (e.g., -A-A-A-A-A-B-B-B-B-B-C-C-C-C-C-) where 'A' is a first subunit, 'B' is a second subunit, and 'C' is a third subunit, covalently bound together.

The term "steroid" is used in accordance with its plain ordinary meaning and refers to a class of tetracyclic compounds with, three cyclohexane and one cyclopentane ring arranged with the structural formula:

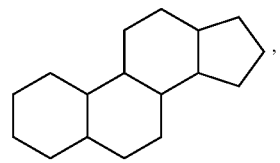 [SMILES: C1CCC2C(C1)CCC1C3CCCC3CCC21]

which is optionally substituted and may include one or more points of non-saturation (i.e. double bonds) within one or more of the rings. Steroids can vary in the number of functional groups or methyl groups attached to the rings, or differ in the level of saturation within the rings. Additional non-limiting examples of steroids include cholesterol, cholic acid, progesterone, testosterone, or estradiol.

A "therapeutic agent" as used herein refers to an agent (e.g., compound or composition) that when administered to a subject in sufficient amounts will have a therapeutic effect, such as an intended prophylactic effect, preventing or delaying the onset (or reoccurrence) of an injury, disease, pathology or condition, or reducing the likelihood of the onset (or reoccurrence) of an injury, disease, pathology, or condition, or their symptoms or the intended therapeutic effect, e.g., treatment or amelioration of an injury, disease, pathology or condition, or their symptoms including any objective or subjective parameter of treatment such as abatement; remission; diminishing of symptoms or making the injury, pathology or condition more tolerable to the patient; slowing in the rate of degeneration or decline; making the final point of degeneration less debilitating; or improving a patient's physical or mental well-being.

The term "immune response" and the like refer, in the usual and customary sense, to a response by an organism that protects against disease or modulates (i.e. increases or decreases relative to a control) the activity of the immune system of a subject. The response can be mounted by the innate immune system or by the adaptive immune system, as well known in the art. The term "modulating an immune response" and the like refer to a change in the immune response of a subject as a consequence of administration of a composition as disclosed herein, including embodiments thereof. The term "modulating" as used herein refers to either increasing or decreasing the level of activity of the modulated entity, e.g., immune response, relative to the level of activity of the modulated entity in the absence of the modulator. Accordingly, an immune response can be activated or deactivated as a consequence of administration (e.g., intraperitoneal administration) of a composition described herein including embodiments thereof. In embodiments, modulating an immune response may be quantified by measuring the presence of a macrophage, or biomarker expressed by a macrophage (e.g., CD45, CD1 b, and/or f4/80). In embodiments, modulating an immune response may be quantified by measuring the presence of CD45 positive cells (e.g., monocytes, dendritic cells, neutrophils, or myeloids expressing the CD45 antigen). In embodiments, modulating an immune response may be quantified by measuring the presence of CD11b positive cells (e.g., monocytes, dendritic cells, neutrophils, or myeloids expressing the CD11b antigen). In embodiments, modulating an immune response may be quantified by measuring the presence of f4-80 positive cells (e.g., monocytes, dendritic cells, neutrophils, or myeloids expressing the f4-80 antigen). In embodiments, increasing an immune response may be quantified by measuring the increased presence of CD45 positive cells (e.g., monocytes, dendritic cells, neutrophils, or myeloids expressing the CD45 antigen), relative to a control. In embodiments, increasing an immune response may be quantified by measuring the increased presence of CD11b positive cells (e.g., monocytes, dendritic cells, neutrophils, or myeloids expressing the CD11b antigen), relative to a control. In embodiments, increasing an immune response may be quantified by measuring the increased presence of f4-80 positive cells (e.g., monocytes, dendritic cells, neutrophils, or myeloids expressing the f4-80 antigen), relative to a control. The immune response can be quantified by measuring: cytokine levels (e.g., IL$\beta$, 12, interferon gamma, IL4, 5, 10, 12, 6, 8, 2, 17, or TNF$\alpha$); the amounts and types of immune cells present; polarization of macrophages (i.e. M1 vs M2, for example measuring the presence of specific biomarkers, such as iNos (for M1) and CD206 (for M2)).

The term "macrophage" is used in accordance with its ordinary meaning and refers to a cell, which is capable of phagocytosis. A macrophage is a relatively long-lived phagocytic cell of mammalian tissues, derived from blood monocytes, and may be static or mobile. Due to differences in receptor expression, cytokine production, and functions, a macrophage may be referred to as M1 or M2. In embodiments, M1 may refer to Type I macrophages; M2 may refer to Type II. M1 macrophages are cells capable of producing pro-inflammatory cytokines and are implicated in the killing of pathogens and tumor cells. M2 macrophages moderate the inflammatory response, eliminate cell wastes, and promote angiogenesis and tissue remodeling (e.g., repair). Non-limited examples of macrophages include adipose tissue macrophages, monocytes, Kupffer cells, sinus histiocytes, alveolar macrophages, tissue macrophages, Langerhans cells, microglia, Hofbauer cells, Intraglomerular mesangial cells, osteoclasts, epithelioid cells, red pulp macrophages, peritoneal macrophages, or Peryer's Patch macrophages. In embodiments the presence of M1 macrophages may be determined by measuring biomarkers for M1, for example CD38, G-protein coupled receptor 18 (Gpr18), Formyl peptide receptor 2 (Fpr2), or iNos. In embodiments the presence of M2 macrophages may be determined by measuring biomarkers for M2, for example Early growth response protein 2 (Egr2), c-Myc, or CD206. Additional biomarkers specific for M1 and M2 may be found in Lisi et al (Neurosci Lett. 2017 Apr. 3; 645:106-112. doi: 10.1016/j.neulet.2017.02.076) or Mignogna et al (Pathol Res Pract. 2016 June; 212(6):491-9. doi: 10.1016/j.prp.2016.02.020) which are incorporated herein by reference, in their entirety.

The terms "nonspherical" or "non-spherical" are used in accordance with their plain ordinary meaning and refers to any shape other than spherical, including for example cubic, pyramidal, oval, plate-like, conical, diamond shaped, and acicular, and including regular and/or irregular shapes. In embodiments, a shape that is at least partially spherical but has portions missing from the sphere is encompassed by the term nonspherical. The term "nonspherical" encompasses a population of clusters of spherical primary nanoparticles (e.g., an aggregate of spherical nanoparticles), wherein the cluster is defined to have any shape other than essentially spherical and is submicron in size. The term "acicular" encompasses shapes such as rods, ellipsoids, needles, and the like. Certain nonspherical shapes have an aspect ratio of at least 2:1, at least 3:1, at least 5:1, or at least 10:1. The term "aspect ratio" refers to the ratio of the average longest dimension (e.g., of a nanoparticle) to the average shortest dimension.

The term "intraperitoneal administration" or "intraperitoneally administering" refers to administration to the peritoneal cavity of a subject (e.g., a mammal, such as a human).

The term "intracellular modulating agent" as used herein refers to an agent (e.g., compound or composition) that, when inside a cell, modulates the activity of the cell. In embodiments, the intracellular modulating agent is a nucleic acid, antibody, polymer, protein, steroid, or a small molecule. In embodiments, the intracellular modulating agent is pro-inflammatory agent. In embodiments, the intracellular modulating agent is imiquimod, resiquimod, or oseltamivir. In embodiments, the intracellular modulating agent is a therapeutic agent. In embodiments, the intracellular modulating agent is an anti-cancer agent.

The term "small molecule" or the like as used herein refers, unless indicated otherwise, to a molecule having a molecular weight of less than about 700 Dalton, e.g., less than about 700, 650, 600, 550, 500, 450, 400, 350, 300, 250, 200, 100, or 50 Dalton.

II. Methods of Use

In an aspect is provided a method of modulating an immune response in a subject in need thereof, the method including intraperitoneally administering a therapeutically effective amount of a nanoparticle composition to the subject. In embodiments, modulating is increasing the immune response. In embodiments, modulating is stimulating the immune response. In embodiments, modulating is relative to a control (also known as a standard control) (e.g., the absence of the nanoparticle composition).

In an aspect is provided a method of modulating an immune response in a subject in need thereof, the method including intraperitoneally administering an effective amount of a nanoparticle composition to the subject.

In embodiments, the nanoparticle composition increases the level or activity of T cells, B cells, or macrophages in a subject. In embodiments, the nanoparticle composition increases the level or activity of T cells. In embodiments, the nanoparticle composition increases the level or activity of B cells in a subject. In embodiments, the nanoparticle composition increases the level or activity of macrophages in a subject. In embodiments, the nanoparticle composition increases the level or activity of tumor associated macrophages in a subject. In embodiments, the nanoparticle composition increases the level or activity of M1 macrophages in a subject. In embodiments, the nanoparticle composition decreases the level or activity of M2 macrophages in a subject.

In embodiments, the nanoparticle composition increases the level of T cells, B cells, or macrophages in a subject. In embodiments, the nanoparticle composition increases the level of T cells in a subject. In embodiments, the nanoparticle composition increases the level of B cells in a subject. In embodiments, the nanoparticle composition increases the level of macrophages in a subject. In embodiments, the nanoparticle composition increases the level of tumor associated macrophages in a subject. In embodiments, the nanoparticle composition increases the level of M1 macrophages in a subject. In embodiments, the nanoparticle composition increases CD45 positive cells (e.g., monocytes, dendritic cells, neutrophils, or myeloids expressing the CD45 antigen). In embodiments, the nanoparticle composition increases CD11b positive cells (e.g., monocytes, dendritic cells, neutrophils, or myeloids expressing the CD11b antigen). In embodiments, the nanoparticle composition increases f4-80 positive cells (e.g., monocytes, dendritic cells, neutrophils, or myeloids expressing the f4-80 antigen). In embodiments, the nanoparticle composition increases CD206 positive cells (e.g., monocytes, dendritic cells, neutrophils, or myeloids expressing the CD206 antigen). In embodiments, the nanoparticle composition increases inducible nitric oxide synthase (iNOS) positive cells (e.g., monocytes, dendritic cells, neutrophils, or myeloids expressing the iNOS antigen).

In embodiments, the nanoparticle composition increases CD45 positive monocytes, CD45 positive dendritic cells, CD45 positive neutrophils, or CD45 positive myeloids, relative to a control in a subject. In embodiments, the nanoparticle composition increases CD45 positive monocytes in a subject. In embodiments, the nanoparticle composition increases CD45 positive dendritic cells in a subject. In embodiments, the nanoparticle composition increases CD45 positive neutrophils in a subject. In embodiments, the nanoparticle composition increases CD45 positive myeloids in a subject. In embodiments, the nanoparticle composition increases CD11b positive monocytes, CD11b positive dendritic cells, CD11b positive neutrophils, or CD11b positive myeloids, relative to a control in a subject. In embodiments, the nanoparticle composition increases CD11b positive monocytes in a subject. In embodiments, the nanoparticle composition increases CD11b positive dendritic cells in a subject. In embodiments, the nanoparticle composition increases CD11b positive neutrophils in a subject. In embodiments, the nanoparticle composition increases CD11b positive myeloids in a subject. In embodiments, the nanoparticle composition increases CD206 positive monocytes, CD206 positive dendritic cells, CD206 positive neutrophils, or CD206 positive myeloids, relative to a control in a subject. In embodiments, the nanoparticle composition increases CD206 positive monocytes in a subject. In embodiments, the nanoparticle composition increases CD206 positive dendritic cells in a subject. In embodiments, the nanoparticle composition increases CD206 positive neutrophils in a subject. In embodiments, the nanoparticle composition increases CD206 positive myeloids in a subject. In embodiments, the nanoparticle composition increases iNOS positive monocytes, iNOS positive dendritic cells, iNOS positive neutrophils, or iNOS positive myeloids, relative to a control in a subject. In embodiments, the nanoparticle composition increases iNOS positive monocytes in a subject. In embodiments, the nanoparticle composition increases iNOS positive dendritic cells in a subject. In embodiments, the nanoparticle composition increases iNOS positive neutrophils in a subject. In embodiments, the nanoparticle composition increases iNOS positive myeloids in a subject.

In embodiments, the nanoparticle composition increases the activity of T cells, B cells, or macrophages in a subject. In embodiments, the nanoparticle composition increases the activity of T cells in a subject. In embodiments, the nanoparticle composition increases the activity of B cells in a subject. In embodiments, the nanoparticle composition increases the activity of macrophages in a subject. In embodiments, the nanoparticle composition increases the activity of tumor associated macrophages in a subject. In embodiments, the nanoparticle composition increases the activity of M1 macrophages in a subject.

In embodiments, the method includes detecting the presence of a biomarker expressed by a macrophage (e.g., CD45, CD11b, iNOS, CD206, and/or f4/80). In embodiments, when increased biomarkers are detected relative to a control, it is indicative of modulating an immune response (e.g., increasing the immune response).

In embodiments, modulating is increasing relative to the absence of the nanoparticle composition. In embodiments, the method includes increasing an immune response to an antigen in a subject in need thereof, the method including intraperitoneally administering an effective amount of a nanoparticle composition to the subject, wherein the increased immune response is an increase relative to the immune response in the absence of the nanoparticle composition. In embodiments, the method includes increasing an immune response to an antigen in a subject in need thereof, the method including intraperitoneally administering of an effective amount a nanoparticle composition to the subject.

In embodiments, the method includes allowing the nanoparticle composition described herein to contact a macrophage.

In embodiments, the method includes increasing phagocytosis of cancer cells by macrophages (e.g., by M1 macrophages). In embodiments, the method includes inducing phagocytosis of cancer cells by macrophages (e.g., by M1 macrophages). In embodiments, the method includes reducing the number of cancer cells in a subject.

In an aspect is provided a method of delivering an intracellular modulating agent to a cell in a subject, the method including intraperitoneally administering an effective amount of to the subject an effective amount of the nanoparticle composition or the pharmaceutical composition as described herein, including embodiments. In embodiments, the nanoparticle is within a macrophage. In embodiments, the macrophage is a tumor associated macrophage (TAM). In embodiments, the macrophage is a M1 or M2 macrophage. In embodiments, the macrophage is a M1 macrophage. In embodiments, the macrophage is a M2 macrophage. In embodiments, the cell is a stomach cell, duodenum cell, jejunum cell, ileum cell, cecum cell, appendix cell, colon cell, liver cell, spleen cell, pancreas cell, or ovarian cell. In embodiments, the cell forms part of a tumor. In embodiments, the tumor is an ovarian tumor, bladder tumor, stomach tumor, pancreatic tumor, colorectal tumor, gastric tumor, bone tumor, spinal tumor, or liver tumor.

In an aspect is provided a method of modulating the activity of a macrophage in a subject, the method including intraperitoneally administering an effective amount of a therapeutically effective amount of a nanoparticle composition to the subject. In embodiments, the method includes contacting the macrophage with an effective amount of the nanoparticle composition. In embodiments, the method increases the activity of the macrophage, relative to the activity of the macrophage in the absence of the nanoparticle composition. In embodiments, the method decreases the activity of the macrophage, relative to the activity of the macrophage in the absence of the nanoparticle composition. In embodiments, the macrophage is in the intraperitoneal cavity. In embodiments, the macrophage is a tumor associated macrophage. In embodiments, the macrophage is an M1 or M2 macrophage. In embodiments, the method increases the level or activity of an M1 macrophage. In embodiments, the method decreases the level or activity of an M2 macrophage.

In another aspect is provided a method of treating a disease, the method including intraperitoneally administering an effective amount of to a subject in need thereof a therapeutically effective amount of a nanoparticle composition or pharmaceutical composition. In embodiments, the disease is a macrophage-associated disease or a cancer of an organ in the intraperitoneal cavity (e.g., stomach, duodenum, jejunum, ileum, cecum, appendix, colon, liver, spleen, pancreas, or ovaries).

In embodiments, the disease is an autoimmune disease, inflammatory disease, or cancer. In embodiments, the disease is oophoritis, endometriosis, or orchitis. In embodiments, the disease is rheumatoid arthritis.

In embodiments, the disease is Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

In embodiments, the disease is traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

In embodiments, the cancer is ovarian cancer, bladder cancer, head and neck cancer, brain cancer, breast cancer, lung cancer, cervical cancer, bone cancer, spinal cancer, liver cancer, colorectal cancer, pancreatic cancer, glioblastoma, neuroblastoma, rhabdomyosarcoma, osteosarcoma, renal cancer, renal cell carcinoma, non-small cell lung cancer, uterine cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, nasopharyngeal cancer, head and neck squamous cell carcinoma, or prostate cancer.

In embodiments, the cancer is ovarian cancer, bladder cancer, head and neck cancer, prostate cancer, brain cancer, breast cancer, lung cancer, cervical cancer, liver cancer, bone cancer, or spinal cancer.

In embodiments, the method further includes allowing the nanoparticle composition to migrate to the site of the disease (e.g., a cancer cell, macrophage, or tumor). In embodiments, the method further includes allowing the nanoparticle composition to migrate to the site of the disease prior to uptake by a cell (e.g., macrophage). The site of the disease (e.g., cancer cell, macrophage, or tumor) is the space (e.g., area or location) proximal to the diseased cell or the diseased cell itself. In embodiments, the site of the diseased cell is the peripheral boundary (e.g., cell membrane or peripheral border cells) of the diseased cell. In embodiments, the site of the diseased cell is cell membrane of the cell. In embodiments, the site of the disease is the peripheral cells at the exterior of the tumor or at the boundary (e.g., border) of the tumor. In embodiments the site of the disease is the location of contact between the nanoparticle composition and the diseased cell. In embodiments, the cell is a plasmacytoid dendritic cell, myeloid dendritic cell, myeloid-derived suppressor cell, granulocytic myeloid-derived suppressor cell, macrophage, B cell, activated NK cell, or activated neutrophil.

In embodiments, the site is proximal to the cancer cell, macrophage, or tumor. In embodiments, the site is about approximately 0.1, 0.2, 0.5, 1, 2, 3, 4, 5, 10, 15, 20, 25, 30, 40, 50, 60, 70, 80, 90, or about 100 nm from the cancer cell, macrophage, or tumor. In embodiments, the site is about 0.1, 0.2, 0.5, 1, 2, 3, 4, 5, 10, 15, 20, 25, 30, 40, 50, 60, 70, 80, 90, or about 100 μm from the cancer cell, macrophage, or tumor. In embodiments, the site is 0.1, 0.2, 0.5, 1, 2, 3, 4, 5, 6, 7, 8, 9, or about 10 mm from the cancer cell, macrophage, or tumor. In embodiments, the site is 0.1, 0.2, 0.5, 1, 2, 3, 4, 5, 6, 7, 8, 9, or about 10 cm from the cancer cell, macrophage, or tumor.

In embodiments, the site of the disease is a cancer cell. In embodiments the site of the disease is a tumor. In embodiments, the site of the disease is a macrophage. In embodiments, the site of the disease is a macrophage proximal to the tumor or cancer cell. In embodiments, the site is a tumor-associated macrophage. In embodiments, where the site of the disease is a macrophage, the macrophage expresses CD45, CD11b, and/or f4/80. In embodiments, the macrophage is a tumor-associated macrophage (e.g., a macrophage located in close proximity to or within a neoplasm). In embodiments, the macrophage is an M1 or M2 macrophage. In embodiments, the macrophage is a M1 macrophage.

In embodiments, the cancer cell forms part of a tumor. In embodiments, the tumor is an ovarian tumor, bladder tumor, pancreatic tumor, colorectal tumor, gastric tumor, bone tumor, spinal tumor, or liver tumor. In embodiments, the tumor is an ovarian tumor. In embodiments, the tumor includes stromal cells, immune cells, proteins, and extracellular matrix generated by stromal or immune cells. In embodiments, the tumor includes macrophage cells. In embodiments, immune cells (e.g., macrophage cells), stromal cells, proteins associate with the immune cells, proteins associated with the stromal cells, and the extracellular matrix generated from immune cells and stromal cells forms part of a tumor.

In an aspect is provided a method of stimulating the immune system of a patient in need thereof including administering an effective amount of a compound described herein (including in an aspect, embodiment, table, figure, claim, sequence listing, or example). In embodiments, the method includes reducing the level suppression of the immune system. In embodiments, the method includes decreasing the level of regulatory cells. In embodiments, the method includes decreasing the level of regulatory T cells. In embodiments, the method includes decreasing the level of suppressor cells. In embodiments, the method includes decreasing the level of suppressor T cells. In embodiments, the method includes decreasing the level of myeloid suppressor cells. In embodiments, the method includes decreasing the level of immune system suppression. In embodiments, the method includes inducing the immune system to recognize disease associated cells (e.g., cancer cells, infected cells).

III. Compositions

In an aspect is provided a nanoparticle composition. In embodiments, the nanoparticle composition is an inorganic nanoparticle, liposome, micelle, or polymeric nanoparticle. In embodiments, the nanoparticle composition is an inorganic nanoparticle (e.g., silica nanoparticle, gold nanoparticle, iron oxide nanoparticle). In embodiments, the nanoparticle is within a macrophage. In embodiments, the nanoparticle composition is a liposome. In embodiments, the nanoparticle composition is an anionic liposome (e.g. a liposome with a quantifiable negative surface charge). In embodiments, the nanoparticle composition is a micelle. In embodiments, the nanoparticle composition is a polymeric nanoparticle (e.g., comprising a plurality of polymers). In embodiments, the nanoparticle composition is non-spherical (e.g., cubic, pyramidal, oval, plate-like, conical, diamond shaped, or acicular).

In embodiments, the nanoparticle composition includes silica, iron, gold, poly(lactic-co-glycolic acid) (PLGA), phospholipid, or polystyrene. In embodiments, the nanoparticle composition includes silica. In embodiments, the nanoparticle composition includes iron (e.g., iron oxide). In embodiments, the nanoparticle composition includes gold. In embodiments, the nanoparticle composition includes poly (lactic-co-glycolic acid) (PLGA). In embodiments, the nanoparticle composition includes poly(lactic-co-glycolic acid) (PLGA) and polyvinyl alcohol. In embodiments, the nanoparticle composition includes polystyrene. In embodiments, the nanoparticle composition is a silica nanoparticle, iron nanoparticle, gold nanoparticle, poly(lactic-co-glycolic acid) (PLGA) nanoparticle, phospholipid nanoparticle, or a polystyrene nanoparticle. In embodiments the nanoparticle composition is functionalized. In embodiments, the nanoparticle composition is unfunctionalized.

In embodiments, the nanoparticle composition is a silica nanoparticle. In embodiments, the nanoparticle composition is a nonporous silica nanoparticle or a mesoporous silica nanoparticle. In embodiments, the nanoparticle composition is a nonporous silica nanoparticle. In embodiments, the nanoparticle composition is a mesoporous silica nanoparticle. In embodiments, the nanoparticle is functionalized. In embodiments, the silica nanoparticle is functionalized (e.g., post-hoc addition of an amino silane).

In embodiments, the silica nanoparticle is an unmodified silica nanoparticle. In embodiments, the silica nanoparticle is a non-polymeric functionalized silica nanoparticle (i.e. a silica nanoparticle that does not include polymers conjugated to the surface of the silica nanoparticle). In embodiments, the silica nanoparticle is a non-pegylated functionalized silica nanoparticle (i.e. a silica nanoparticle that does not include PEG polymers conjugated to the surface of the silica nanoparticle). In embodiments, the silica nanoparticle is a non-functionalized silica nanoparticle (i.e. a silica nanoparticle that does not include reactive chemical functional groups, such as a bioconjugate reactive group, conjugated to the surface of the silica nanoparticle (other than the terminal hydroxyl groups).

In embodiments, the unmodified silica nanoparticle includes terminal oxygen atoms (e.g., the oxygens on the surface of the nanoparticle) that are hydroxyl moieties. In embodiments, the terminal oxygen atoms of the unmodified silica nanoparticle are —OH or salts thereof (e.g. —O⁻ moieties). In embodiments, the terminal oxygen atoms of the unmodified silica nanoparticle may include an —OR" moiety, wherein R" is a substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl or substituted (e.g., substituted with a substituent group, a size-limited substituent group, or lower substituent group) or unsubstituted heteroaryl. In embodiments, about 70%, 80%, 90%, 95%, 99%, or about 100% of the terminal oxygen atoms of the unmodified silica nanoparticle are hydroxyl moieties (or salts thereof). In embodiments, about 70%, 80%, 90%, 95%, 99%, or about 100% of the terminal oxygen atoms of the unmodified silica nanoparticle are hydroxyl moieties (or salts thereof). In embodiments, about 90%, 91%, 92%, 93%, 94%, 95%, 96%, 97%, 98%, 99%, 99.9%, or about 100% of the terminal oxygen atoms of the unmodified silica nanoparticle are hydroxyl moieties (or salts thereof). In embodiments, the unmodified silica nanoparticle includes a covalent bond to an additional chemical moiety (e.g., intracellular modulating agent). In embodiments, the unmodified silica nanoparticle includes a plurality of intracellular modulating agents covalently bound to the unmodified silica nanoparticle. In embodiments, the unmodified silica nanoparticle does not include a covalent bond to an additional chemical moiety. In embodiments, once the unmodified silica nanoparticle has formed, no further chemistry is performed to covalently bond an additional chemical moiety to the surface of the nanoparticle.

In embodiments, the nanoparticle composition is an iron (e.g., iron oxide) nanoparticle. In embodiments, the nanoparticle composition includes maghemite, magnetite, or a combination thereof. In embodiments, the nanoparticle composition is a gold nanoparticle. In embodiments, the nanoparticle composition is a polystyrene nanoparticle. In embodiments, the nanoparticle composition is a poly(lactic-co-glycolic acid) (PLGA) nanoparticle. In embodiments, the nanoparticle composition is not a gold nanoparticle. In embodiments, the nanoparticle composition is not a gold acicular nanoparticle. In embodiments, the nanoparticle composition is poly(lactic-co-glycolic acid) (PLGA) and polyvinyl alcohol (PVA).

In embodiments, the nanoparticle composition includes an iron (e.g., iron oxide) nanoparticle. In embodiments, the nanoparticle composition includes a gold. In embodiments, the nanoparticle composition includes a polystyrene. In embodiments, the nanoparticle composition includes poly (lactic-co-glycolic acid) (PLGA). In embodiments, the nanoparticle composition includes not a gold acicular nanoparticle. In embodiments, the nanoparticle composition includes a poly(lactic-co-glycolic acid) (PLGA) and polyvinyl alcohol (PVA). In embodiments, the nanoparticle composition includes 50:50 PLGA 50:50 (i.e. a copolymer whose composition is 50% lactic acid and 50% glycolic acid). In embodiments, the nanoparticle composition is PLGA 50:50 and polyvinyl alcohol (PVA) nanoparticle. In embodiments, the molecular weight of the PVA is about 30,000 to 70,000 Daltons.

In embodiments, the nanoparticle composition is a phospholipid nanoparticle. In embodiments, the nanoparticle composition includes one or more phospholipids (e.g., dipalmitoylphosphatidylcholine or dipalmitoylphosphatidylglycerol). In embodiments, the nanoparticle composition includes one or more phospholipids comprising phosphatidic acid (e.g., DMPA, DPPA, or DSPA), phosphatidylcholine (e.g., DDPC, DLPC, DMPC, DPPC, DSPC, DOPC, POPC, or DEPC), phosphatidylglycerol (e.g., DMPG, DPPG, DSPG, or POPG), phosphatidylethanolamine (e.g., DMPE, DPPE, DSPE, or DOPE), or phosphatidylserine (e.g., DOPS). In embodiments, the nanoparticle composition is miltilamellar. In embodiments the nanoparticle composition is a combination of phospholipids comprising phosphatidic acid (e.g., DMPA, DPPA, or DSPA), phosphatidylcholine (e.g., DDPC, DLPC, DMPC, DPPC, DSPC, DOPC, POPC, or DEPC), phosphatidylglycerol (e.g., DMPG, DPPG, DSPG, or POPG), phosphatidylethanolamine (e.g., DMPE, DPPE, DSPE, or DOPE), or phosphatidylserine (e.g., DOPS).

In embodiments, the nanoparticle composition includes about 10% of a first phospholipid (e.g., DPPC) and 90% of a second phospholipid (e.g., DPPG). In embodiments, the nanoparticle composition includes about 20% of a first phospholipid (e.g., DPPC) and 80% of a second phospholipid (e.g., DPPG). In embodiments, the nanoparticle composition includes about 30% of a first phospholipid (e.g., DPPC) and 70% of a second phospholipid (e.g., DPPG). In embodiments, the nanoparticle composition includes about 40% of a first phospholipid (e.g., DPPC) and 60% of a second phospholipid (e.g., DPPG). In embodiments, the nanoparticle composition includes about 50% of a first phospholipid (e.g., DPPC) and 50% of a second phospholipid (e.g., DPPG). In embodiments, the nanoparticle composition includes about 60% of a first phospholipid (e.g., DPPC) and 40% of a second phospholipid (e.g., DPPG). In embodiments, the nanoparticle composition includes about 70% of a first phospholipid (e.g., DPPC) and 30% of a second phospholipid (e.g., DPPG). In embodiments, the nanoparticle composition includes about 80% of a first phospholipid (e.g., DPPC) and 20% of a second phospholipid (e.g., DPPG). In embodiments, the nanoparticle composition includes about 90% of a first phospholipid (e.g., DPPC) and 10% of a second phospholipid (e.g., DPPG). In embodiments, the nanoparticle composition includes about 67% of a first phospholipid (e.g., DPPC) and 33% of a second phospholipid (e.g., DPPG). In embodiments, the nanoparticle composition includes about 67% of DPPC and 33% of DPPG.

In embodiments, the nanoparticle composition includes dipalmitoylphosphatidylcholine (DPPC), dipalmitoylphosphatidylglycerol (DPPG), 1,2-didecanoyl-sn-glycero-3-phosphocholine (DDPC), 1,2-Dierucoyl-sn-glycero-3-phosphocholine (DEPC), 1,2-dierucoyl-sn-glycero-3-phosphoethanolamine (DEPE), 1,2-dilinoleoyl-sn-glycero-3-phosphocholine (DLOPC), 1,2-dilauroyl-sn-glycero-3-phosphocholine (DLPC), 1,2-dilauroyl-sn-glycero-3-phosphoethanolamine (DLPE), 1,2-dimyristoyl-sn-glycero-3-phosphocholine (DMPC), 1,2-dimyristoyl-sn-glycero-3-phosphoethanolamine (DMPE), 1,2-dioleoyl-sn-glycero-3-phosphocholine (DOPC), 1,2-dioleoyl-sn-glycero-3-phosphoethanolamine (DOPE), 1,2-dipalmitoyl-sn-glycero-3-phosphoethanolamine (DPPE), 1,2-distearoyl-sn-glycero-3-phosphocholine (DSPC), 1,2-distearoyl-sn-glycero-3-phosphoethanolamine (DSPE), 1-myristoyl-2-stearoyl-sn-glycero-3-phosphocholine (MSPC), 1-palmitoyl-2-myristoyl-sn-glycero-3-phosphocholine (PMPC), 1-Palmitoyl-2-oleoyl-sn-glycero-3-phosphocholine (POPC), 1-palmitoyl-2-oleoyl-sn-glycero-3-phosphoethanolamine (POPE), 1-palmitoyl-2-stearoyl-sn-glycero-3-phosphocholine (PSPC), 1-stearoyl-2-myristoyl-sn-glycero-3-phosphocholine (SMPC), 1-stearoyl-2-oleoyl-sn-glycero-3-phosphocholine (SOPC), or 1-stearoyl-2-palmitoyl-sn-glycero-3-phosphocholine (SPPC).

In embodiments, the nanoparticle composition includes a block copolymer. In embodiments, the nanoparticle composition includes poly(ethylene glycol), poly(ethylene glycol)-block-poly(D,L-lactic acid) (PEG-b-PLA), chitosan, poly(methyl methacrylate) (PMMA), polyvinyl alcohol (PVA), poly(lactic-co-glycolic acid) (PLGA), or a combination thereof. In embodiments, the nanoparticle composition includes poly(ethylene glycol), poly(ethylene glycol)-block-poly(D,L-lactic acid) (PEG-b-PLA), chitosan, poly(methyl methacrylate) (PMMA), polyvinyl alcohol (PVA), or poly(lactic-co-glycolic acid) (PLGA). In embodiments, the nanoparticle composition includes poly(ethylene glycol), poly(ethylene glycol)-block-poly(D,L-lactic acid) (PEG-b-PLA), chitosan, poly(methyl methacrylate) (PMMA), or poly(lactic-co-glycolic acid) (PLGA). In embodiments, the nanoparticle composition includes poly(ethylene glycol). In embodiments, the nanoparticle composition includes poly(ethylene glycol)-block-poly(D,L-lactic acid) (PEG-b-PLA). In embodiments, the nanoparticle composition includes chitosan. In embodiments, the nanoparticle composition includes poly(methyl methacrylate) (PMMA). In embodiments, the nanoparticle composition includes poly(lactic-co-glycolic acid) (PLGA).

In embodiments, the nanoparticle composition includes carboxymethyl chitosan. In embodiments, the nanoparticle composition includes poly(methyl methacrylate) (PMMA) and carboxymethyl chitosan. In embodiments, the nanoparticle composition is a poly(ethylene glycol)-block-poly(D,L-lactic acid) (PEG-b-PLA) micelle. In embodiments, the nanoparticle composition is a poly(lactic-co-glycolic acid) (PLGA) nanoparticle.

In embodiments, the nanoparticle composition has a net negative charge. In embodiments, the nanoparticle composition has a net neutral charge. In embodiments, the nanoparticle composition has a net positive charge. In embodiments, the nanoparticle composition has a net negative or net neutral charge. In embodiments, the nanoparticle composition has a net negative or net neutral charge initially and following post-hoc functionalization the nanoparticle composition has a net neutral or net positive charge. The net charge of the nanoparticle is measured using known techniques in the art (e.g., measuring the Zeta Potential in mV). In embodiments, the Zeta potential of the nanoparticle composition is net negative (e.g., –22 mV). In embodiments, the Zeta potential of the nanoparticle composition is net positive (e.g., 32 mV). In embodiments, the Zeta potential of the nanoparticle composition is net neutral (e.g., about 0 mV).

In embodiments, the nanoparticle composition is bound (e.g., covalently or non-covalently) to an intracellular modulating agent. In embodiments, the nanoparticle is non-covalently bound to the intracellular modulating agent. In embodiments, the nanoparticle is covalently bound to the intracellular modulating agent. In embodiments, the nanoparticle is covalently bound to the intracellular modulating agent via a linker (e.g., a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene). In embodiments, the nanoparticle composition includes a plurality of intracellular modulating agents covalently bound to the nanoparticle composition. In embodiments, the nanoparticle is non-covalently bound to the intracellular modulating agent via a covalent linker, wherein the covalent linker is —S(O)$_2$—, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, the nanoparticle is bound to an intracellular modulating agent, wherein the bond is a non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), or hydrophobic interactions and the like.

In embodiments, the intracellular modulating agent is a nucleic acid, polymer, protein, steroid, or a small molecule. In embodiments, the intracellular modulating agent is a nucleic acid. In embodiments, the intracellular modulating agent is a polymer. In embodiments, the intracellular modulating agent is a protein. In embodiments, the intracellular modulating agent is a steroid (e.g., dexamethasone). In embodiments, the intracellular modulating agent is a small molecule (e.g., less than 900 Daltons, less than 700 Daltons, or less than 500 Daltons). In embodiments, the intracellular modulating agent is a non-natural peptide. In embodiments, the intracellular modulating agent is a cytokine (e.g., chemokine, interferon, interleukin, lymphokine, or tumor necrosis factor). In embodiments, the intracellular modulating agent is an interferon gamma (IFNγ). In embodiments, the nucleic acid is a nucleic acid described herein.

In embodiments, the intracellular modulating agent is a JAK2 inhibitor, STAT3 inhibitor, interferon, CpG oligodeoxynucleotide (CpG ODN), cytotoxic agent, tumor necrosis factor alpha (TNFα), tumor necrosis factor beta (TNFβ), cyclic dinucleotide (e.g., a STING-activating cyclic dinucleotide agonist such as MIW815/ADU-S100), or Granulocyte-macrophage colony-stimulating factor (GM-CSF). In embodiments, the intracellular modulating agent is a JAK2 inhibitor. In embodiments, the intracellular modulating agent is STAT3 inhibitor. In embodiments, the intracellular modulating agent is an interferon. In embodiments, the intracellular modulating agent is CpG oligodeoxynucleotide (CpG ODN). In embodiments, the intracellular modulating agent is cytotoxic agent (e.g., cisplatin, oxaloplatin, carboplatin, or paclitaxel). In embodiments, the intracellular modulating agent is tumor necrosis factor alpha (TNFα). In embodiments, the intracellular modulating agent is tumor necrosis factor beta (TNFβ). In embodiments, the intracellular modulating agent is Granulocyte-macrophage colony-stimulating factor (GM-CSF). In embodiments, the intracellular modulating agent is a cyclic dinucleotide (e.g., a STING-activating cyclic dinucleotide agonist such as MIW815/ADU-S100). In embodiments, the intracellular modulating agent is not a detectable moiety. In embodiments, the intracellular modulating agent is not a platinum containing anti-cancer moiety. In embodiments, the nanoparticle composition does not include a lipid.

In embodiments, the intracellular modulating agent is a therapeutic agent. In embodiments, the intracellular modulating agent is an anti-cancer agent. In embodiments, the intracellular modulating agent is griseofulvin, verapamil, sirolimus, dexmethylphenidate hydrochloride, morphine sulfate, methylphenidate hydrochloride, diltiazem, tizanidine hydrochloride, aprepitant, fenofibrate, nabilone, megestrol acetate, fenofibrate, naproxen sodium, theophylline, paliperidone palmitate, 2-methoxyestradiol, guanylhydrazone, padi taxel, thymectacin, or silver. In embodiments, the intracellular modulating agent is carbamazepine, megestrol acetate, paliperidone palmitate, insulin, ketoprofen, azithromycin, albendazole, tarazepide, griseofulvin, mitotane, cilostazol, aphidicolin, buparvaquone, fenofibrate, cytokine inhibitor, emend, rapamune, probucol, danazol, naproxen, loviride, clofazimine, oridonin, ascorbyl palmitate, dihydroartemisinin, omeprazole, thymectacin, paclitaxel, hydrocortisone, prednisolone, hexadecadrol, budesonide, fluticasone, busulfan, or silver. In embodiments, the intracellular modulating agent is a pro-inflammatory agent (e.g., IL-1 or TNF). In embodiments, the intracellular modulating agent is imiquimod. In embodiments, the intracellular modulating agent is imiquimod, resiquimod, or oseltamivir. In embodiments, the intracellular modulating agent does not contain platinum. In embodiments, the intracellular modulating agent is not cisplatin.

In embodiments, the nanoparticle is a PLGA nanoparticle and the intracellular modulating agent is imiquimod.

In embodiments, the nanoparticle is a PLGA nanoparticle and the intracellular modulating agent is imiquimod, resiquimod, or oseltamivir.

In an aspect is provided a silica nanoparticle non-covalently bound to a plurality of nucleic acids, wherein the silica nanoparticle has a net positive charge in the absence of the plurality of nucleic acids. In embodiments, the nucleic acid is a nucleic acid described herein.

In an aspect is provided a silica nanoparticle non-covalently bound to a plurality of nucleic acids, wherein the silica nanoparticle has a net positive charge prior to binding of the plurality of nucleic acids. The silica nanoparticle may naturally have a net positive charge following synthesis, or may be functionalized with, for example, an aminosilane (e.g., (3-aminopropyl)triethoxysilane), which results in the nanoparticle composition having an overall net positive charge. Following binding of the plurality of nucleic acids, the silica nanoparticle may have a net positive, net negative, or net neutral charge.

In embodiments, the silica nanoparticle is bound to an intracellular modulating agent, wherein the bond is a non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), or hydrophobic interactions and the like. In embodiments, the intracellular modulating agent is a nucleic acid which is non-covalently bound to the nanoparticle composition. In embodiments, the intracellular modulating agent is a nucleic acid which is bound to the nanoparticle composition via non-covalent interactions. In embodiments, the intracellular modulating agent is a nucleic acid which is bound to the nanoparticle composition via electrostatic interactions.

In embodiments, each of the plurality of nucleic acids includes an intracellular modulating agent. In embodiments, each of the plurality of nucleic acids is an intracellular modulating agent. In embodiments, each of the plurality of nucleic acids includes non-coding RNA (ncRNA). In embodiments, each the plurality of nucleic acids includes transfer RNA (tRNA), ribosomal RNA (rRNA), small interfering RNA (siRNA), or microRNA. In embodiments, each of the plurality of nucleic acids includes a TLR-binding nucleic acid substituent conjugated to a STAT-binding DNA substituent. In embodiments, the plurality of nucleic acids is described in Zhang et al (Blood. 2016 Mar. 31; 127(13): 1687-700) and WO 2015/077657, which are incorporated herein in its entirety for all purposes. In embodiments, the is CpG(A)-STAT3dODN having the sequence:

```
                                    (SEQ ID NO: 1)
5' G*G*TGCATCGATGCAGG*G*G*G*G-xxxxx-C*A*T*TTCCCGTA AATC-xxxx-GATTTACGGGAA*A*T*G-xxxxx 3',
``` wherein (*=phosphorothioate linkage), x=is a linker (e.g., a —(CH$_2$)$_3$—) bonded to phosphate groups at both ends

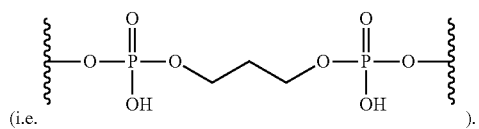 [SMILES: *OP(=O)(O)OCCCOP(=O)(O)O*]

(i.e.                                                                      ).

The 5'x has an OH terminus and 3'x has a —C$_6$—NH$_2$ (e.g., aminohexyl) bonded to the final phosphate group. In embodiments, the linkages are phosphodiester linkers.

In embodiments, each of the plurality of nucleic acids is:

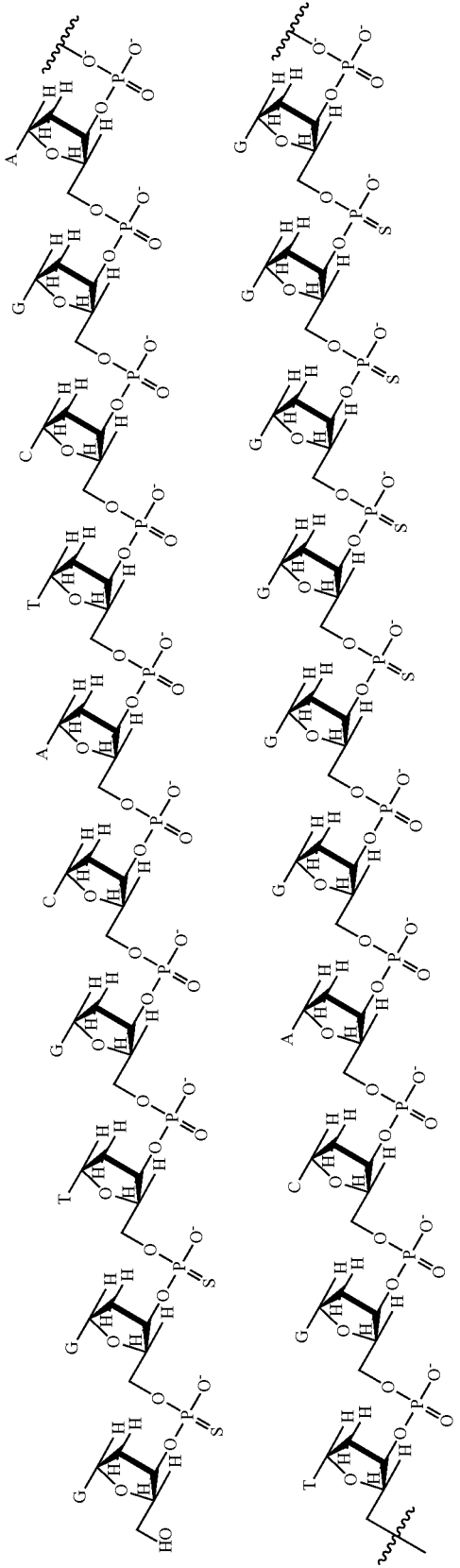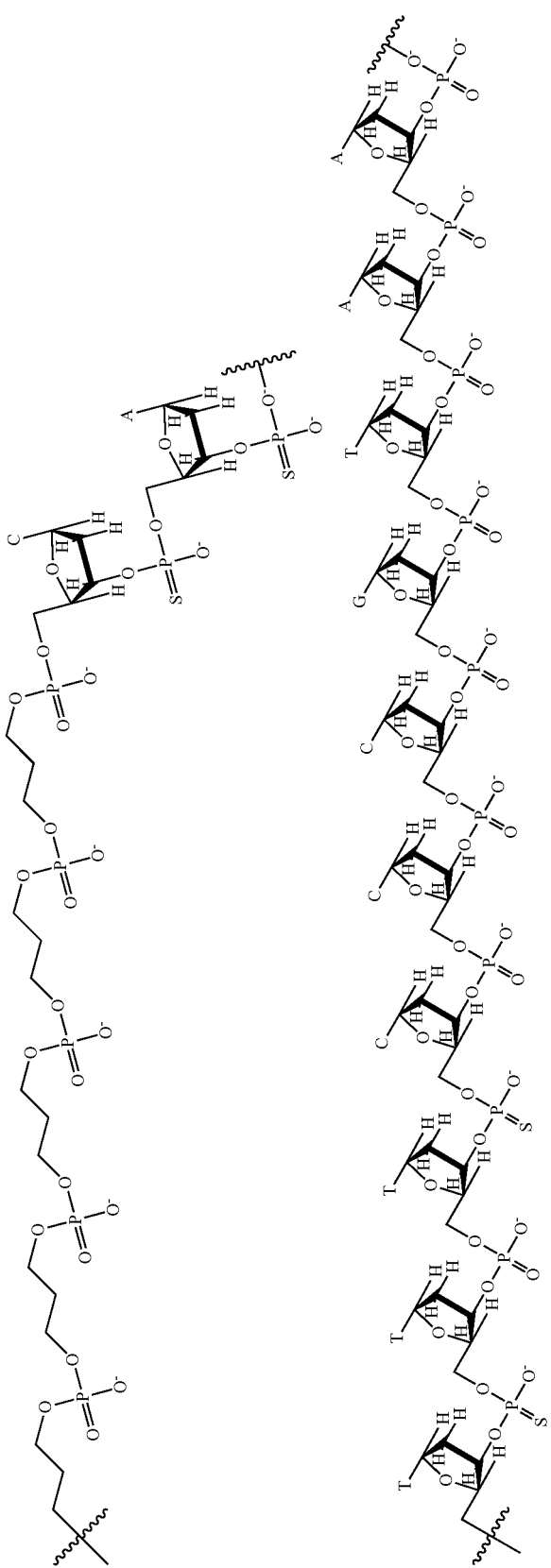

-continued
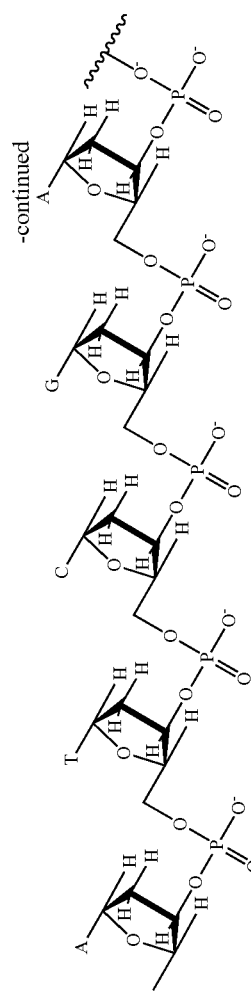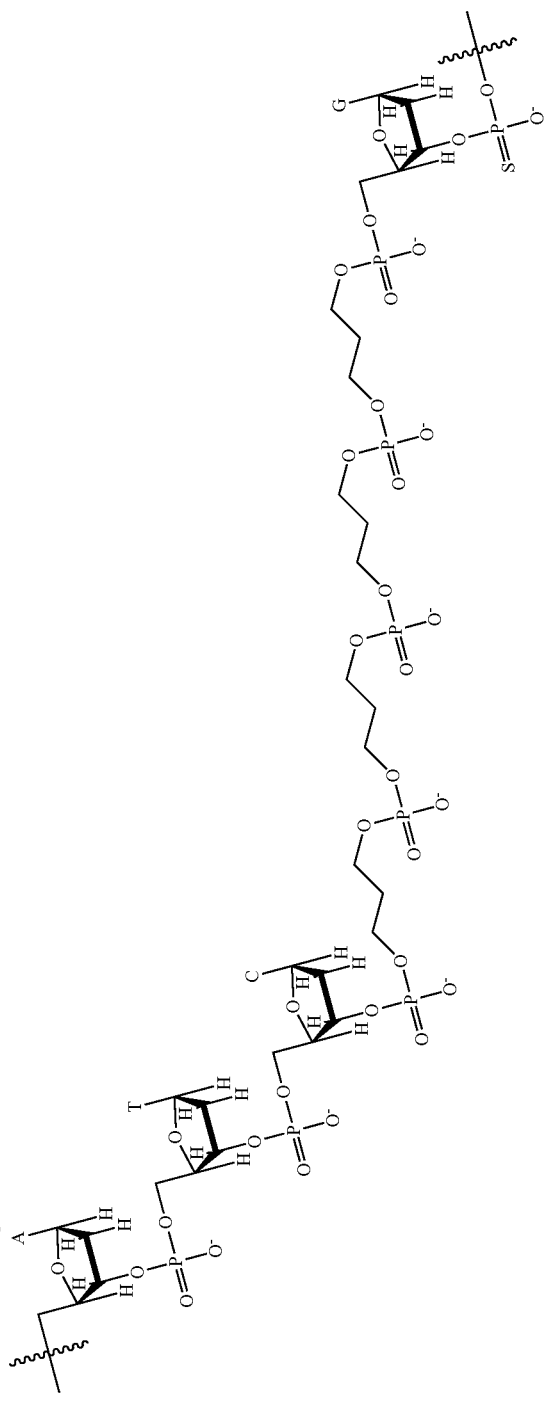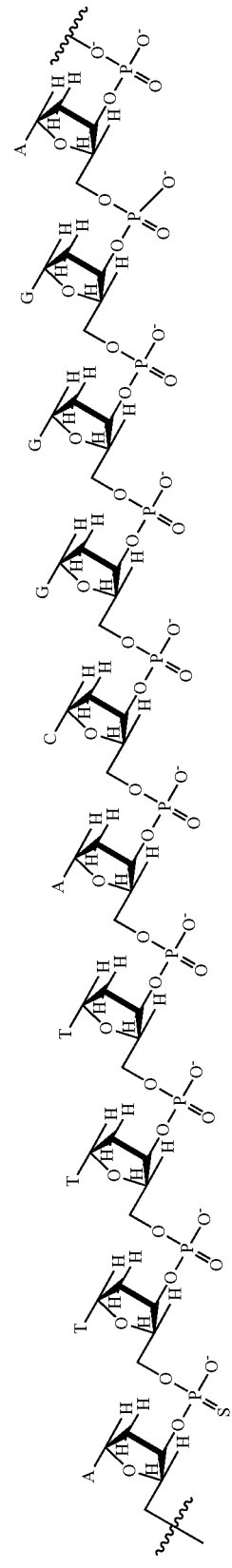

-continued
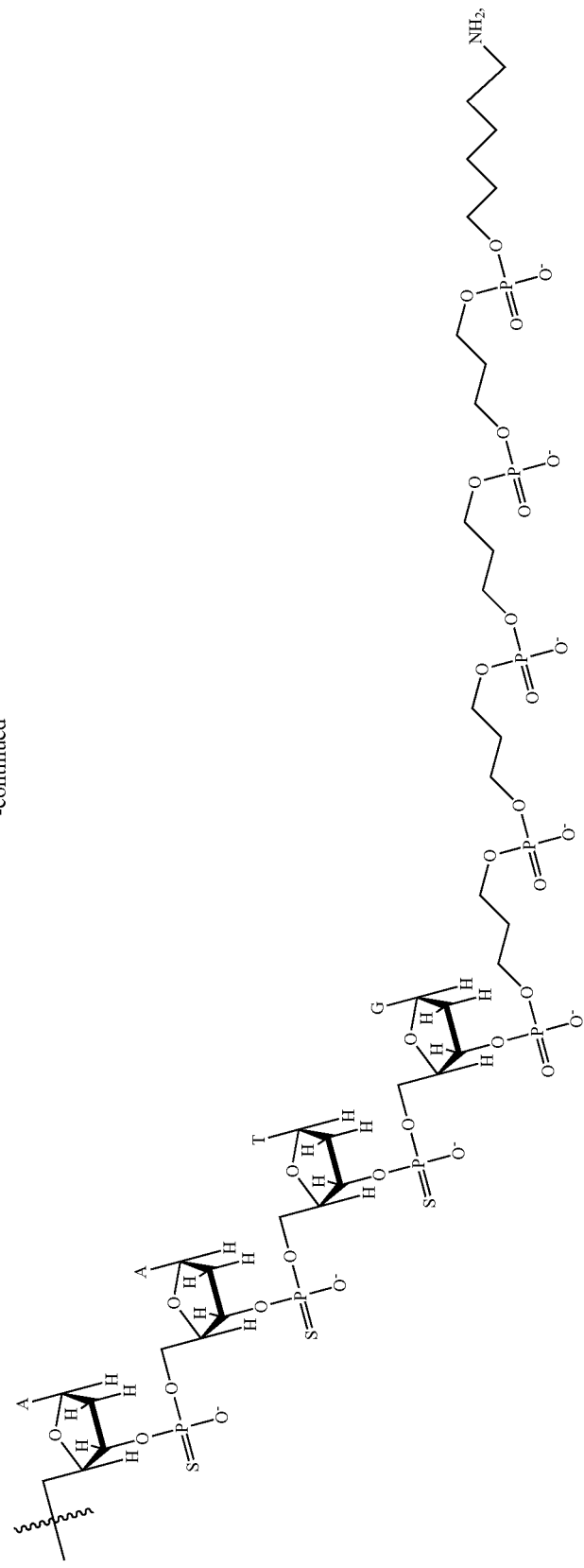

also referred to as (5' G*G*TGCATCGATGCAGG*G*G*G*G-xxxxx-C*A*T*TTCCCGTAAATC-xxxx-GATTTACGGGAA*A*T*G-xxxxx 3' (SEQ ID NO:1), wherein * is a phosphothioate linking group, x is an unsubstituted propyl bonded to phosphate groups at both ends,

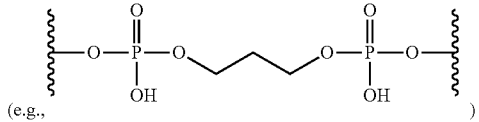 [SMILES: *OP(=O)(O)OCCCOP(=O)(O)O*]

(e.g., )

except for 3' terminal x, which is an unsubstituted hexyl-amino following the final phosphate group

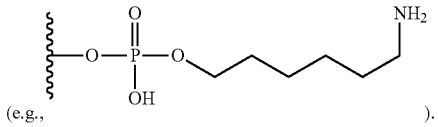 [SMILES: *OP(=O)(O)OCCCCCCN]

(e.g., ).

In embodiments, each of the plurality of nucleic acids is:

```
CpG(A)-STAT3dODN:
                                    (SEQ ID NO: 1)
5' G*G*TGCATCGATGCAGG*G*G*G*G-xxxxx- C*A*T*TTCCCGTAAATC-xxxx-GATTTACGGGAA*A*T*G- xxxxx 3'.
```

In embodiments, each of the plurality of nucleic acids is:

```
GpC(A)-STAT3dODN:
                                    (SEQ ID NO: 2)
5' G*G*TGCATGCATGCAGG*G*G*G*G-xxxxx- C*A*T*TTCCCGTAAATC-xxxx-GATTTACGGGAA*A*T*G- xxxxx 3'
```

In embodiments, each of the plurality of nucleic acids is:

```
CpG(A)-scrambled ODN:
                                    (SEQ ID NO: 3)
5' G*G*TGCATCGATGCAGG*G*G*G*G-xxxxx- A*C*T*CTTGCCAATTAC-xxxx-GTAATTGGCAAG*A*G*T- xxxxx 3'
```

In embodiments, each of the plurality of nucleic acids is:

```
CpG(B)-STAT3dODN:
                                    (SEQ ID NO: 4)
5' T*C*C*A*T*G*A*C*G*T*T*C*C*T*G*A*T*G*C*T-xxxxx- C*A*T*TTCCCGTAAATC-xxxx-GATTTACGGGAA*A*T*G- xxxxx 3'
```

In embodiments, each of the plurality of nucleic acids is:

```
CpG(B)-mutSTAT3dODN:
                                    (SEQ ID NO: 5)
5' T*C*C*A*T*G*A*C*G*T*T*C*C*T*G*A*T*G*C*T- xxxxx-C*A*T*TTCCCTTAAATC-xxxx-GATTTAAGGGAA*A*T*G- xxxxx 3'
```

In embodiments, each of the plurality of nucleic acids is:

```
CpG(B)-scrambled ODN:
                                    (SEQ ID NO: 6)
5' T*C*C*A*T*G*A*C*G*T*T*C*C*T*G*A*T*G*C*T- xxxxx-A*C*T*CTTGCCAATTAC-xxxx-GTAATTGGCAAG*A*G*T- xxxxx 3'
```

In embodiments, each of the plurality of nucleic acids is:

```
STAT3dODN alone:
                                    (SEQ ID NO: 7)
5' xxxxx-C*A*T*TTCCCGTAAATC-xxxx- GATTTACGGGAA*A*T*G-xxxxx 3'
```

In embodiments, each of the plurality of nucleic acids is a nucleic acid described in the Table below:

TABLE 1

Nucleic acid component sequences.

| NAME | SEQUENCE (* = phosphorothioate linkage), x = (—(CH$_2$)$_3$—) bonded to phosphate groups at both ends, 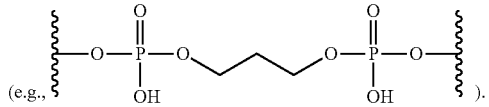 (e.g., ). Terminal phosphates are optionally added and 5'x has an OH terminus and 3'x has a —C$^6$—NH$_2$ bonded to the final phosphate group, other linkages are phosphodiester. |
|---|---|
| CpG(A)-STAT3dODN | 5' G*G*TGCATCGATGCAGG*G*G*G*G-xxxxx-C*A*T*TTCCCGTAAATC-xxxx-GATTTACGGGAA*A*T*G-xxxxx 3' (SEQ ID NO: 1) |
| GpC(A)-STAT3dODN | 5' G*G*TGCATGCATGCAG G*G*G*G*G-xxxxx-C*A*T*TTCCCGTAAATC-xxxx-GATTT ACGGGAA*A*T*G-xxxxx 3' (SEQ ID NO: 2) |

TABLE 1-continued

Nucleic acid component sequences.

SEQUENCE (* = phosphorothioate linkage), x = (—(CH$_2$)$_3$—) bonded to phosphate groups at both ends,

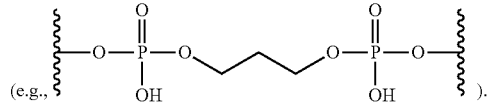 [SMILES: *OP(=O)(O)OCCCOP(=O)(O)O*]

(e.g.,        ).

Terminal phosphates are optionally added and 5'x has an OH terminus and 3'x has a —C$^6$—NH$_2$ bonded to the final phosphate group, other linkages are phosphodiester.

| NAME | |
|---|---|
| CpG(A)-scrambled ODN | 5' G*G*TGCATCGATGCAGG*G*G*G*G-xxxxx-A*C*T*CTTGCCAATTAC-xxxx-GTAAT TGGCAAG*A*G*T-xxxxx 3' (SEQ ID NO: 3) |
| CpG(B)-STAT3dODN | 5' T*C*C*A*T*G*A*C*G*T*T*C*C*T*G*A*T*G*C*T-xxxxx-C*A*T*TTCCCGTAAATC-xxxx-GATTTACGGGAA*A*T*G-xxxxx 3' (SEQ ID NO: 4) |
| CpG(B)-mutSTAT3dODN | 5' T*C*C*A*T*G*A*C*G*T*T*C*C*T*G*A*T*G*C*T-xxxxx-C*A*T*TTCCCTTAAATC-xxxx-GATTTAAGGGAA*A*T*G-xxxxx 3' (SEQ ID NO: 5) |
| CpG(B)-scrambled ODN | 5' T*C*C*A*T*G*A*C*G*T*T*C*C*T*G*A*T*G*C*T-xxxxx-A*C*T*CTTGCCAATTAC-xxxx-GTAATTGGCAAG*A*G*T-xxxxx 3' (SEQ ID NO: 6) |
| STAT3dODN | 5' xxxxx-C*A*T*TTCCCGTAAATC-xxxx-GATTTACGGGAA*A*T*G-xxxxx 3' (SEQ ID NO: 7) |
| ODN 1585 | 5'-G*G*GGTCAACGTTGAG*G*G*G*G-3' (SEQ ID NO: 8)or 5'-G*GGGTCAACGTTGAG*G*G*G*G-3' (SEQ ID NO: 9) |
| ODN 2216 | 5'-G*G*GGGACGATCGTCG*G*G*G*G-3' (SEQ ID NO: 10) or 5'-G*GGGGACGATCGTCG*G*G*G*G-3' (SEQ ID NO: 11) |
| ODN D19 | 5'-G*G*TGCATCGATGCAGG1*G*G*G*G-3' (SEQ ID NO: 12) or 5'-G*GTGCATCGATGCAGG*G*G*G*G-3' (SEQ ID NO: 13) |
| ODN 2336 | 5'-G*G*G*GACGACGTCGTGG*G*G*G*G-3' (SEQ ID NO: 14) or 5'-G*G*GGACGACGTCGTGG*G*G*G*G-3' (SEQ ID NO: 15) |
| ODN 1668 | 5'-T*C*C*A*T*G*A*C*G*T*T*C*C*T*G*A*T*G*C*T-3' (SEQ ID NO: 16) |
| ODN 1826 | 5'- T*C*C*A*T*G*A*C*G*T*T*C*C*T*G*A*C*G*T*T-3' (SEQ ID NO: 17) |
| ODN 2006 (ODN7909) | 5'-T*C*G*T*C*G*T*T*T*T*G*T*C*G*T*T*T*T*G*T*C*G*T*T-3' (SEQ ID NO: 18) |
| ODN 2007 | 5'-T*C*G*T*C*G*T*T*G*T*C*G*T*T*T*T*G*T*C*G*T*T-3' (SEQ ID NO: 19) |
| ODN 2395 | 5'-T*C*G*T*C*G*T*T*T*T*C*G*G*C*G*C*G*C*G*C*C*G-3' (SEQ ID NO: 20) |
| ODN M362 | 5'-T*C*G*T*C*G*T*C*G*T*T*C*G*A*A*C*G*A*C*G*T*T*G*A*T-3' (SEQ ID NO: 21) |

In embodiments, each of the plurality of nucleic acids is SEQ ID NO:1. In embodiments, each of the plurality of nucleic acids is SEQ ID NO:2. In embodiments, each of the plurality of nucleic acids is SEQ ID NO:3. In embodiments, each of the plurality of nucleic acids is SEQ ID NO:4. In embodiments, each of the plurality of nucleic acids is SEQ ID NO:5. In embodiments, each of the plurality of nucleic acids is SEQ ID NO:6. In embodiments, each of the plurality of nucleic acids is SEQ ID NO:7. In embodiments, each of the plurality of nucleic acids is SEQ ID NO:8. In embodiments, each of the plurality of nucleic acids is SEQ ID NO:9. In embodiments, each of the plurality of nucleic acids is SEQ ID NO:10. In embodiments, each of the plurality of nucleic acids is SEQ ID NO:11. In embodiments, each of the plurality of nucleic acids is SEQ ID NO:12. In embodiments, each of the plurality of nucleic acids is SEQ ID NO: 13. In embodiments, each of the plurality of nucleic acids is SEQ ID NO:14. In embodiments, each of the plurality of nucleic acids is SEQ ID NO:15. In embodiments, each of the plurality of nucleic acids is SEQ ID NO:16. In embodiments, each of the plurality of nucleic acids is SEQ ID NO:17. In embodiments, each of the plurality of nucleic acids is SEQ ID NO: 18. In embodiments, each of the plurality of nucleic acids is SEQ ID NO:19. In embodiments, each of the plurality of nucleic acids is SEQ ID NO:20. In embodiments, each of the plurality of nucleic acids is SEQ ID NO:21.

In embodiments, each of the plurality of nucleic acids includes a TLR-binding nucleic acid (e.g. endosomal TLR-, TLR3-, TLR7-, TLR8-, or TLR9-binding nucleic acid) substituent or a STAT-binding DNA substituent (e.g. STAT1-, STAT2-, STAT3-, STAT4-, STAT5A-, STAT5B-, or STAT6-binding DNA substituent). In embodiments, each of the plurality of nucleic acids includes a TLR-binding nucleic acid (e.g. endosomal TLR-, TLR3-, TLR7-, TLR8-, or TLR9-binding nucleic acid). In embodiments, each of the plurality of nucleic acids includes a STAT-binding DNA substituent (e.g. STAT1-, STAT2-, STAT3-, STAT4-, STAT5A-, STAT5B-, or STAT6-binding DNA substituent).

In embodiments, the TLR-binding DNA substituent binds TLR9. In embodiments, the TLR-binding DNA substituent binds TLR3. In embodiments, the TLR-binding DNA substituent preferentially binds TLR9 over other TLR. In embodiments, the TLR-binding DNA substituent specifically binds TLR9. In embodiments, the TLR-binding DNA substituent includes CpG, wherein C and G are nucleotides connected by a phosphodiester internucleotide linkage or phosphodiester derivative internucleotide linkage. In embodiments, the compound includes CpG, wherein C and G are nucleotides connected by a phosphodiester internucleotide linkage. In embodiments, the compound includes CpG, wherein C and G are nucleotides connected by a phosphodiester derivative internucleotide linkage. In embodiments, the CpG is unmethylated. In embodiments, the TLR-binding DNA substituent is a Class A CpG oligodeoxynucleotide (ODN). In embodiments, the TLR-binding DNA substituent is a Class B CpG oligodeoxynucleotide (ODN). In embodiments, the TLR-binding DNA substituent is a Class C CpG oligodeoxynucleotide (ODN). In embodiments, the TLR-binding DNA substituent is ODN 1585, ODN 2216, ODN D19, or ODN 2336. In embodiments, the TLR-binding DNA substituent is ODN 1668, ODN 1826, ODN 2006, or ODN 2007. In embodiments, the TLR-binding DNA substituent is ODN 2395 or ODN M362. In embodiments, the TLR-binding DNA substituent is a derivative of ODN 1585, ODN 2216, ODN D19, ODN 2336, ODN 1668, ODN 1826, ODN 2006, ODN 2007, ODN 2395 or ODN M362. In embodiments, a derivative of ODN 1585, ODN 2216, ODN D19, ODN 2336, ODN 1668, ODN 1826, ODN 2006, ODN 2007, ODN 2395 or ODN M362 includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) nucleotide substitutions (e.g. A, C, G, or T substituted with a different nucleotide). In embodiments, a derivative of ODN 1585, ODN 2216, ODN D19, ODN 2336, ODN 1668, ODN 1826, ODN 2006, ODN 2007, ODN 2395 or ODN M362 includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) internucleotide linkage replacements (e.g. phosphodiester replaced with a phosphodiester derivative or a phosphodiester derivative replaced with a phosphodiester). In embodiments, a derivative of ODN 1585, ODN 2216, ODN D19, ODN 2336, ODN 1668, ODN 1826, ODN 2006, ODN 2007, ODN 2395 or ODN M362 includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) nucleotide deletions. In embodiments, a derivative of ODN 1585, ODN 2216, ODN D19, ODN 2336, ODN 1668, ODN 1826, ODN 2006, ODN 2007, ODN 2395 or ODN M362 includes one or more (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) nucleotide additions.

In embodiments, each of the plurality of nucleic acids includes a TLR-binding nucleic acid (e.g. endosomal TLR-, TLR3-, TLR7-, TLR8-, or TLR9-binding nucleic acid) substituent and a STAT-binding DNA substituent (e.g. STAT1-, STAT2-, STAT3-, STAT4-, STAT5A-, STAT5B-, or STAT6-binding DNA substituent), wherein the STAT binding DNA substituent includes a STAT-binding DNA sequence covalently bonded to a terminal moiety. A terminal moiety is a nucleic acid sequence, DNA sequence, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, the terminal moiety is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, the terminal moiety is a substituted or unsubstituted $C_1$-$C_{40}$ alkyl, substituted or unsubstituted 2 to 40 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, the terminal moiety is a substituted $C_1$-$C_{40}$ alkyl, substituted 2 to 40 membered heteroalkyl, substituted $C_3$-$C_8$ cycloalkyl, substituted 3 to 8 membered heterocycloalkyl, substituted $C_6$-$C_{10}$ aryl, or substituted 5 to 10 membered heteroaryl.

In embodiments, the terminal moiety is a substituted or unsubstituted alkylphosphate terminal moiety having the structure -$L^{1b}$-($PO_4H$-$L^{2b}$)$_{n2}$-H or -$L^{1b}$-($PO_4H$-$L^{2b}$)$_{n2}$—$NH_2$, wherein $L^{1b}$ and $L^{2b}$ are independently a substituted or unsubstituted alkylene (e.g. substituted or unsubstituted $C_1$-$C_{10}$ alkylene). In embodiments, wherein $L^{1b}$ and $L^{2b}$ are independently an unsubstituted alkylene (e.g. unsubstituted $C_1$-$C_{10}$ alkylene). In embodiments, wherein $L^{1b}$ and $L^{2b}$ are unsubstituted $C_3$ alkylene. In embodiments, $L^{1b}$ and $L^{2b}$ are the same. The symbol n2 is an integer from 1 to 500. In embodiments, n2 is an integer from 1 to 400. In embodiments, n2 is an integer from 1 to 300. In embodiments, n2 is an integer from 1 to 200. In embodiments, n2 is an integer from 1 to 100. In embodiments, n2 is an integer from 1 to 50. In embodiments, n2 is an integer from 1 to 25. In embodiments, n2 is an integer from 1 to 10. In embodiments, n2 is an integer from 1 to 5. In embodiments, n2 is an integer from 1 to 4. A person having ordinary skill in the art will recognize that the substituted or unsubstituted alkylphosphate terminal moiety may exist in its salt form, e.g. $L^{1b}$-($PO_4$-$L^{2b}$)$_{n2}$-H. The substituted or unsubstituted alkylphosphate terminal moiety may connect to the 3' phosphate of a nucleic acid as described herein. In embodiments, the terminal moiety is a substituted or unsubstituted alkylphosphate terminal moiety having the structure -$L^{1b}$-($PO_4H$-$L^{2b}$)$_{n2}$-$PO_4H_2$. A person having ordinary skill in the art will recognize that the substituted or unsubstituted alkylphosphate terminal moiety may exist in any of its salt forms, e.g. $L^{1b}$-($PO_4$-$L^{2b}$)$_{n2}$-$PO_{42}$. In embodiments, the terminal moiety is a substituted or unsubstituted $C_1$-$C_{40}$ alkyl, substituted or unsubstituted 2 to 40 membered heteroalkyl, substituted or unsubstituted $C_3$-$C_5$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, the terminal moiety is a substituted or unsubstituted $C_1$-$C_{40}$ alkyl. In embodiments, the terminal moiety is a substituted or unsubstituted 2 to 40 membered heteroalkyl. In embodiments, the terminal moiety is a substituted 2 to 40 membered heteroalkyl. In embodiments, the terminal moiety includes alkyl phosphates (e.g., propyl phosphates). In embodiments, the terminal moiety consists of alkyl phosphates (e.g., propyl phosphates) bonded to the reminder of the compound by phosphates at both ends. In embodiments, the linker terminal moiety consists of 1-6 alkyl phosphates (e.g., propyl phosphates). In embodiments, the terminal moiety consists of 4-6 alkyl phosphates (e.g., propyl phosphates). In embodiments, the terminal moiety consists of 5 alkyl phosphates (e.g., propyl phosphates). In embodiments, the terminal moiety includes a terminal phosphate. In embodiments, the terminal moiety is a —$(CH_2CH_2CH_2-PO_4H)_{n2}$—$CH_2CH_2CH_2CH_2CH_2CH_2NH_2$, wherein n2 is an integer between 1 and 20 (e.g., 1, 2, 3, 4, 5, 6, 7, 8, 9, 10, 11, 12, 13, 14, 15, 16, 17, 18, 19, or 20). In embodiments, the terminal moiety is a —$(CH_2CH_2CH_2-PO_4H)_{n2}$—$CH_2CH_2CH_2CH_2CH_2CH_2NH_2$, wherein n2 is an integer between 1 and 20 (e.g., 1, 2, 3, 4, 5, 6, 7, 8, 9, 10, 11, 12, 13, 14, 15, 16, 17, 18, 19, or 20) wherein the terminal moiety propyl moiety at the terminus is bonded directly to a 3' phosphate moiety. In embodiments, the terminal moiety includes a phosphodiester derivative linkage (e.g., phosphoramidate linkage, phosphorodiamidate linkage, phosphorothioate linkage, phosphorodithioate linkage, phosphonocarboxylic acid linkage, phosphonocarboxylate linkage, phosphonoacetic acid linkage, phosphonoformic acid linkage, methyl phosphonate linkage, boron phosphonate linkage, or O-methylphosphoroamidite linkage). In embodiments, the terminal moiety includes a phosphodiester derivative (e.g., phosphoramidate, phosphorodiamidate, phosphorothioate, phosphorodithioate, phosphonocarboxylic acid, phosphonocarboxylate, phosphonoacetic acid, phosphonoformic acid, methyl phosphonate, boron phosphonate, and O-methylphosphoroamidite).

In embodiments, each of the plurality of nucleic acids includes a linker between the TLR-binding nucleic acid (e.g. endosomal TLR-, TLR3-, TLR7-, TLR8-, or TLR9-binding nucleic acid) substituent and the STAT-binding DNA substituent (e.g. STAT1-, STAT2-, STAT3-, STAT4-, STAT5A-, STAT5B-, or STAT6-binding DNA substituent). In embodiments, the compound includes a linker between the TLR9-binding DNA substituent and the STAT3-binding DNA substituent. In embodiments, the compound includes a linker between the TLR9-binding DNA substituent and the STAT-binding DNA substituent (e.g. STAT1-, STAT2-, STAT3-, STAT4-, STAT5A-, STAT5B-, or STAT6-binding DNA substituent).

A linker is a bond, nucleic acid sequence, two nucleic acid sequences, DNA sequence, two DNA sequences, nucleic acid analog sequence, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, the linker is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, the linker is a substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, the linker is an unsubstituted $C_1$-$C_{20}$ alkylene, unsubstituted 2 to 20 membered heteroalkylene, unsubstituted $C_3$-$C_8$ cycloalkylene, unsubstituted 3 to 8 membered heterocycloalkylene, unsubstituted $C_6$-$C_{10}$ arylene, or unsubstituted 5 to 10 membered heteroarylene. In embodiments, the linker is an unsubstituted $C_1$-$C_{20}$ alkylene. In embodiments, the linker is a substituted or unsubstituted $C_1$-$C_{40}$ alkylene, substituted or unsubstituted 2 to 40 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, the linker is a substituted or unsubstituted $C_1$-$C_{40}$ alkylene. In embodiments, the linker is a substituted or unsubstituted 2 to 40 membered heteroalkylene. In embodiments, the linker is a substituted 2 to 40 membered heteroalkylene. In embodiments, the linker includes alkyl phosphates (e.g., propyl phosphates). In embodiments, the linker consists of alkyl phosphates (e.g., propyl phosphates) bonded to the reminder of the compound by phosphates at both ends. In embodiments, the linker consists of 1-6 alkyl phosphates (e.g., propyl phosphates) bonded to the remainder of the compound by phosphates on both ends. In embodiments, the linker consists of 4-6 alkyl phosphates (e.g., propyl phosphates) bonded to the remainder of the compound by phosphates on both ends. In embodiments, the linker consists of 5 alkyl phosphates (e.g., propyl phosphates) bonded to the remainder of the compound by phosphates on both ends. A person having ordinary skill in the art will recognize that a linker consisting of alkyl phosphates that is bonded to the remainder of the compound by phosphates on both ends will have one more phosphate than alkylene groups (e.g., a linker consisting of 4 alkyl phosphates that is bonded to the reminder of the compound by phosphates at both ends will have five phosphates and four alkyl groups with alternating phosphate groups and alkyl groups).

In embodiments, the linker is a substituted or unsubstituted alkylphosphate linker having the structure -$L^{1a}$-$(PO_4H$-$L^{2a})_{n1}$-, wherein $L^{1a}$ and $L^{2a}$ are independently a substituted or unsubstituted alkylene (e.g. substituted or unsubstituted $C_1$-$C_{10}$ alkylene). In embodiments, wherein $L^{1a}$ and $L^{2a}$ are independently a unsubstituted alkylene (e.g. unsubstituted $C_1$-$C_{10}$ alkylene). In embodiments, wherein $L^{1a}$ and $L^{2a}$ are unsubstituted $C_3$ alkylene. In embodiments, $L^{1a}$ and $L^{2a}$ are the same. The symbol n1 is an integer from 1 to 500. In embodiments, n1 is an integer from 1 to 400. In embodiments, n1 is an integer from 1 to 300. In embodiments, n1 is an integer from 1 to 200. In embodiments, n1 is an integer from 1 to 100. In embodiments, n1 is an integer from 1 to 50. In embodiments, n1 is an integer from 1 to 25. In embodiments, n1 is an integer from 1 to 10. In embodiments, n1 is an integer from 1 to 5. In embodiments, n1 is an integer from 1 to 4. A person having ordinary skill in the art will recognize that the substituted or unsubstituted alkylphosphate linker may exist in its salt form, e.g. $L^{1a}$-$(PO_4^-$-$L^{2a})_{n1}$-. The substituted or unsubstituted alkylphosphate linker may connect the 3' phosphate of a first nucleic acid to a 5' phosphate of a second nucleic acid as described herein. In embodiments, the linker is a —$(CH_2CH_2CH_2-PO_4H)_{n1}$—, wherein n1 is an integer between 1 and 20 (e.g., 1, 2, 3, 4, 5, 6, 7, 8, 9, 10, 11, 12, 13, 14, 15, 16, 17, 18, 19, or 20). In embodiments, the linker is a —$(CH_2CH_2CH_2-PO_4H)_{n1}$—, wherein n1 is an integer between 1 and 20 (e.g., 1, 2, 3, 4, 5, 6, 7, 8, 9, 10, 11, 12, 13, 14, 15, 16, 17, 18, 19, or 20) wherein the terminal linker propyl moiety is bonded directly to a 3' phosphate moiety and the terminal linker phosphate moiety is bonded directly to a 5' carbon of a deoxyribose. In embodiments, the linker includes a phosphodiester derivative linkage (e.g., phosphoramidate linkage, phosphorodiamidate linkage, phosphorothioate linkage, phosphorodithioate linkage, phosphonocarboxylic acid linkage, phosphonocarboxylate linkage, phosphonoacetic acid linkage, phosphonoformic acid linkage, methyl phosphonate linkage, boron phosphonate linkage, or O-methylphosphoroamidite linkage). In embodiments, the linker includes a phosphodiester derivative (e.g., phosphoramidate, phosphorodiamidate, phosphorothioate, phosphorodithioate, phosphonocarboxylic acid, phosphonocarboxylate, phosphonoacetic acid, phosphonoformic acid, methyl phosphonate, boron phosphonate, and O-methylphosphoroamidite).

In embodiments, each of the plurality of nucleic acids includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages). In embodiments, each of the plurality of nucleic acids includes a plurality of phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof). In embodiments, each of the plurality of nucleic acids includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the TLR9-binding DNA substituent. In embodiments, each of the plurality of nucleic acids includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the TLR-binding nucleic acid (e.g. endosomal TLR-, TLR3-, TLR7-, TLR8-, or TLR9-binding nucleic acid) substituent. In embodiments, each of the plurality of nucleic acids includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the STAT3-binding nucleic acid substituent. In embodiments, each of the plurality of nucleic acids includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages), (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof)). In embodiments, each of the plurality of nucleic acids includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the STAT3-binding DNA substituent. In embodiments, each of the plurality of nucleic acids includes a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages) in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphodiester derivative linkage (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite linkages), (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphodiester derivative linkages (e.g., phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite linkages, or combinations thereof)).

In embodiments, the compound includes a phosphorothioate linkage. In embodiments, the compound includes a plurality of phosphorothioate linkages. In embodiments, the compound includes a phosphorothioate linkage in the TLR9-binding DNA substituent. In embodiments, the compound includes a phosphorothioate linkage in the TLR-binding nucleic acid (e.g. endosomal TLR-, TLR3-, TLR7-, TLR8-, or TLR9-binding nucleic acid) substituent. In embodiments, the compound includes a phosphorothioate linkage in the STAT3-binding nucleic acid substituent. In embodiments, the compound includes a phosphorothioate linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphorothioate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorothioate linkages). In embodiments, the compound includes a phosphorothioate linkage in the STAT3-binding DNA substituent. In embodiments, the compound includes a phosphorothioate linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphorothioate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorothioate linkages).

In embodiments, each of the plurality of nucleic acids includes a phosphoramidate linkage. In embodiments, each of the plurality of nucleic acids includes a plurality of phosphoramidate linkages. In embodiments, each of the plurality of nucleic acids includes a phosphoramidate linkage in the TLR9-binding DNA substituent. In embodiments, each of the plurality of nucleic acids includes a phosphoramidate linkage in the TLR-binding nucleic acid (e.g. endosomal TLR-, TLR3-, TLR7-, TLR8-, or TLR9-binding nucleic acid) substituent. In embodiments, each of the plurality of nucleic acids includes a phosphoramidate linkage in the STAT3-binding nucleic acid substituent. In embodiments, each of the plurality of nucleic acids includes a phosphoramidate linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphoramidate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphoramidate linkages). In embodiments, each of the plurality of nucleic acids includes a phosphoramidate linkage in the STAT3-binding DNA substituent. In embodiments, each of the plurality of nucleic acids includes a phosphoramidate linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphoramidate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphoramidate linkages).

In embodiments, each of the plurality of nucleic acids includes a phosphorodiamidate linkage. In embodiments, each of the plurality of nucleic acids includes a plurality of phosphorodiamidate linkages. In embodiments, each of the plurality of nucleic acids includes a phosphorodiamidate linkage in the TLR9-binding DNA substituent. In embodiments, each of the plurality of nucleic acids includes a phosphorodiamidate linkage in the TLR-binding nucleic acid (e.g. endosomal TLR-, TLR3-, TLR7-, TLR8-, or TLR9-binding nucleic acid) substituent. In embodiments, each of the plurality of nucleic acids includes a phosphorodiamidate linkage in the STAT3-binding nucleic acid substituent. In embodiments, each of the plurality of nucleic acids includes a phosphorodiamidate linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphorodiamidate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorodiamidate linkages). In embodiments, each of the plurality of nucleic acids includes a phosphorodiamidate linkage in the STAT3-binding DNA substituent. In embodiments, each of the plurality of nucleic acids includes a phosphorodiamidate linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphorodiamidate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorodiamidate linkages).

In embodiments, each of the plurality of nucleic acids includes a phosphorodithioate linkage. In embodiments, each of the plurality of nucleic acids includes a plurality of phosphorodithioate linkages. In embodiments, each of the plurality of nucleic acids includes a phosphorodithioate linkage in the TLR9-binding DNA substituent. In embodiments, each of the plurality of nucleic acids includes a phosphorodithioate linkage in the TLR-binding nucleic acid (e.g. endosomal TLR-, TLR3-, TLR7-, TLR8-, or TLR9-binding nucleic acid) substituent. In embodiments, each of the plurality of nucleic acids includes a phosphorodithioate linkage in the STAT3-binding nucleic acid substituent. In embodiments, each of the plurality of nucleic acids includes a phosphorodithioate linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphorodithioate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorodithioate linkages). In embodiments, each of the plurality of nucleic acids includes a phosphorodithioate linkage in the STAT3-binding DNA substituent. In embodiments, each of the plurality of nucleic acids includes a phosphorodithioate linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphorodithioate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphorodithioate linkages).

In embodiments, each of the plurality of nucleic acids includes a phosphonocarboxylic acid linkage. In embodiments, each of the plurality of nucleic acids includes a plurality of phosphonocarboxylic acid linkages. In embodiments, each of the plurality of nucleic acids includes a phosphonocarboxylic acid linkage in the TLR9-binding DNA substituent. In embodiments, each of the plurality of nucleic acids includes a phosphonocarboxylic acid linkage in the TLR-binding nucleic acid (e.g. endosomal TLR-, TLR3-, TLR7-, TLR8-, or TLR9-binding nucleic acid) substituent. In embodiments, each of the plurality of nucleic acids includes a phosphonocarboxylic acid linkage in the STAT3-binding nucleic acid substituent. In embodiments, each of the plurality of nucleic acids includes a phosphonocarboxylic acid linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphonocarboxylic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonocarboxylic acid linkages). In embodiments, each of the plurality of nucleic acids includes a phosphonocarboxylic acid linkage in the STAT3-binding DNA substituent. In embodiments, each of the plurality of nucleic acids includes a phosphonocarboxylic acid linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphonocarboxylic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonocarboxylic acid linkages).

In embodiments, each of the plurality of nucleic acids includes a phosphonocarboxylate linkage. In embodiments, each of the plurality of nucleic acids includes a plurality of phosphonocarboxylate linkages. In embodiments, each of the plurality of nucleic acids includes a phosphonocarboxylate linkage in the TLR9-binding DNA substituent. In embodiments, each of the plurality of nucleic acids includes a phosphonocarboxylate linkage in the TLR-binding nucleic acid (e.g. endosomal TLR-, TLR3-, TLR7-, TLR8-, or TLR9-binding nucleic acid) substituent. In embodiments, each of the plurality of nucleic acids includes a phosphonocarboxylate linkage in the STAT3-binding nucleic acid substituent. In embodiments, each of the plurality of nucleic acids includes a phosphonocarboxylate linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphonocarboxylate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonocarboxylate linkages). In embodiments, each of the plurality of nucleic acids includes a phosphonocarboxylate linkage in the STAT3-binding DNA substituent. In embodiments, each of the plurality of nucleic acids includes a phosphonocarboxylate linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphonocarboxylate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonocarboxylate linkages).

In embodiments, each of the plurality of nucleic acids includes a phosphonoacetic acid linkage. In embodiments, each of the plurality of nucleic acids includes a plurality of phosphonoacetic acid linkages. In embodiments, each of the plurality of nucleic acids includes a phosphonoacetic acid linkage in the TLR9-binding DNA substituent. In embodiments, each of the plurality of nucleic acids includes a phosphonoacetic acid linkage in the TLR-binding nucleic acid (e.g. endosomal TLR-, TLR3-, TLR7-, TLR8-, or TLR9-binding nucleic acid) substituent. In embodiments, each of the plurality of nucleic acids includes a phosphonoacetic acid linkage in the STAT3-binding nucleic acid substituent. In embodiments, each of the plurality of nucleic acids includes a phosphonoacetic acid linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphonoacetic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonoacetic acid linkages). In embodiments, each of the plurality of nucleic acids includes a phosphonoacetic acid linkage in the STAT3-binding DNA substituent. In embodiments, each of the plurality of nucleic acids includes a phosphonoacetic acid linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphonoacetic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonoacetic acid linkages).

In embodiments, each of the plurality of nucleic acids includes a phosphonoformic acid linkage. In embodiments, each of the plurality of nucleic acids includes a plurality of phosphonoformic acid linkages. In embodiments, each of the plurality of nucleic acids includes a phosphonoformic acid linkage in the TLR9-binding DNA substituent. In embodiments, each of the plurality of nucleic acids includes a phosphonoformic acid linkage in the TLR-binding nucleic acid (e.g. endosomal TLR-, TLR3-, TLR7-, TLR8-, or TLR9-binding nucleic acid) substituent. In embodiments, each of the plurality of nucleic acids includes a phosphonoformic acid linkage in the STAT3-binding nucleic acid substituent. In embodiments, each of the plurality of nucleic acids includes a phosphonoformic acid linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a phosphonoformic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonoformic acid linkages). In embodiments, each of the plurality of nucleic acids includes a phosphonoformic acid linkage in the STAT3-binding DNA substituent. In embodiments, each of the plurality of nucleic acids includes a phosphonoformic acid linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a phosphonoformic acid linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are phosphonoformic acid linkages).

In embodiments, each of the plurality of nucleic acids includes a methyl phosphonate linkage. In embodiments, each of the plurality of nucleic acids includes a plurality of methyl phosphonate linkages. In embodiments, each of the plurality of nucleic acids includes a methyl phosphonate linkage in the TLR9-binding DNA substituent. In embodiments, each of the plurality of nucleic acids includes a methyl phosphonate linkage in the TLR-binding nucleic acid (e.g. endosomal TLR-, TLR3-, TLR7-, TLR8-, or TLR9-binding nucleic acid) substituent. In embodiments, each of the plurality of nucleic acids includes a methyl phosphonate linkage in the STAT3-binding nucleic acid substituent. In embodiments, each of the plurality of nucleic acids includes a methyl phosphonate linkage in the STAT-binding nucleic acid substituent (e.g. STAT1-, STAT2-, STAT3-, STAT4-, STAT5A-, STAT5B-, or STAT6-binding nucleic acid substituent). In embodiments, one or more of the nucleic acid internucleotide linkages in the compound is a methyl phosphonate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are methyl phosphonate linkages). In embodiments, each of the plurality of nucleic acids includes a methyl phosphonate linkage in the STAT3-binding DNA substituent. In embodiments, each of the plurality of nucleic acids includes a methyl phosphonate linkage in the STAT-binding DNA substituent (e.g. STAT1-, STAT2-, STAT3-, STAT4-, STAT5A-, STAT5B-, or STAT6-binding DNA substituent). In embodiments, one or more of the DNA internucleotide linkages in the compound is a methyl phosphonate linkage (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or all internucleotide linkages in the compound are methyl phosphonate linkages).

In embodiments, each of the plurality of nucleic acids includes a TLR-binding nucleic acid (e.g. endosomal TLR-, TLR3-, TLR7-, TLR8-, or TLR9-binding nucleic acid) substituent and a STAT-binding DNA substituent (e.g. STAT1-, STAT2-, STAT3-, STAT4-, STAT5A-, STAT5B-, or STAT6-binding DNA substituent) and a linker, wherein an example of a linker connecting the sugars is shown below:

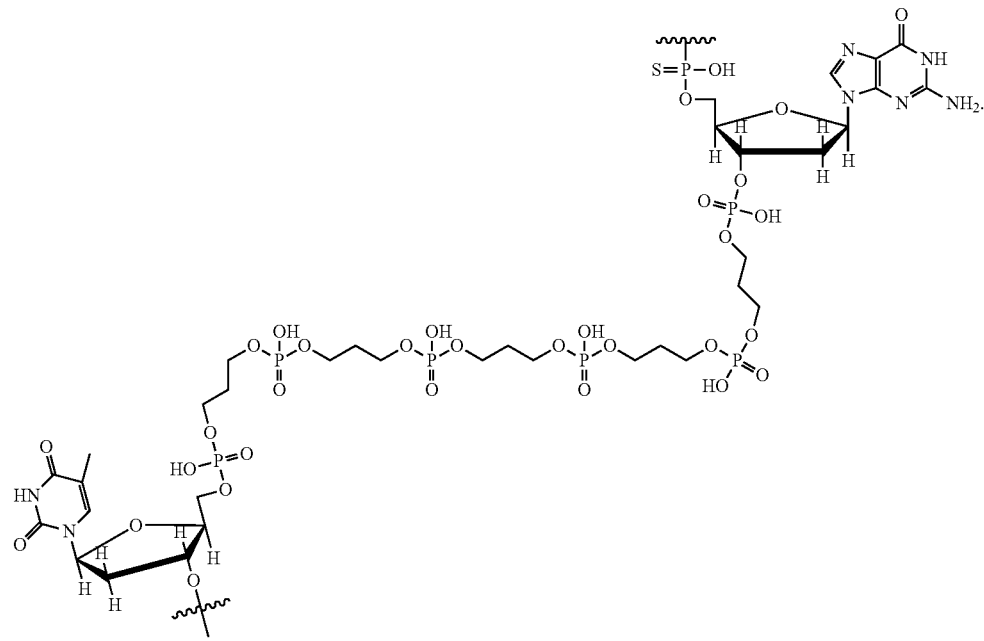

In embodiments, the average longest dimension of the nanoparticle composition is from about 100 nm to about 1000 nm. In embodiments, the average longest dimension of the nanoparticle composition is from about 500 nm to about 1000 nm. In embodiments, the average longest dimension of the nanoparticle composition is from about 100 nm to about 900 nm. In embodiments, the average longest dimension of the nanoparticle composition is from about 100 nm to about 800 nm. In embodiments, the average longest dimension of the nanoparticle composition is from about 200 nm to about 800 nm. In embodiments, the average longest dimension of the nanoparticle composition is from about 100 nm to about 700 nm. In embodiments, the average longest dimension of the nanoparticle composition is from about 100 nm to about 400 nm. In embodiments, the average longest dimension of the nanoparticle composition is from about 200 nm to about 500 nm. In embodiments, the average longest dimension of the nanoparticle composition is from about 300 nm to about 500 nm. In embodiments, the average longest dimension of the nanoparticle composition is from about 500 nm to about 1000 nm. In embodiments, the average longest dimension of the nanoparticle composition is from about 400 nm to about 800 nm. In embodiments, the average longest dimension of the nanoparticle composition is about 500 nm. In embodiments, the average longest dimension of the nanoparticle composition is greater than 500 nm. In embodiments, the average longest dimension of the nanoparticle composition is from about 200 nm to about 250 nm. In embodiments, the average longest dimension of the nanoparticle composition is from about 400 nm to about 600 nm. In embodiments, the average longest dimension of the nanoparticle composition is from about 470 nm to about 530 nm. In embodiments, the average longest dimension of the nanoparticle composition is greater than about 200 nm and less than about 1000 nm.

In embodiments, the average longest dimension of the nanoparticle composition is from about 100 nm to about 600 nm. In embodiments, the average longest dimension of the nanoparticle composition is from about 300 nm, 305 nm, 310 nm, 315 nm, 320 nm, 325 nm, 330 nm, 335 nm, 340 nm, 345 nm, 350 nm, 355 nm, 360 nm, 365 nm, 370 nm, 375 nm, 380 nm, 385 nm, 390 nm, 395 nm, or 400 nm. In embodiments, the average longest dimension of the nanoparticle composition is about 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, 520 nm, 525 nm, 530 nm, 535 nm, 540 nm, 545 nm, 550 nm, 555 nm, 560 nm, 565 nm, 570 nm, 575 nm, 580 nm, 585 nm, 590 nm, 595 nm, or 600 nm. In embodiments, the average longest dimension of the nanoparticle composition is from about 600 nm, 605 nm, 610 nm, 615 nm, 620 nm, 625 nm, 630 nm, 635 nm, 640 nm, 645 nm, 650 nm, 655 nm, 660 nm, 665 nm, 670 nm, 675 nm, 680 nm, 685 nm, 690 nm, 695 nm, 700 nm, 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, 900 nm, 905 nm, 910 nm, 915 nm, 920 nm, 925 nm, 930 nm, 935 nm, 940 nm, 945 nm, 950 nm, 955 nm, 960 nm, 965 nm, 970 nm, 975 nm, 980 nm, 985 nm, 990 nm, 995 nm or about 1000 nm.

In embodiments, the average longest dimension of the nanoparticle composition is less than about 1000 nm. In embodiments, the average longest dimension of the nanoparticle composition is less than about 900 nm. In embodiments, the average longest dimension of the nanoparticle composition is less than about 800 nm. In embodiments, the average longest dimension of the nanoparticle composition is less than about 700 nm. In embodiments, the average longest dimension of the nanoparticle composition is less than about 600 nm. In embodiments, the average longest dimension of the nanoparticle composition is less than about 500 nm. In embodiments, the average longest dimension of the nanoparticle composition is less than about 400 nm. In embodiments, the average longest dimension of the nanoparticle composition is less than about 300 nm. In embodiments, the average longest dimension of the nanoparticle composition is less than about 200 nm. In embodiments, the average longest dimension of the nanoparticle composition is less than about 100 nm.

In embodiments, the average longest dimension of the nanoparticle composition is less than 1000 nm. In embodiments, the average longest dimension of the nanoparticle composition is less than 900 nm. In embodiments, the average longest dimension of the nanoparticle composition is less than 800 nm. In embodiments, the average longest dimension of the nanoparticle composition is less than 700 nm. In embodiments, the average longest dimension of the nanoparticle composition is less than 600 nm. In embodiments, the average longest dimension of the nanoparticle composition is less than 500 nm. In embodiments, the average longest dimension of the nanoparticle composition is less than 400 nm. In embodiments, the average longest dimension of the nanoparticle composition is less than 300 nm. In embodiments, the average longest dimension of the nanoparticle composition is less than 200 nm. In embodiments, the average longest dimension of the nanoparticle composition is less than 100 nm.

In embodiments, the mass ratio of intracellular modulating agent to nanoparticle composition is about 1 to 1. In embodiments, the mass ratio of intracellular modulating agent to nanoparticle composition is about 1 to 2. In embodiments, the mass ratio of intracellular modulating agent to nanoparticle composition is about 1 to 2.5. In embodiments, the mass ratio of intracellular modulating agent to nanoparticle composition is about 1 to 3. In embodiments, the mass ratio of intracellular modulating agent to nanoparticle composition is about 1 to 4. In embodiments, the mass ratio of intracellular modulating agent to nanoparticle composition is about 1 to 5. In embodiments, the mass ratio of intracellular modulating agent to nanoparticle composition is about 1 to 6. In embodiments, the mass ratio of intracellular modulating agent to nanoparticle composition is about 1 to 7. In embodiments, the mass ratio of intracellular modulating agent to nanoparticle composition is about 1 to 8. In embodiments, the mass ratio of intracellular modulating agent to nanoparticle composition is about 1 to 9. In embodiments, the mass ratio of intracellular modulating agent to nanoparticle composition is about 1 to 10. In embodiments, the mass ratio of intracellular modulating agent to nanoparticle composition is about 1 to 11. In embodiments, the mass ratio of intracellular modulating agent to nanoparticle composition is about 1 to 12. In embodiments, the mass ratio of intracellular modulating agent to nanoparticle composition is about 1 to 13. In embodiments, the mass ratio of intracellular modulating agent to nanoparticle composition is about 1 to 14. In embodiments, the mass ratio of intracellular modulating agent to nanoparticle composition is about 1 to 15. In embodiments, the mass ratio of intracellular modulating agent to nanoparticle composition is about 1 to 16. In embodiments, the mass ratio of intracellular modulating agent to nanoparticle composition is about 1 to 17. In embodiments, the mass ratio of intracellular modulating agent to nanoparticle composition is about 1 to 18. In embodiments, the mass ratio of intracellular modulating agent to nanoparticle composition is about 1 to 19. In embodiments, the mass ratio of intracellular modulating agent to nanoparticle composition is about 1 to 20.

In embodiments, the mass ratio of intracellular modulating agent to nanoparticle composition is about 1 to 100. In embodiments, the mass ratio of intracellular modulating agent to nanoparticle composition is about 1 to 200. In embodiments, the mass ratio of intracellular modulating agent to nanoparticle composition is about 1 to 250. In embodiments, the mass ratio of intracellular modulating agent to nanoparticle composition is about 1 to 300. In embodiments, the mass ratio of intracellular modulating agent to nanoparticle composition is about 1 to 400. In embodiments, the mass ratio of intracellular modulating agent to nanoparticle composition is about 1 to 500. In embodiments, the mass ratio of intracellular modulating agent to nanoparticle composition is about 1 to 600. In embodiments, the mass ratio of intracellular modulating agent to nanoparticle composition is about 1 to 700. In embodiments, the mass ratio of intracellular modulating agent to nanoparticle composition is about 1 to 800. In embodiments, the mass ratio of intracellular modulating agent to nanoparticle composition is about 1 to 900. In embodiments, the mass ratio of intracellular modulating agent to nanoparticle composition is about 1 to 1000. In embodiments, the mass ratio of intracellular modulating agent to nanoparticle composition is about 1 to 1100. In embodiments, the mass ratio of intracellular modulating agent to nanoparticle composition is about 1 to 1200. In embodiments, the mass ratio of intracellular modulating agent to nanoparticle composition is about 1 to 1300. In embodiments, the mass ratio of intracellular modulating agent to nanoparticle composition is about 1 to 1400. In embodiments, the mass ratio of intracellular modulating agent to nanoparticle composition is about 1 to 1500. In embodiments, the mass ratio of intracellular modulating agent to nanoparticle composition is about 1 to 1600. In embodiments, the mass ratio of intracellular modulating agent to nanoparticle composition is about 1 to 1700. In embodiments, the mass ratio of intracellular modulating agent to nanoparticle composition is about 1 to 1800. In embodiments, the mass ratio of intracellular modulating agent to nanoparticle composition is about 1 to 1900. In embodiments, the mass ratio of intracellular modulating agent to nanoparticle composition is about 1 to 2000.

In embodiments, the aspect ratio (i.e., the width divided by the length) of the nanoparticle composition is about 0.2, 0.3, 0.4, 0.5, 0.6, 0.7, 0.8, 0.9, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, or about 1.0.

In embodiments, the nanoparticle includes about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 99.9 wt % of the intracellular modulating agent.

In embodiments, the nanoparticle composition enters a cell following administration (e.g. to a patient, to the blood stream of a patient, or to the extracellular milieu of the cell) in about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 minutes, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 hours. In embodiments, the nanoparticle composition enters a cell following administration (e.g. to a patient, to the blood stream of a patient, or to the extracellular milieu of the cell) in less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 minutes, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 hours. In embodiments, the nanoparticle composition enters a cell following administration (e.g. to a patient, to the blood stream of a patient, or to the extracellular milieu of the cell) without co-administration of an agent to facilitate transfection (e.g. an agent with the sole purpose of assisting the compound to enter a cell). In embodiments, the cell is a plasmacytoid dendritic cell, myeloid dendritic cell, myeloid-derived suppressor cell, granulocytic myeloid-derived suppressor cell, macrophage, B cell, activated NK cell, or activated neutrophil.

In embodiments, the nanoparticle composition is not degraded (e.g. in a patient, in the blood stream, at the site of administration, or in the extracellular milieu) for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 minutes, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 hours. In embodiments, the nanoparticle composition is not degraded (e.g. in a patient, in the blood stream, at the site of administration, or in the extracellular milieu) for an average of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 minutes, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 hours. In embodiments, the nanoparticle composition is not degraded (e.g. in a patient, in the blood stream, at the site of administration, or in the extracellular milieu) for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 minutes, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 hours.

In embodiments, the nanoparticle composition includes components described herein, including embodiments, claims, examples, tables, or figures.

IV. Pharmaceutical Compositions

In another aspect, is provided a pharmaceutical composition including a nanoparticle composition as described herein, and a pharmaceutically acceptable excipient. In embodiments, the nanoparticle composition forms part of a pharmaceutical composition, wherein the pharmaceutical composition includes the nanoparticle composition and a pharmaceutically acceptable excipient. In embodiments, the pharmaceutical composition includes a macrophage or an intracellular modulating agent.

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease (e.g., a macrophage-associated disease or a cancer of an organ in the intraperitoneal cavity), such compositions will contain an amount of active ingredient effective to achieve the desired result, e.g., modulating the activity of a target molecule, and/or reducing, eliminating, or slowing the progression of cancer symptoms. Determination of a therapeutically effective amount of a composition (e.g., nanoparticle composition, pharmaceutical composition, or silica nanoparticle) of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g., a macrophage-associated disease or a cancer of an organ in the intraperitoneal cavity), kind of concurrent treatment, complications from the disease being treated or other health-related problems. Other therapeutic regimens or agents can be used in conjunction with the methods and compositions (e.g., nanoparticle composition, pharmaceutical composition, or silica nanoparticle) described herein. Adjustment and manipulation of established dosages (e.g., frequency and duration) are well within the ability of those skilled in the art.

The ratio between toxicity and therapeutic effect for a particular compositions (e.g., nanoparticle composition, pharmaceutical composition, or silica nanoparticle) is its therapeutic index and can be expressed as the ratio between $LD_{50}$ (the amount of compositions (e.g., nanoparticle composition, pharmaceutical composition, or silica nanoparticle) lethal in 50% of the population) and $ED_{50}$ (the amount of compositions (e.g., nanoparticle composition, pharmaceutical composition, or silica nanoparticle) effective in 50% of the population). Compositions (e.g., nanoparticle composition, pharmaceutical composition, or silica nanoparticle) that exhibit high therapeutic indices are preferred. Therapeutic index data obtained from cell culture assays and/or animal studies can be used in formulating a range of dosages for use in humans. The dosage of such compositions (e.g., nanoparticle composition, pharmaceutical composition, or silica nanoparticle) preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the composition (e.g., nanoparticle composition, pharmaceutical composition, or silica nanoparticle) is used.

The neutral forms of the compositions (e.g., nanoparticle composition, pharmaceutical composition, or silica nanoparticle) may be regenerated by contacting the salt with a base or acid and isolating the parent compound in the conventional manner. The parent form of the composition (e.g., nanoparticle composition, pharmaceutical composition, or silica nanoparticle) differs from the various salt forms in certain physical properties, such as solubility in polar solvents, but otherwise the salts are equivalent to the parent form of the composition (e.g., nanoparticle composition, pharmaceutical composition, or silica nanoparticle) for the purposes of the present invention.

Certain compositions described herein of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

In another embodiment, the compositions of the present invention are useful for parenteral administration, such as intraperitoneal (IP) administration into a body cavity or lumen of an organ. The formulations for administration will commonly include a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compositions (e.g., nanoparticle composition, pharmaceutical composition, or silica nanoparticle) described herein can be used in combination with one another, with other active agents known to be useful in treating a disease (e.g., a macrophage-associated disease or a cancer of an organ in the intraperitoneal cavity), or with adjunctive agents that may not be effective alone, but may contribute to the efficacy of the active agent.

In embodiments, the nanoparticle composition, pharmaceutical composition, or silica nanoparticles described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), other platinum-based compounds (e.g. cisplatin, oxaloplatin, or carboplatin), and the like.

The nanoparticle composition, pharmaceutical composition, or silica nanoparticle or drugs described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

In a further embodiment, the nanoparticles, cells, or nanoparticle-cell constructs or drugs described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

The pharmaceutical compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

V. Embodiments

Embodiment P1

A method of modulating an immune response in a subject in need thereof, said method comprising intraperitoneally administering a nanoparticle composition to said subject.

Embodiment P2

The method of embodiment P1, wherein the average longest dimension of the nanoparticle composition is from about 100 nm to about 1000 nm.

Embodiment P3

The method of embodiment P1, wherein the average longest dimension of the nanoparticle composition is from about 200 nm to about 800 nm.

Embodiment P4

The method of embodiment P1, wherein the average longest dimension of the nanoparticle composition is about 500 nm.

Embodiment P5

The method of any one of embodiments P1 to P4, wherein the nanoparticle composition has a net negative charge.

Embodiment P6

The method of any one of embodiments P1 to P4, wherein the nanoparticle composition is an inorganic nanoparticle, liposome, micelle, or polymeric nanoparticle.

Embodiment P7

The method of any one of embodiments P1 to P4, wherein the nanoparticle composition comprises silica, iron, gold, poly(lactic-co-glycolic acid) (PLGA), phospholipid, or polystyrene.

Embodiment P8

The method of any one of embodiments P1 to P4, wherein the nanoparticle composition is a nonporous silica nanoparticle or a mesoporous silica nanoparticle.

Embodiment P9

The method of any one of embodiments P1 to P4, wherein the nanoparticle composition comprises a block copolymer.

Embodiment P10

The method of any one of embodiments P1 to P4, wherein the nanoparticle composition comprises poly(ethylene glycol), poly(ethylene glycol)-block-poly(D,L-lactic acid) (PEG-b-PLA), chitosan, poly(methyl methacrylate) (PMMA), or poly(lactic-co-glycolic acid) (PLGA).

Embodiment P11

The method of any one of embodiments P1 to P10, wherein the nanoparticle composition is non-spherical.

Embodiment P12

The method of any one of embodiments P1 to P11, wherein the nanoparticle composition is bound to an intracellular modulating agent.

Embodiment P13

The method of embodiment P12, wherein the nanoparticle is non-covalently bound to said intracellular modulating agent.

Embodiment P14

The method of embodiments P12 or P13, wherein said intracellular modulating agent is a nucleic acid, polymer, protein, steroid, or a small molecule.

Embodiment P15

The method of embodiments P12 or P13, wherein said intracellular modulating agent is a non-natural peptide.

Embodiment P16

The method of embodiments P12 or P13, wherein said intracellular modulating agent is a JAK2 inhibitor, STAT3 inhibitor, interferon, CpG oligodeoxynucleotide (CpG ODN), cytotoxic agent, tumor necrosis factor alpha (TNFα), tumor necrosis factor beta (TNFβ), or Granulocyte-macrophage colony-stimulating factor (GM-CSF).

Embodiment P17

The method of any one of embodiments P1 to P16, wherein the nanoparticle composition forms part of a pharmaceutical composition, wherein the pharmaceutical composition comprises said nanoparticle composition and a pharmaceutically acceptable excipient.

Embodiment P18

A method of delivering an intracellular modulating agent to a cell in a subject, said method comprising intraperitoneally administering to said subject an effective amount of the nanoparticle composition of any one of embodiments P1 to P16 or the pharmaceutical composition of claim 17.

Embodiment P19

The method of embodiment P18, wherein said nanoparticle is within a macrophage.

Embodiment P20

The method of embodiment P19, wherein said macrophage is a tumor associated macrophage (TAM).

Embodiment P21

A method of modulating the activity of a macrophage in a subject, said method comprising intraperitoneally administering a nanoparticle composition to said subject and contacting the macrophage with an effective amount of said nanoparticle composition.

Embodiment P22

The method of embodiment P21, wherein the average longest dimension of the nanoparticle composition is from about 100 nm to about 1000 nm.

Embodiment P23

The method of embodiment P21, wherein the average longest dimension of the nanoparticle composition is from about 200 nm to about 800 nm.

Embodiment P24

The method of embodiment P21, wherein the average longest dimension of the nanoparticle composition is about 500 nm.

Embodiment P25

The method of any one of embodiments P21 to P24, wherein the nanoparticle composition has a net negative charge.

Embodiment P26

The method of any one of embodiments P21 to P24, wherein the nanoparticle composition is an inorganic nanoparticle, liposome, micelle, or polymeric nanoparticle.

Embodiment P27

The method of any one of embodiments P21 to P24, wherein the nanoparticle composition comprises silica, iron, gold, poly(lactic-co-glycolic acid) (PLGA), phospholipid, or polystyrene.

Embodiment P28

The method of any one of embodiments P21 to P24, wherein the nanoparticle composition is a nonporous silica nanoparticle or a mesoporous silica nanoparticle.

Embodiment P29

The method of any one of embodiments P21 to P24, wherein the nanoparticle composition comprises a block copolymer.

Embodiment P30

The method of any one of embodiments P21 to P24, wherein the nanoparticle composition comprises poly(ethylene glycol), poly(ethylene glycol)-block-poly(D,L-lactic acid) (PEG-b-PLA), chitosan, poly(methyl methacrylate) (PMMA), or poly(lactic-co-glycolic acid) (PLGA).

Embodiment P31

The method of any one of embodiments P21 to P30, wherein the nanoparticle composition is non-spherical.

Embodiment P32

The method of any one of embodiments P21 to P31, wherein the nanoparticle composition is bound to an intracellular modulating agent.

Embodiment P33

The method of embodiment P32, wherein the nanoparticle is non-covalently bound to said intracellular modulating agent.

Embodiment P34

The method of embodiments P32 or P33, wherein said intracellular modulating agent is a nucleic acid, polymer, protein, steroid, or a small molecule.

Embodiment P35

The method of embodiments P32 or P33, wherein said intracellular modulating agent is a non-natural peptide.

Embodiment P36

The method of embodiments P32 or P33, wherein said intracellular modulating agent is a JAK2 inhibitor, STAT3 inhibitor, interferon, CpG oligodeoxynucleotide (CpG ODN), cytotoxic agent, tumor necrosis factor alpha (TNFα), tumor necrosis factor beta (TNFβ), or Granulocyte-macrophage colony-stimulating factor (GM-CSF).

Embodiment P37

The method of any one of embodiments P21 to P36, wherein the nanoparticle composition forms part of a pharmaceutical composition, wherein the pharmaceutical composition comprises said nanoparticle composition and a pharmaceutically acceptable excipient.

Embodiment P38

A method of treating a disease, said method comprising intraperitoneally administering to a subject in need thereof a therapeutically effective amount of a nanoparticle composition.

Embodiment P39

The method of embodiment P38, wherein the average longest dimension of the nanoparticle composition is from about 100 nm to about 1000 nm.

Embodiment P40

The method of embodiment P38, wherein the average longest dimension of the nanoparticle composition is from about 200 nm to about 800 nm.

Embodiment P41

The method of embodiment P38, wherein the average longest dimension of the nanoparticle composition is about 500 nm.

Embodiment P42

The method of any one of embodiments P38 to P41, wherein the nanoparticle composition has a net negative charge.

Embodiment P43

The method of any one of embodiments P38 to P41, wherein the nanoparticle composition is an inorganic nanoparticle, liposome, micelle, or polymeric nanoparticle.

Embodiment P44

The method of any one of embodiments P38 to P41, wherein the nanoparticle composition comprises silica, iron, gold, poly(lactic-co-glycolic acid) (PLGA), phospholipid, or polystyrene.

Embodiment P45

The method of any one of embodiments P38 to P41, wherein the nanoparticle composition is a nonporous silica nanoparticle or a mesoporous silica nanoparticle.

Embodiment P46

The method of any one of embodiments P38 to P41, wherein the nanoparticle composition comprises a block copolymer.

Embodiment P47

The method of any one of embodiments P38 to P41, wherein the nanoparticle composition comprises poly(ethylene glycol), poly(ethylene glycol)-block-poly(D,L-lactic acid) (PEG-b-PLA), chitosan, poly(methyl methacrylate) (PMMA), or poly(lactic-co-glycolic acid) (PLGA).

Embodiment P48

The method of any one of embodiments P38 to P47, wherein the nanoparticle composition is non-spherical.

Embodiment P49

The method of any one of embodiments P38 to P48, wherein the nanoparticle composition is bound to an intracellular modulating agent.

Embodiment P50

The method of embodiment P49, wherein the nanoparticle is non-covalently bound to said intracellular modulating agent.

Embodiment P51

The method of embodiments P49 or P50, wherein said intracellular modulating agent is a nucleic acid, polymer, protein, steroid, or a small molecule.

Embodiment P52

The method of embodiments P49 or P50, wherein said intracellular modulating agent is a non-natural peptide.

Embodiment P53

The method of embodiments P49 or P50, wherein said intracellular modulating agent is a JAK2 inhibitor, STAT3 inhibitor, interferon, CpG oligodeoxynucleotide (CpG ODN), cytotoxic agent, tumor necrosis factor alpha (TNFα), tumor necrosis factor beta (TNFβ), or Granulocyte-macrophage colony-stimulating factor (GM-CSF).

Embodiment P54

The method of any one of embodiments P38 to P53, wherein the nanoparticle composition forms part of a pharmaceutical composition, wherein the pharmaceutical composition comprises said nanoparticle composition and a pharmaceutically acceptable excipient.

Embodiment P55

A silica nanoparticle non-covalently bound to a plurality of nucleic acids, wherein said silica nanoparticle has a net positive charge prior to binding of the plurality of nucleic acids.

Embodiment P56

The nanoparticle of embodiment P55, wherein each of the plurality of nucleic acids comprises an intracellular modulating agent.

Embodiment P57

The nanoparticle of embodiments P55 or P56, wherein each of the plurality of nucleic acids comprises non-coding RNA (ncRNA).

Embodiment P58

The nanoparticle of embodiments P55 or P56, wherein each the plurality of nucleic acids comprises transfer RNA (tRNA), ribosomal RNA (rRNA), small interfering RNA (siRNA), or microRNA.

Embodiment P59

The nanoparticle of embodiments P55 or P56, wherein each of the plurality of nucleic acids comprises a TLR-binding nucleic acid substituent conjugated to a STAT-binding DNA substituent.

Embodiment P60

The nanoparticle of embodiments P55 or P56, wherein each of the plurality of nucleic acids comprises a TLR9-binding DNA substituent conjugated to a STAT3-binding DNA substituent.

Embodiment P61

The nanoparticle of embodiment P60, wherein the STAT3-binding DNA substituent comprises a first STAT3-binding DNA sequence covalently bound to a second STAT3-binding DNA sequence by a linker; and said linker is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

VI. Additional Embodiments

Embodiment 1

A method of modulating an immune response in a subject in need thereof, said method comprising intraperitoneally administering a therapeutically effective amount of a nanoparticle composition to said subject.

Embodiment 2

The method of embodiment 1, wherein the nanoparticle composition increases the level or activity of T cells, B cells, or macrophages.

Embodiment 3

The method of embodiment 1, wherein the nanoparticle composition increases the level or activity of M1 macrophages.

Embodiment 4

The method of any one of embodiments 1 to 3, wherein the average longest dimension of the nanoparticle composition is from about 200 nm to about 800 nm.

Embodiment 5

The method of any one of embodiments 1 to 3, wherein the average longest dimension of the nanoparticle composition is from about 500 nm to about 1000 nm.

Embodiment 6

The method of any one of embodiments 1 to 3, wherein the average longest dimension of the nanoparticle composition is about 500 nm.

Embodiment 7

The method of any one of embodiments 1 to 6, wherein the nanoparticle composition has a net negative charge.

Embodiment 8

The method of any one of embodiments 1 to 6, wherein the nanoparticle composition is an inorganic nanoparticle, liposome, micelle, or polymeric nanoparticle.

Embodiment 9

The method of any one of embodiments 1 to 6, wherein the nanoparticle composition comprises silica, iron, gold, poly(lactic-co-glycolic acid) (PLGA), phospholipid, or polystyrene.

Embodiment 10

The method of any one of embodiments 1 to 6, wherein the nanoparticle composition is a nonporous silica nanoparticle or a mesoporous silica nanoparticle.

Embodiment 11

The method of any one of embodiments 1 to 6, wherein the nanoparticle composition comprises a block copolymer.

Embodiment 12

The method of any one of embodiments 1 to 6, wherein the nanoparticle composition comprises poly(ethylene glycol), poly(ethylene glycol)-block-poly(D,L-lactic acid) (PEG-b-PLA), chitosan, poly(methyl methacrylate) (PMMA), polyvinyl alcohol (PVA), poly(lactic-co-glycolic acid) (PLGA), or a combination thereof.

Embodiment 13

The method of any one of embodiments 1 to 6, wherein the nanoparticle composition comprises poly(lactic-co-glycolic acid) (PLGA).

Embodiment 14

The method of any one of embodiments 1 to 14, wherein the nanoparticle composition is non-spherical.

Embodiment 15

The method of any one of embodiments 1 to 14, wherein the nanoparticle composition is bound to an intracellular modulating agent.

Embodiment 16

The method of embodiment 15, wherein the nanoparticle is non-covalently bound to said intracellular modulating agent.

Embodiment 17

The method of embodiments 15 or 16, wherein said intracellular modulating agent is a nucleic acid, antibody, polymer, protein, steroid, or a small molecule.

Embodiment 18

The method of embodiments 15 or 16, wherein said intracellular modulating agent is a pro-inflammatory agent.

Embodiment 19

The method of embodiments 15 or 16, wherein said intracellular modulating agent is a JAK2 inhibitor, STAT3 inhibitor, interferon, CpG oligodeoxynucleotide (CpG ODN), cytotoxic agent, tumor necrosis factor alpha (TNFα), tumor necrosis factor beta (TNFβ), cyclic dinucleotide, or Granulocyte-macrophage colony-stimulating factor (GM-CSF).

Embodiment 20

The method of embodiments 15 or 16, wherein the intracellular modulating agent is imiquimod, resiquimod, or oseltamivir.

Embodiment 21

The method of embodiment 13, wherein the intracellular modulating agent is imiquimod.

Embodiment 22

A method of modulating the activity of a macrophage in a subject, said method comprising intraperitoneally administering a therapeutically effective amount of a nanoparticle composition to said subject.

Embodiment 23

The method of embodiment 22, wherein the macrophage is a tumor associated macrophage.

Embodiment 24

The method of embodiment 22, wherein the macrophage is an M1 or M2 macrophage.

Embodiment 25

The method of embodiment 22, wherein the method increases the level or activity of an M1 macrophage.

Embodiment 26

The method of embodiment 22, wherein the method decreases the level or activity of an M2 macrophage.

Embodiment 27

The method of any one of embodiments 22 to 26, wherein the average longest dimension of the nanoparticle composition is from about 200 nm to about 800 nm.

Embodiment 28

The method of any one of embodiments 22 to 26, wherein the average longest dimension of the nanoparticle composition is about 500 nm.

Embodiment 29

The method of any one of embodiments 22 to 28, wherein the nanoparticle composition has a net negative charge.

Embodiment 30

The method of any one of embodiments 22 to 28, wherein the nanoparticle composition is an inorganic nanoparticle, liposome, micelle, or polymeric nanoparticle.

Embodiment 31

The method of any one of embodiments 22 to 28, wherein the nanoparticle composition comprises silica, iron, gold, poly(lactic-co-glycolic acid) (PLGA), phospholipid, or polystyrene.

Embodiment 32

The method of any one of embodiments 22 to 28, wherein the nanoparticle composition is a nonporous silica nanoparticle or a mesoporous silica nanoparticle.

Embodiment 33

The method of any one of embodiments 22 to 28, wherein the nanoparticle composition comprises a block copolymer.

Embodiment 34

The method of any one of embodiments 22 to 28, wherein the nanoparticle composition comprises poly(ethylene glycol), poly(ethylene glycol)-block-poly(D,L-lactic acid) (PEG-b-PLA), chitosan, poly(methyl methacrylate) (PMMA), polyvinyl alcohol (PVA), poly(lactic-co-glycolic acid) (PLGA), or a combination thereof.

Embodiment 35

The method of any one of embodiments 22 to 28, wherein the nanoparticle composition comprises poly(lactic-co-glycolic acid) (PLGA).

Embodiment 36

The method of any one of embodiments 22 to 34, wherein the nanoparticle composition is non-spherical.

Embodiment 37

The method of any one of embodiments 22 to 36, wherein the nanoparticle composition is bound to an intracellular modulating agent.

Embodiment 38

The method of embodiment 37, wherein the nanoparticle is non-covalently bound to said intracellular modulating agent.

Embodiment 39

The method of embodiments 37 or 38, wherein said intracellular modulating agent is a nucleic acid, antibody, polymer, protein, steroid, or a small molecule.

Embodiment 40

The method of embodiments 37 or 38, wherein said intracellular modulating agent is a pro-inflammatory agent.

Embodiment 41

The method of embodiments 37 or 38, wherein said intracellular modulating agent is a JAK2 inhibitor, STAT3 inhibitor, interferon, CpG oligodeoxynucleotide (CpG ODN), cytotoxic agent, tumor necrosis factor alpha (TNFα), tumor necrosis factor beta (TNFβ), or Granulocyte-macrophage colony-stimulating factor (GM-CSF).

Embodiment 42

The method of embodiments 37 or 38, wherein the intracellular modulating agent is imiquimod, resiquimod, or oseltamivir.

Embodiment 43

The method of embodiment 35, wherein the intracellular modulating agent is imiquimod.

Embodiment 44

The method of any one of embodiments 1 to 42, wherein the nanoparticle composition forms part of a pharmaceutical composition, wherein the pharmaceutical composition comprises said nanoparticle composition and a pharmaceutically acceptable excipient.

Embodiment 45

A method of delivering an intracellular modulating agent to a cell in a subject, said method comprising intraperitoneally administering an effective amount of to said subject an effective amount of the nanoparticle composition.

Embodiment 46

The method of embodiment 45, wherein said cell is a macrophage.

Embodiment 47

The method of embodiment 45, wherein the cell is a tumor associated macrophage.

Embodiment 48

The method of any one of embodiments 45 to 47, wherein the average longest dimension of the nanoparticle composition is from about 200 nm to about 800 nm.

Embodiment 49

The method of any one of embodiments 45 to 47, wherein the average longest dimension of the nanoparticle composition is about 500 nm.

Embodiment 50

The method of any one of embodiments 45 to 49, wherein the nanoparticle composition has a net negative charge.

Embodiment 51

The method of any one of embodiments 45 to 50, wherein the nanoparticle composition is an inorganic nanoparticle, liposome, micelle, or polymeric nanoparticle.

Embodiment 52

The method of any one of embodiments 45 to 50, wherein the nanoparticle composition comprises silica, iron, gold, poly(lactic-co-glycolic acid) (PLGA), phospholipid, or polystyrene.

Embodiment 53

The method of any one of embodiments 45 to 50, wherein the nanoparticle composition is a nonporous silica nanoparticle or a mesoporous silica nanoparticle.

Embodiment 54

The method of any one of embodiments 45 to 50, wherein the nanoparticle composition comprises a block copolymer.

Embodiment 55

The method of any one of embodiments 45 to 50, wherein the nanoparticle composition comprises poly(ethylene glycol), poly(ethylene glycol)-block-poly(D,L-lactic acid) (PEG-b-PLA), chitosan, poly(methyl methacrylate) (PMMA), polyvinyl alcohol (PVA), poly(lactic-co-glycolic acid) (PLGA), or a combination thereof.

Embodiment 56

The method of any one of embodiments 45 to 55, wherein the nanoparticle composition is non-spherical.

Embodiment 57

The method of any one of embodiments 45 to 56, wherein the nanoparticle composition is bound to an intracellular modulating agent.

Embodiment 58

The method of embodiment 57, wherein the nanoparticle is non-covalently bound to said intracellular modulating agent.

Embodiment 59

The method of embodiments 57 or 58, wherein said intracellular modulating agent is a nucleic acid, antibody, polymer, protein, steroid, or a small molecule.

Embodiment 60

The method of embodiments 57 or 58, wherein said intracellular modulating agent is an pro-inflammatory agent.

Embodiment 61

The method of embodiments 57 or 58, wherein said intracellular modulating agent is a JAK2 inhibitor, STAT3 inhibitor, interferon, CpG oligodeoxynucleotide (CpG ODN), cytotoxic agent, tumor necrosis factor alpha (TNFα), tumor necrosis factor beta (TNFβ), or Granulocyte-macrophage colony-stimulating factor (GM-CSF).

Embodiment 62

The method of embodiments 57 or 58, wherein the intracellular modulating agent is imiquimod.

Embodiment 63

A silica nanoparticle non-covalently bound to a plurality of nucleic acids, wherein said silica nanoparticle has a net positive charge in the absence of the plurality of nucleic acids.

Embodiment 64

The nanoparticle of embodiment 63, wherein each of the plurality of nucleic acids comprises an intracellular modulating agent.

Embodiment 65

The nanoparticle of embodiments 63 or 64, wherein each of the plurality of nucleic acids comprises non-coding RNA (ncRNA).

Embodiment 66

The nanoparticle of embodiments 63 or 64, wherein each the plurality of nucleic acids comprises transfer RNA (tRNA), ribosomal RNA (rRNA), small interfering RNA (siRNA), or microRNA.

Embodiment 67

The nanoparticle of embodiments 63 or 64, wherein each of the plurality of nucleic acids comprises a TLR-binding nucleic acid substituent conjugated to a STAT-binding DNA substituent.

Embodiment 68

The nanoparticle of embodiments 63 or 64, wherein each of the plurality of nucleic acids comprises a TLR9-binding DNA substituent conjugated to a STAT3-binding DNA substituent.

Embodiment 69

The nanoparticle of embodiment 68, wherein the STAT3-binding DNA substituent comprises a first STAT3-binding DNA sequence covalently bound to a second STAT3-binding DNA sequence by a linker; and said linker is a substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

EXAMPLES

Example 1: Silica Nanoparticles Coated with CpG-STAT3decoy (dODN) Oligonucleotide CpG-STAT3dODN is a potential immunotherapy (see Blood. 2016 Mar. 31; 127(13):1687-700), whereby following uptake, CpG-STAT3dODNs are released from endosomes, and bind and sequester cytoplasmic STAT3, thereby inhibiting downstream gene expression in target cells. Here we are loading this molecule onto silica nanoparticles with a positive surface charge. The CpG-STAT3dODN is electrostatically absorbed on the surface to produce a particle with a negative surface charge.

Five hundred nm Sicastar® silica particles were purchased from Micromod GmbH. SiNP were dispersed in 10 mL water at a concentration of 5 mg/mL and reacted with 2 µL of (3-Aminopropyl)triethoxysilane (APTES) for 2 hrs at room temperature with rigorous stirring. The resulted amine functionalized particles were precipitated by centrifugation and washed with water by 3 times. See FIGS. 1A-1D for characterization data.

For CpG-dODN/NPs preparation, 5 mg SiNP—$NH_2$ were dispersed in 1 mL of PBS, followed by adding 5 µL of 100 µM CpG-dODN. The mixture was sit at room temperature for 2 hrs and stored at 4° C. for another 20 hrs. The resulted CpG-dODN/NPs were washed by PBS for 3 times before use. The CpG-dODN loading amount was characterized by fluorescent intensity measurement. This procedure is applicable to all nanoparticle-CpG-STAT3decoy (dODN) oligonucleotide compositions. Additional CpG-STAT3decoy (dODN) oligonucleotide compositions may be found in Zhang et al (Blood. 2016 Mar. 31; 127(13):1687-700) and WO 2015/077657, which are incorporated herein by reference for all purposes. The CpG-dODN employed herein used the sequence:

```
                                           (SEQ ID NO: 1)
5' G*G*TGCATCGATGCAGG*G*G*G*G-xxxxx-C*A*T*

TTCCCGTAAATC-xxxx-GATTTACGGGAA*A*T*G-xxxxx 3'
``` wherein (*=phosphorothioate linkage), x=is a linker, (—$(CH_2)_3$—) bonded to phosphate groups at both ends, except at the termini where terminal phosphates are optionally added and 5'x has an OH terminus and 3' x has a —$C_6$—$NH_2$ (e.g., aminohexyl) bonded to the final phosphate group, other linkages are phosphodiester.

Following uptake, CpG-STAT3dODNs are released from endosomes, and bind and sequester cytoplasmic STAT3, thereby inhibiting downstream gene expression in target cells. Here we are loading this molecule onto silica nanoparticles which have a positive surface charge. The CpG-STAT3dODN is electrostatically absorbed on the surface to produce a particle with a negative surface charge. Based on our previous work, we propose specific uptake by TAMs in the IP cavity.

Figure 3:
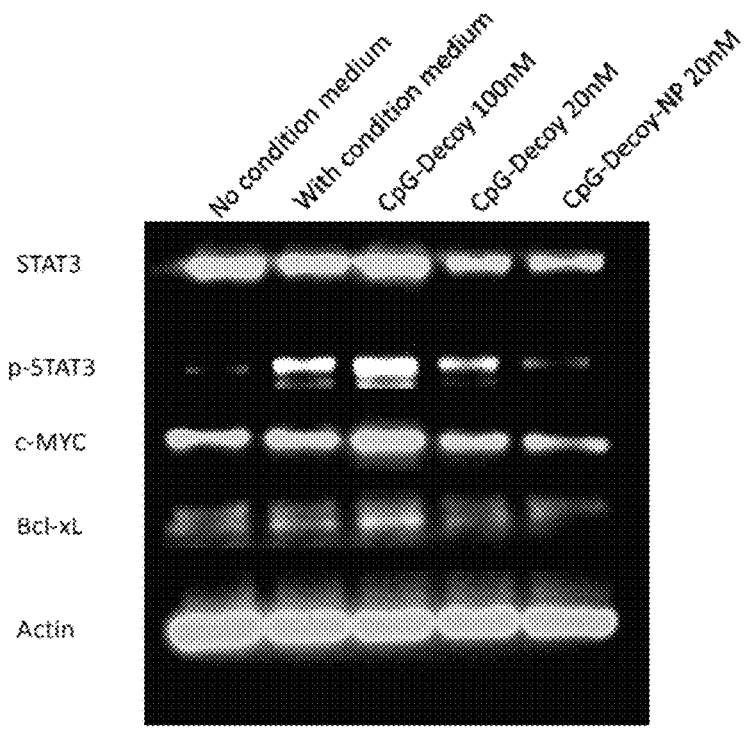
FIG. 3 The pilot testing in macrophages showed that the NP-delivered CpG-STAT3Decoy had better activity (reduction of p-STAT3) than the free CpG-STAT3Decoy at the same dose.
Figure 4:
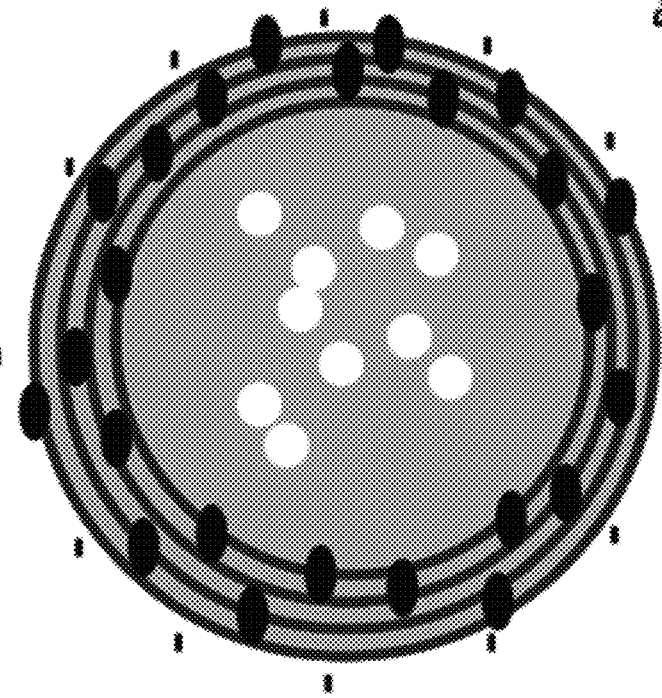
FIG. 4. Schematic overview of multilamellar anionic liposomes.
Figure 4:
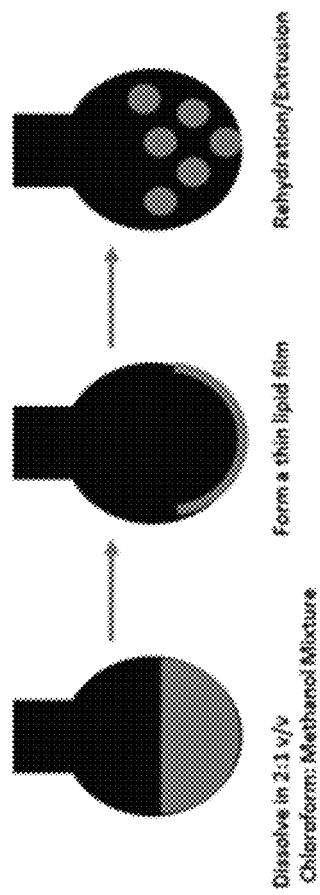
Figure 5:
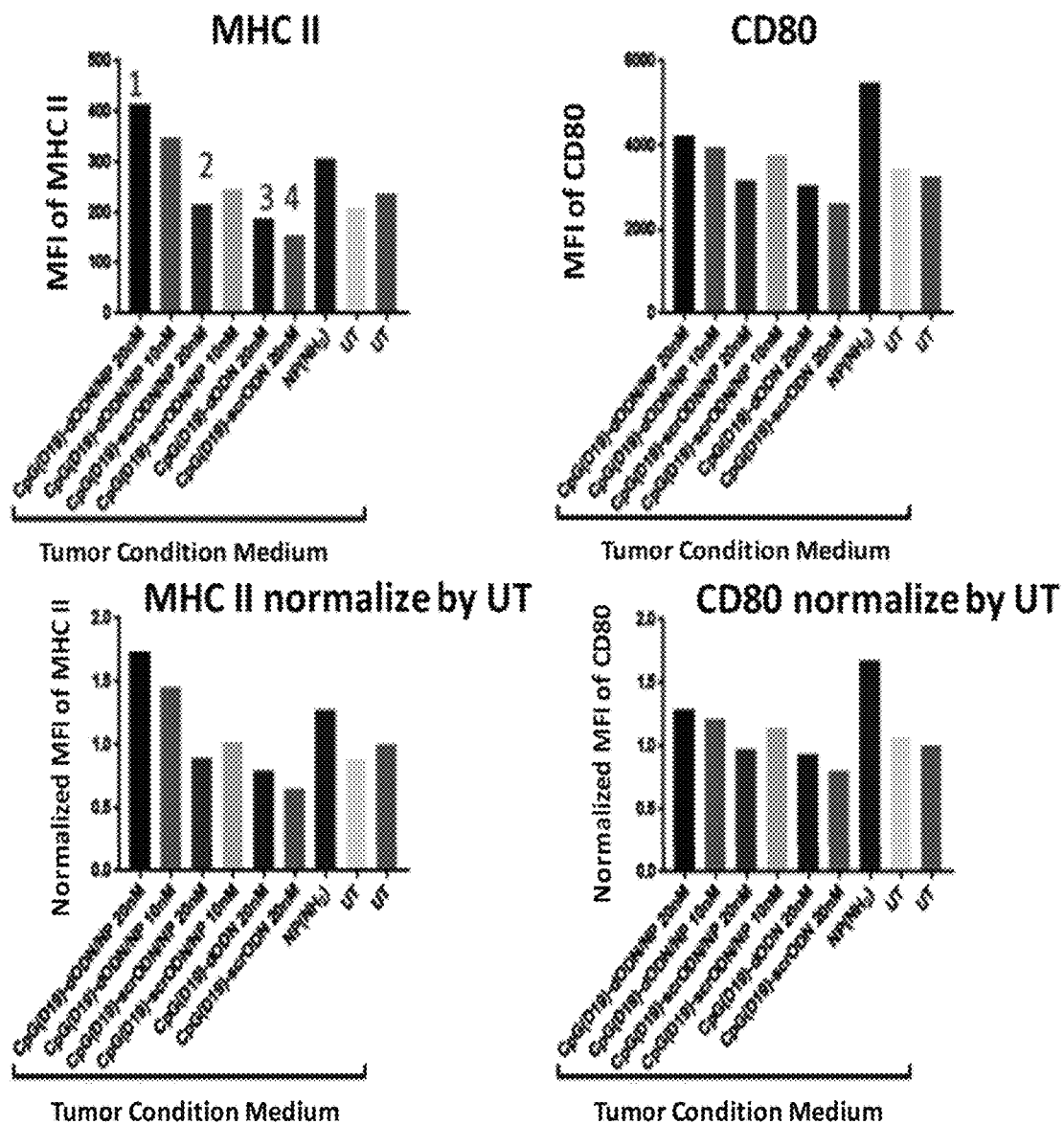
FIG. 5. The NPs functionalized with CpG-dODN (#1) cause activation of macrophages (as measured by increase in MHCII expression) as compared to NPs functionalized with CpG-scrambled_oligonucleotide (#2) or the oligos alone (#3 and 4).

Raw 264.7 cells were activated with tumor condition medium and incubated with CpG-STAT3decoy or SiNP/CpG-STAT3decoy, as observed in FIG. 3.

Example 2: Anionic Liposomes

The anionic liposomes are made of DPPC and DPPG lipids, which contains 32.8% DPPG and rest are DPPC. The nanoparticles will be greater than or equal to 200 nm in diameter; this example produces 400 nm liposomes. The liposomes that are >100 nm is typically multilamellar. The overall surface charge of this particle is around −30 mV. Incorporative dye for imaging purpose can be nile red (lipophilic); drugs that can be encapsulated may be hydrophilic molecules. These particles are made simply by dissolving the lipid mixture in chloroform/methanol mixture, evaporate the solvent to form a thin lipid film on the round bottom flask and then rehydrate using PBS follow by extrusion using proper size (0.4 um) polycarbonate membrane.

Example 3: Chitosan Functionalized Micelles

Negatively charged carboxymethyl chitosan grafted NPs (CMCNP) will be prepared through grafting polymerization of methyl methacrylate (MMA) onto chitosan derivatives, and their particle size and surface charge could be controlled by adjusting the reaction parameters. Various amounts of MMA solution and ammonium persulfate (APS) solution will be added to MC solution. The reaction is carried out at 75° C. The resultant NPs are dialyzed against water, and lyophilized. Then intracellular modulating agent (e.g., small molecules, therapeutic agents) can be incorporated into the NPs.

Example 4: PEG-b-PLA Block Copolymer

PEG-PLA micelles—immunotherapeutic payload compounds will be synthesized using nanoprecipitation process, consisting of placing the polymers with the small molecule into a glass vial, dissolving in THF, addition of subsequent organic phase to 10 mL water under probe sonication using a Hielscher device (model UP400S, Hielscher ultrasound technology, Germany) at 50% power for 2 min, and removal of THF by a rotary evaporator.

Example 5: PLGA Nanoparticles

PLGA will be dissolved in Dichloromethane (DCM) and small molecule drug can be introduced at this step. After complete dissolution, the drug solution is mixed with aqueous PVA solution to form the primary emulsion, then introduced to the high pressure. After homogenization, the processed emulsion is evaporated overnight to remove the DCM and collected by centrifugation. NPs are washed then dried powder is obtained by freeze-drying the nanosuspension.

Example 6: Nonporous Silica

Nonporous silica nanoparticles will be synthesized via the W/O microemulsion method using the quaternary Triton X-100, cyclohexane, hexanol and water system. Other type of microemulsion will also be used such O/W depending the immunotherapeutic payload. The small molecule will be incorporated in the beginning of the reaction. The NPs made with this step will have size range 100-200 nm and a further growth step will be performed using the Stober method to reach 400-500 nm size. Nonporous Si NPs can also be directly synthesized using Stober method to give a 500 nm size and the intracellular modulating agent (e.g., therapeutic agents) can be incorporated.

Example 7 Mesoporous Silica

Mesoporous silica NPs of 500 nm size can be synthesized separately in a first step. Premade (e.g., purchased) NPs of the same size can also be used and the small molecule will be added to the NPs and mixed for overnight to allow encapsulation into the pores. Characterization of the loading efficiency will be performed using HPLC.

Example 8: Ovarian Cancer Introduction

Ovarian cancer is a deadly disease that afflicts approximately 22,000 women per year in the US. Once it has reached stage III and metastasized to the abdominal cavity, there is a 5-year survival rate of only 28%. (1) Surgery is the frontline therapy for this disease and has two purposes. The first is to stage the cancer—to see how far the cancer has spread from the ovary. The second is to remove as much of the disease as possible—this is called debulking. Surgery is critical to patient outcomes with survival linked to the degree of tumor removed from the abdomen. (2) The current clinical standard is to remove all visible tumors larger than 1 cm in diameter, and even though surgeons can often remove tumors smaller than this, there are tumors too small to see with the naked eye. Indeed, despite achieving no gross visible disease with surgical debulking, 50-85% of patients will relapse. (3, 4) Moreover, the amount of residual disease at the end of surgery is subjectively reported with inherent surgeon bias. In order to improve clinical outcome, there is a critical need for the ability to detect tumors that are too small to see with the naked eye to enable more effective surgeries and more quantitative staging following surgery.

The most clinically advanced strategy for fluorescent detection of ovarian tumors is conjugating a fluorescent dye to folate, which binds to folate receptors that are highly expressed in ovarian cancer cells. However, over-expression of this receptor varies widely between different tumors and is present in lymph nodes and other normal tissue leading to false positive signals. (5) Recently, several groups have observed tumor specific accumulation of untargeted nanoparticles (NPs) administered intraperitoneally (IP), including: PLGA microparticles loaded with fluorophores or paclitaxel; (6) NPs composed of an amphiphilic copolymer of 2-methacryloxyethyl phosphorylcholine and n-butyl methacrylate loaded with paclitaxel; (7, 8) neutron-activatable holmium-containing mesoporous silica nanoparticles; (9) and, most recently, expansile NPs composed of a pH-responsive polymer. (10) Interestingly, in all of these cases, despite using NPs composed of different materials, the NPs are distributed on the surface of tumors but do not penetrate into the tumor. This selective tumor targeting is usually attributed to the specific NP characteristics and presumed to involve binding or internalization by cancer cells, though limited evidence is provided to validate this presumption. (6-9)

We recently also observed this phenomenon; when fluorescent silica NPs (SiNPs) that had no surface functionalization were administered IP, they selectively accumulated on the surfaces of tumors in a mouse model of abdominal metastatic ovarian cancer. (11) Here we show that these widely used, relatively inert and straightforwardly prepared particles can be used to selectively label tumors to guide surgery. Systematic variation of NP parameters demonstrated that selective labeling of tumors occurs over several days and is dependent on the particles being relatively large (>200 nm), anionic and being administered IP. The NP distribution on the surfaces of tumors, the lack of targeting ligands, the need for IP administration and wait time of several days following injection led us to suspect that macrophages were responsible for the selective accumulation, and this was confirmed by staining for known macrophage markers. We also found that following IP administration, another large, anionic particle (~800 nm polystyrene) shows selective tumor localization by uptake into macrophages. Taken together with the pre-existing literature, this argues strongly that selective targeting of tumors by large, anionic NPs administered IP is mediated by tumor associated macrophages (TAMs) and is quite general. Finally, we close this manuscript by demonstrating that not only do the NPs selectively label tumor surfaces in mouse models of abdominal metastatic ovarian cancer but also selectively label human tumor surfaces (and not normal tissues) in freshly excised surgical samples. Immunohistochemical staining confirmed that this tumor selectivity is also mediated by macrophages in the human tissue.

The impact of this work is twofold. First is the potential to improve surgical debulking by using NPs as intraoperative probes for selective detection of tumors too small to see with the naked eye. SiNPs are potentially attractive for clinical translation as they can be readily prepared with a variety of fluorophores, are relatively inert, and have previously demonstrated safety in clinical trials. (12-14) Moreover, the observation that a wide variety of large anionic NPs will likely work well for this application dramatically expands the design space for particles to use as intraoperative probes. The second area of impact is ovarian cancer therapy. TAMs are essential components of the tumor microenvironment that are involved in both pro-tumor and anti-tumor processes. (15, 16) The amount of TAMs in the tumor microenvironment and their polarization have been associated with shorter survival times, cancer progression, and poor prognosis in different cancer types including ovarian cancer. (17) It has been shown that depletion of TAMs slowed tumor growth and enabled T-cell infiltration into the tumors. (18, 19) The ability to target TAMs affords the opportunity to not only use probes to quantify them but to also use NPs to deliver drugs, including immunotherapeutic agents, selectively into TAMs.

Example 9: Results

Figure 6A:
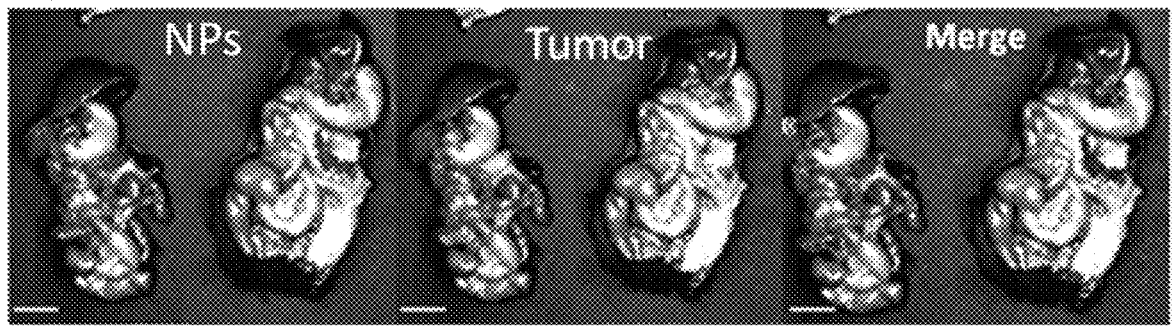
FIGS. 6A-6B. Red fluorescent-labeled SiNPs demonstrate selective tumor targeting when injected IP into a metastatic ovarian cancer mouse model. EGFP-expressing human ovarian cancer cells (OVCAR8) were injected IP. After 21 days, the red fluorescent-labeled SiNPs were injected IP and then 4 days later the animals were euthanized and IP cavity organ block removed for imaging.
Figure 6B:
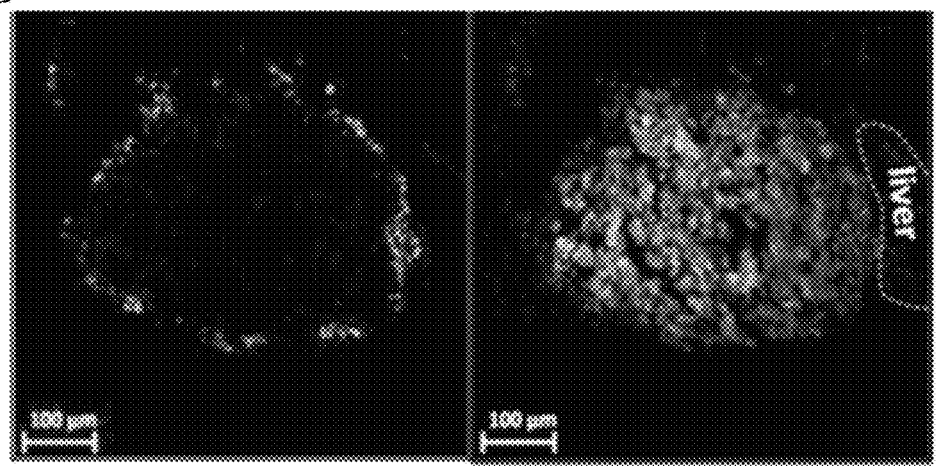
Figure 7:
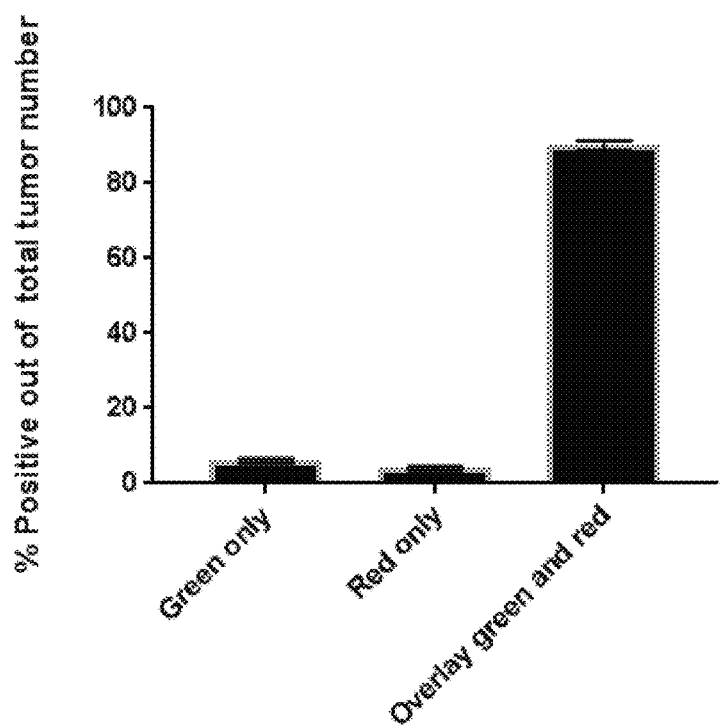
FIG. 7. Quantifying overlap between SiNPs and tumors in multiple mice. The percentage of the organ mass (from the organs in FIG. 6), corresponding to tumor cell density without NPs (colored in green only) or corresponding to SiNP density outside of tumor cells (colored in red only) is compared to the percentage of organ mass that corresponds to SiNPs that are localized at the site of the tumor (overlay red and green). As shown here, approximately 90% of the tumors were covered with NPs after NPs administration, in multiple mice out of 49 tumors.

In a pilot study using a metastatic mouse model of abdominal (stage III) ovarian cancer (human OVCAR8.EGFP cell line injected IP), we found that when non-functionalized SiNPs with a hydroxyl surface bearing an internal red fluorescent dye were administered IP, they selectively targeted ovarian tumor metastases, completely sparing non-tumor tissues. For these studies, tumor-bearing mice were euthanized 4 days post-SiNP injection, the organs in the IP cavity were removed and observed with a fluorescent wide field imaging system. This imaging demonstrated the SiNPs selectively localized to tumor sites (FIG. 6A). Tumors and adjacent healthy tissue were then dissected and prepared for confocal imaging, which further confirmed that the SiNPs only accumulated on tumor surfaces but not on normal (non-tumor) tissues (FIG. 6B). It also can be seen that even sub-mm tumors (0.5 mm) can be detected by these SiNPs. Thus, these non-functionalized SiNPs, without any attachment of targeting ligands, showed highly selective tumor targeting.

Figure 12A:
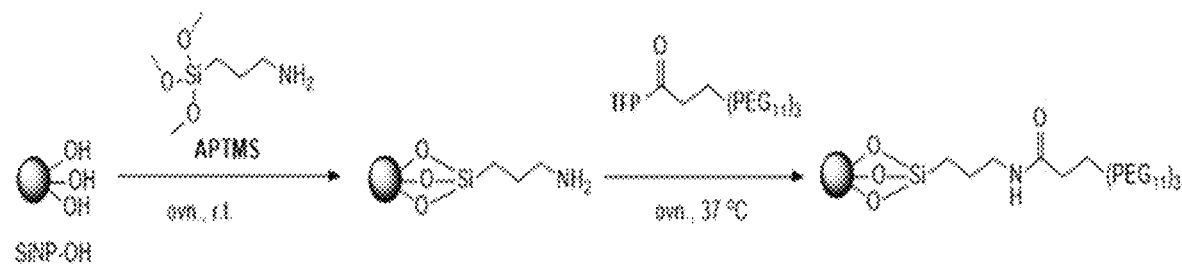
FIGS. 12A-D. The effect of surface charge on the selective tumor targeting of SiNPs. (12A) Schema of Hydroxyl-SiNPs, Amine-SiNPs and PEG-SiNPs preparation. (12B) TEM images, zeta potential (mV) and hydrodynamic size (nm) of the different SiNPs. (12C) Spectral Ami-X whole-body images of the IP cavity organ block. SiNPs red, tumors green. Scale bar=1.0 cm. (12D) Confocal images of the sectioned tumors (SiNPs red, eGFP tumors green/dense blue nuclei). Scale bar=200 am.
Figure 12B:
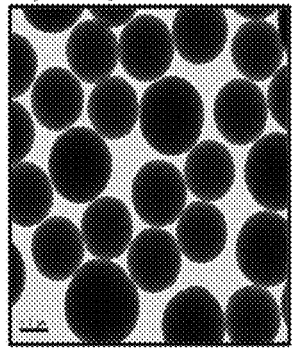
Figure 12B:
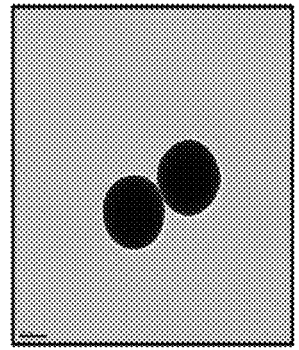
Figure 12B:
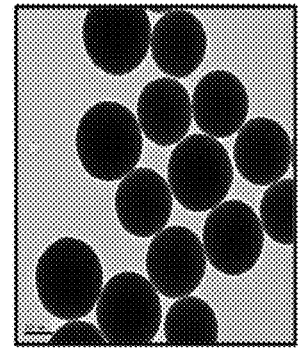
Figure 12C:
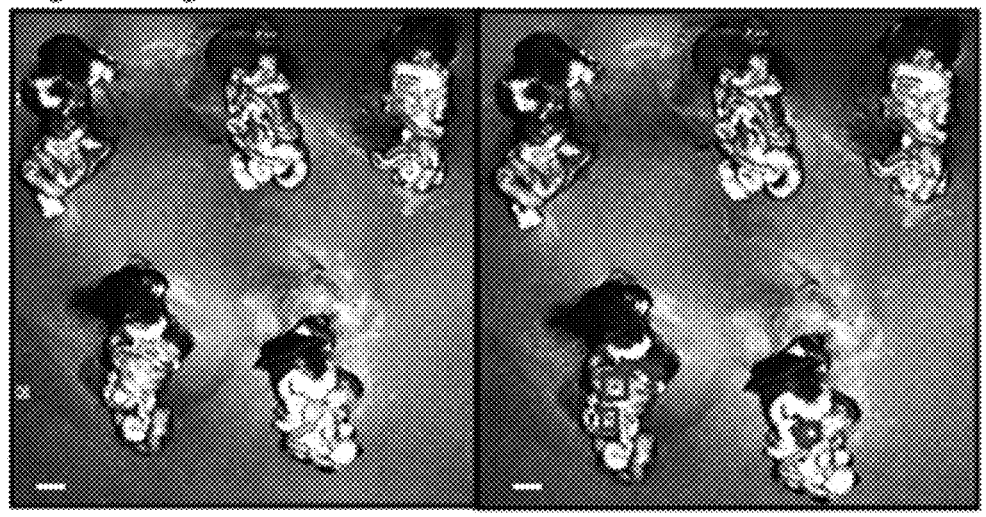
Figure 12C:
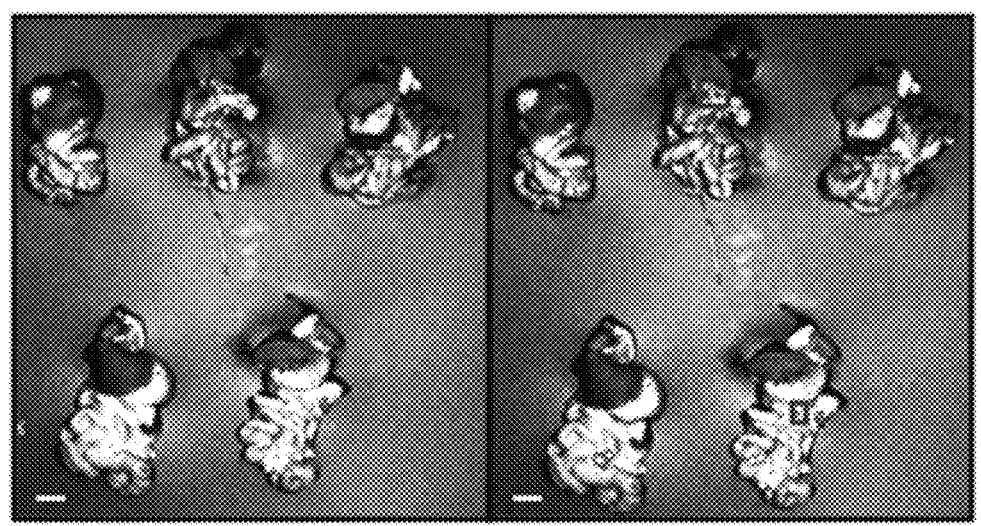
Figure 12C:
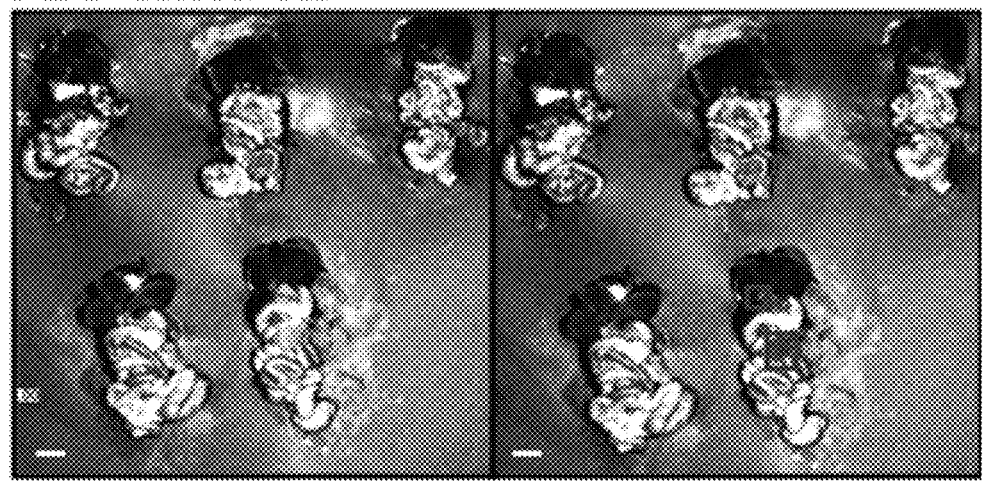
Figure 12D:
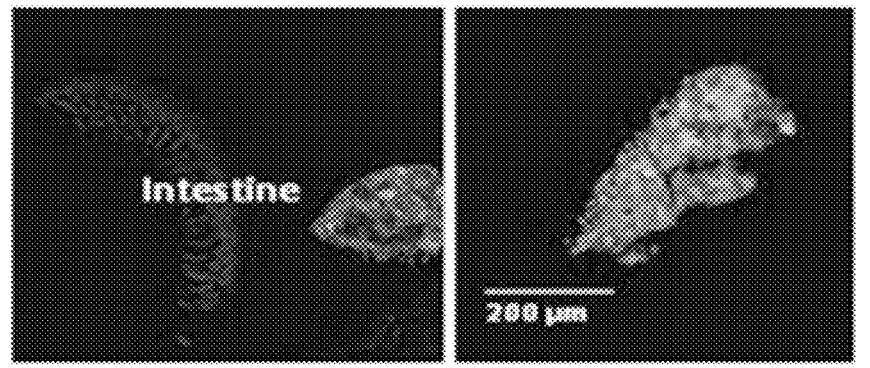
Figure 12D:
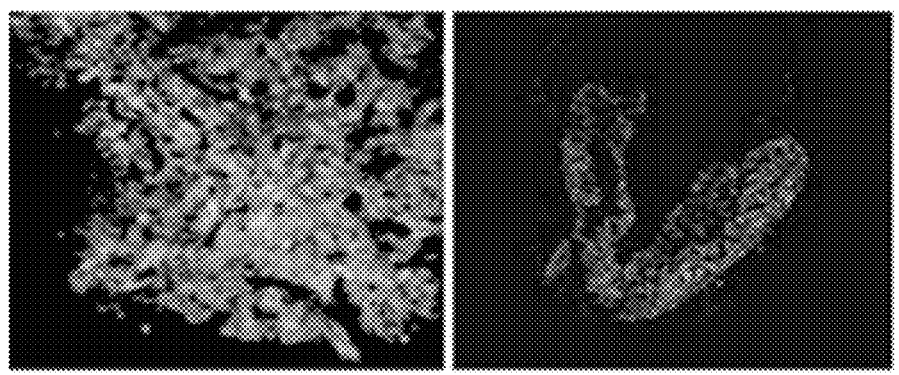
Figure 12D:
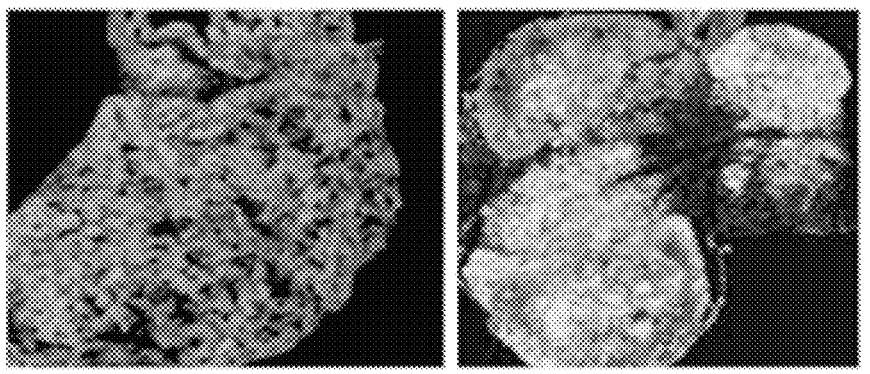

In a recent paper by Colby et al, published during our studies, it was found that IP administration of anionic NPs engineered such that they expand significantly at low pH resulted in selective localization of the NPs to ovarian tumors. Two control NPs were included that did not localize to tumors—one was unable to expand so it remained relatively small, and the other was able to expand but relatively neutral in charge. (10) The previous observations of selective tumor targeting by different particles such as: PLGA microparticles, NPs composed of an amphiphilic copolymer of 2-methacryloxyethyl phosphorylcholine and n-butyl methacrylate, and neutron-activatable holmium-containing mesoporous SiNPs (6-9) suggested to us that this targeting likely was not restricted to expansile particles but was rather a property of IP administration of sufficiently large and anionic particles. We began testing this hypothesis by using SiNPs with 3 different surfaces: hydroxyl (negative charge:

i-potential (mV): −55.74), amines from coating the hydroxyl particles with (3-Aminopropyl)triethoxysilane (positive charge: ζ-potential (mV): +22.88) and poly(ethylene glycol) (PEG) from reacting the amine particles with PEG-N-hydroxysuccinimide (less positive effective charge: ζ-potential (mV): +10.58), (FIG. 12B). Human OVCAR8.EGFP ovarian cancer cells were administered IP to immunodeficient mice to generate abdominal metastases and 21 days later SiNPs were administered IP. Four days after injection of SiNPs, IP organ blocks were removed and imaged using a wide field fluorescence imaging system. Tumors and healthy tissue were then sectioned for confocal imaging. Supporting our hypothesis, the cationic, amine functionalized SiNPs had minimal tumor targeting, the PEGylated SiNPs had modest tumor targeting and the anionic, hydroxyl SiNPs had highly selective tumor targeting (FIG. 12C, D).

Figure 8:
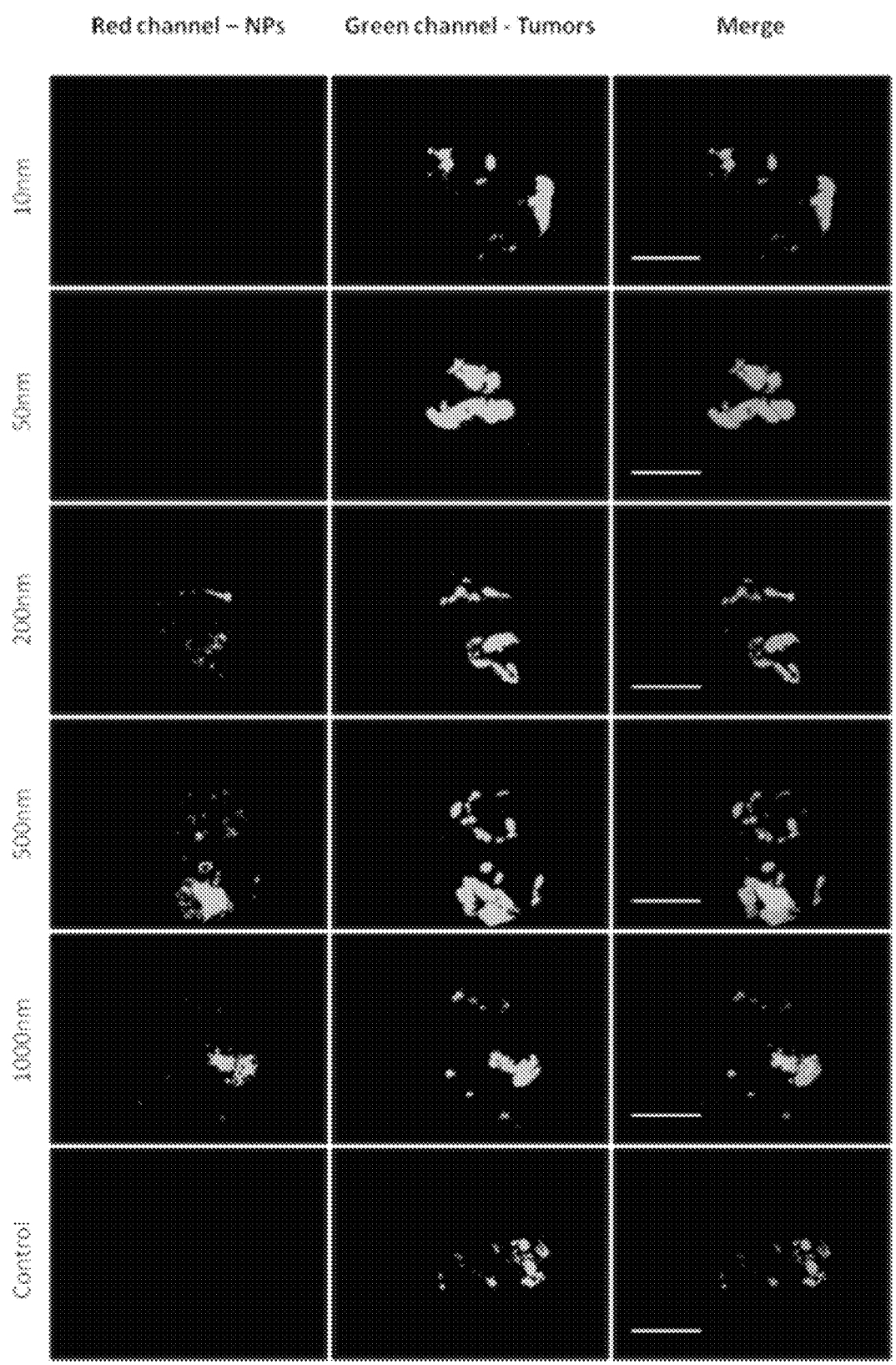
FIG. 8. The effect of SiNP size on the selective tumor targeting. Leica Z16 dissection macroscope images of IP cavity organ block 4 days after the IP injection of 10, 50, 200, 500 and 1000 nm red fluorescent-labeled SiNPs with a hydroxyl surface and no SiNP control. Left panels: SiNPs red, Middle panels: tumor cells green, Right panels: merged images showing overlap orange/yellow. Scale bar=1.0 cm.
Figure 31:
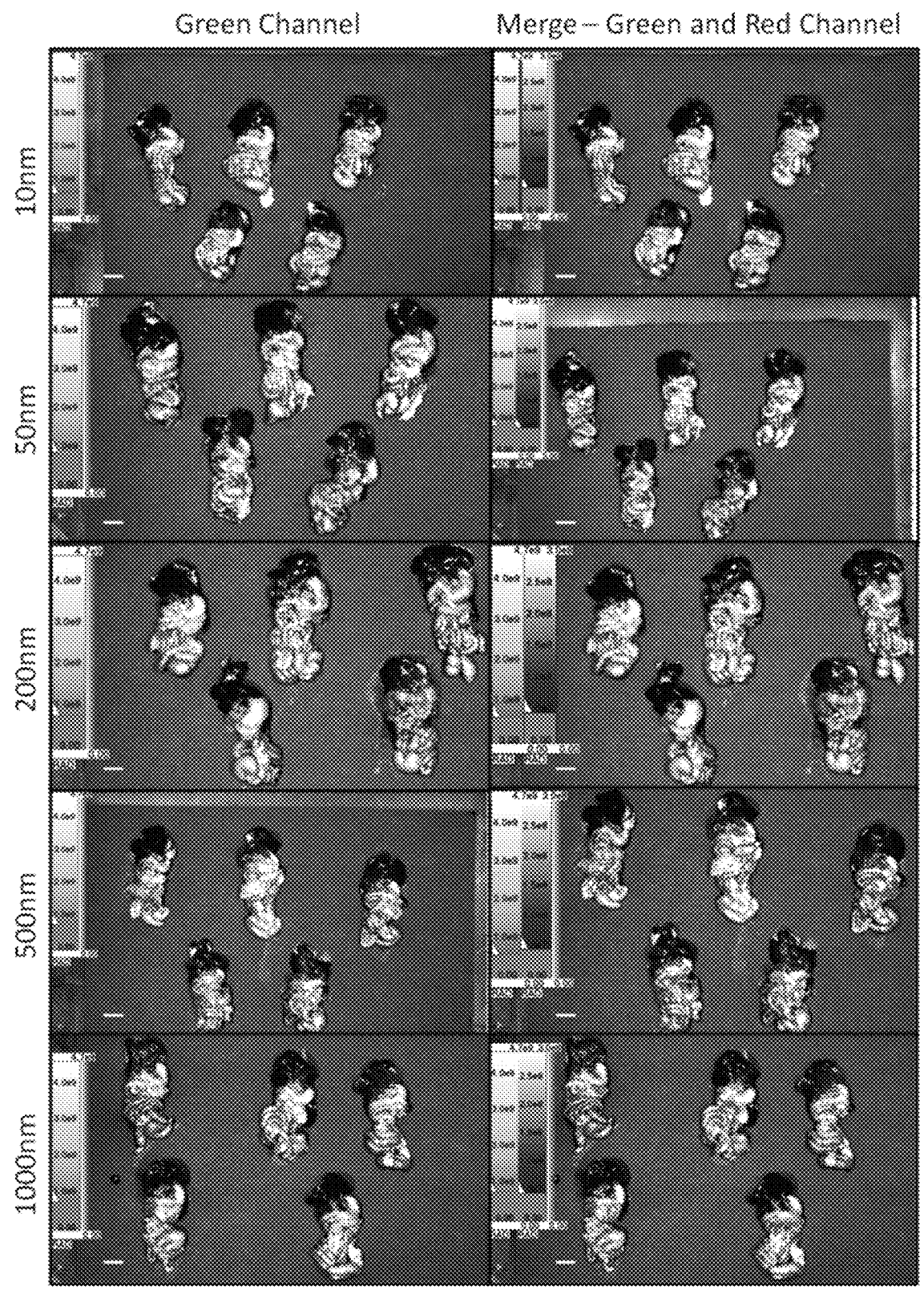
FIG. 31. The effect of size on the selective tumor targeting of SiNPs. Spectral Ami-X wide-field images of the IP cavity organ block 4 days after IP injection of 10, 50, 200, 500 and 1000 nm red-fluorescent-labeled SiNPs and no SiNP control (SiNPs red, eGFP tumors green). Scale bar=1.0 cm.

The impact of SiNP size was next investigated using 5 different sizes of the red fluorescent-labeled non-functionalized SiNPs (with a hydroxyl surface): 10, 50, 200, 500 and 1000 nm. In addition to wide field fluorescence imaging (FIG. 31), we used a dissection macroscope which afforded much improved resolution and sensitivity while maintaining a relatively large field of view (3 cm in diameter). For this imaging technique, there is a background red signal from the organs. To account for this, the threshold for red fluorescence intensity in all images was set above that measured in the no SiNP control. Results demonstrated minimal tumor targeting for particles <200 nm, and significantly superior tumor coverage with 500 nm SiNPs compared to the 200 or 1000 nm SiNPs (FIG. 8, FIG. 31). The size dependence of tumor targeting may correlate with the circulation time of the NPs in the IP cavity, as Feng. et al, showed that liposomes smaller than ~200 nm that were administrated IP were able to traverse into the blood stream, while liposomes of size ~400 nm showed negligible uptake into the blood stream and their retention was limited to the peritoneum cavity and the surrounding areas. (20)

Figure 13A:
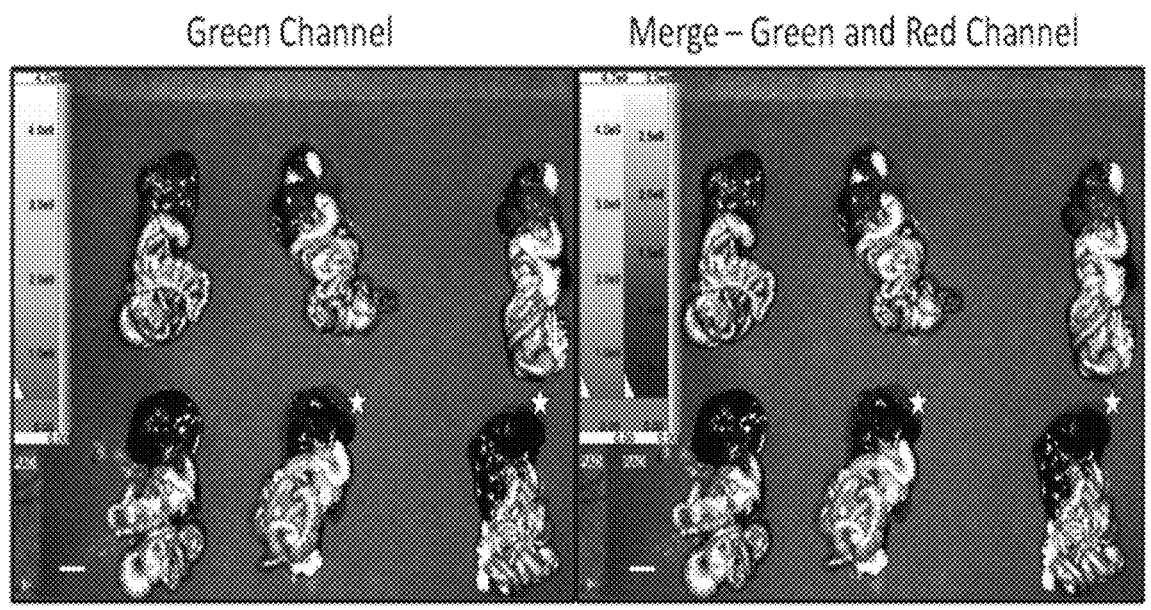
FIGS. 13A-B. The effect of route of administration on the selective tumor targeting of SiNPs. (13A) Spectral Ami-X wide-field images and (13B) LeicaZ16 issection macroscope images of the IP cavity organ block 4 days after IV injection of 500 nm red-fluorescent-labeled SiNPs (red). No SiNP controls (indicated by white stars). Scale bar=1.0 cm.
Figure 13B:
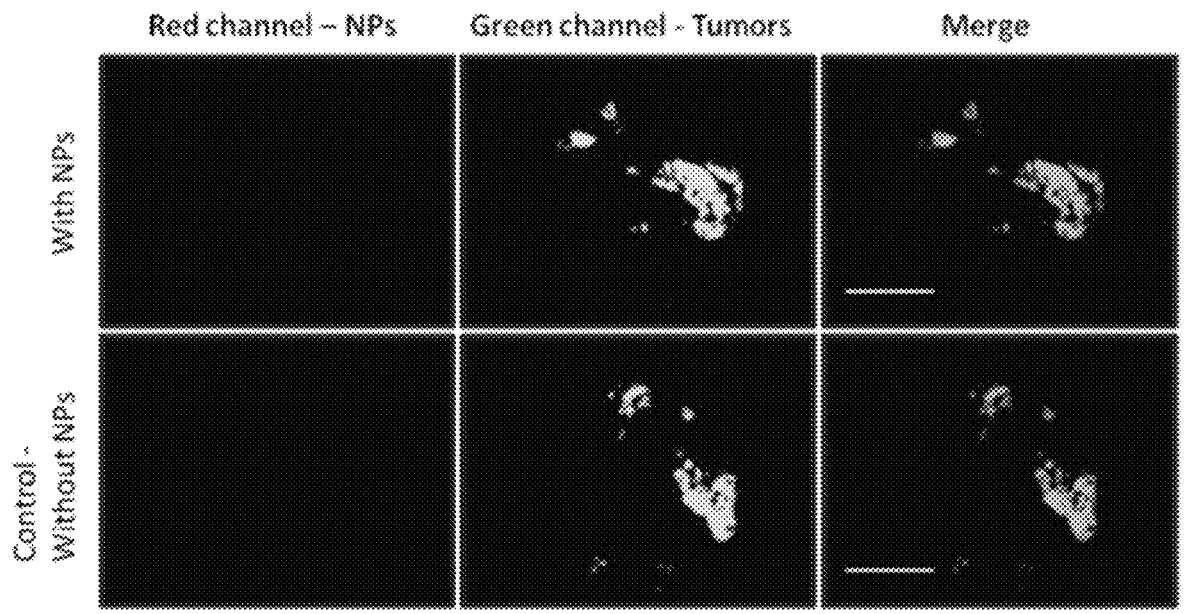

To further investigate if IP circulation is important for tumor targeting, we compared the effect of IP versus IV route of SiNP administration. Examination of the tumors and IP organs 4 days post-IV injection of the 500 nm SiNPs (1 mg NPs/mL) with a hydroxyl surface showed lack of red fluorescent signal in the peritoneal cavity, as can be seen from the images taken with a wide field imaging system, and from the dissection macroscope images (FIG. 13).

Figure 9:
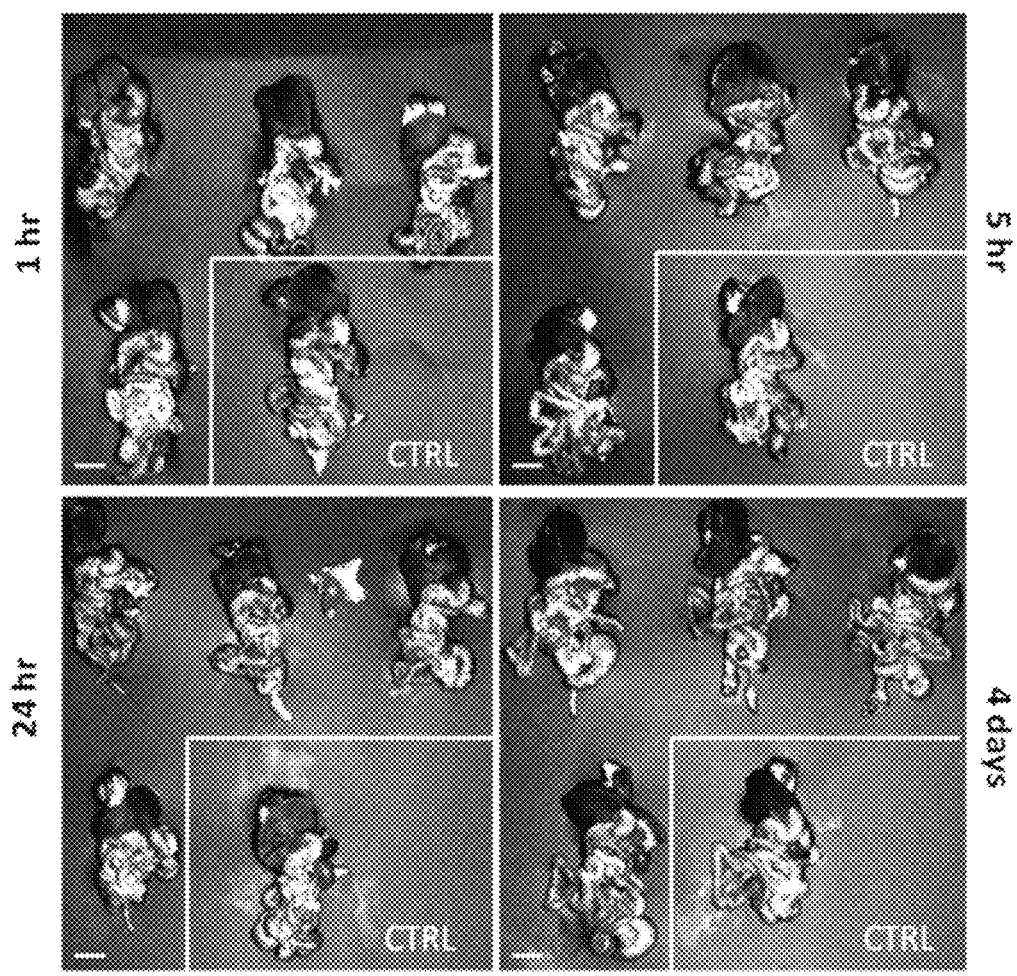
FIG. 9. Kinetics of attachment of the silica nanoparticles. (A) Spectral Ami-X wide field images of the IP cavity organ block 1, 5, and 24 hours, and 4 days after SiNP (red) injection, EGFP tumors (green). No SiNP control indicated by white border. Scale bar=1.0 cm.

Next, we evaluated the optimal timing between SiNP administration and imaging to determine the kinetics of SiNP localization to the tumors. The 500 nm red fluorescently-labeled non-functionalized SiNPs were injected IP to tumor-bearing mice and then the mice were euthanized 1, 5, 24 hours and 4 days later. IP cavity organ blocks were removed and imaged by a wide field imaging system. As seen in FIG. 9, there was no to minimal red signal at tumor sites with short incubation times (1 and 5 hours). SiNP localization to tumors started to be visible after 24 hours and the highest tumor biodistribution was detected after 4 days, with SiNPs seen selectively co-localized to tumors in all mice.

Figure 10:
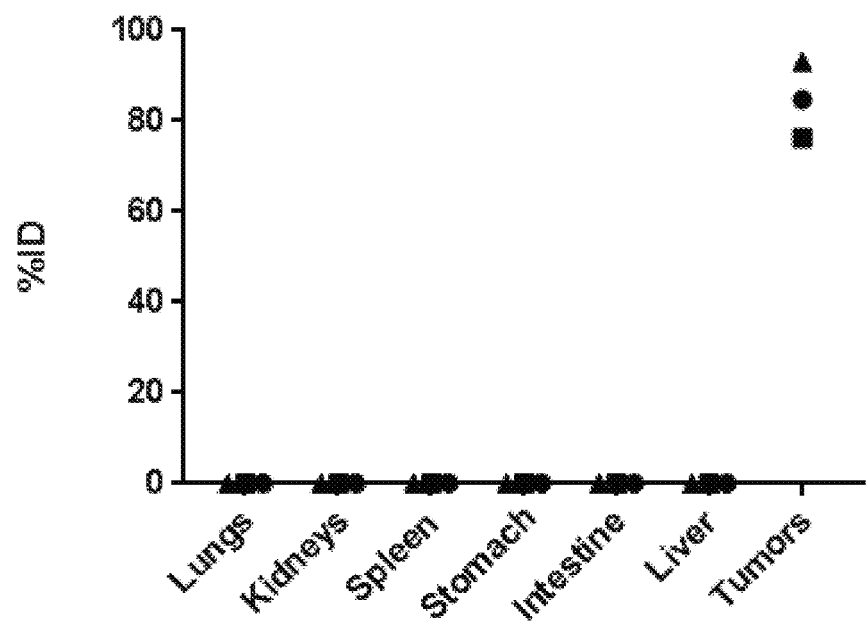
FIG. 10. Biodistribution of the silica nanoparticles. ICP-MS evaluation of biodistribution, showing percentage of injected dose of Au@SiNPs (silica nanoparticles labeled with a gold core) in major organs harvested after 4 days (n=3 mice, each mouse is represented with a different shape). The gold/silica nanoparticles accumulated predominantly around the tumors with 84.8%±8.5% of the injected dose found in the tumors. All signals from other organs were below the limit of detection of the ICP/MS. Approximately 85% of the total injected dose is in the tumors.

To determine if signal from the tumors accounted for most of the injected SiNP dose or if we were missing signal from SiNPs that may have accumulated in other off-target tissues where the SiNPs were too far from the organ surface for detection by fluorescent imaging, we used SiNPs with a gold core (Au@SiNPs). The use of a gold core allows for more precise measurement by inductively coupled plasma mass spectrometry (ICP-MS) since there is no background gold signal in tissue but there is a background silica signal. The largest particles we were able to produce were 50 nm gold NPs coated with a 75 nm thick Si shell to yield particles of ~200 nm in diameter. The Au@SiNPs were injected IP to 3 tumor bearing mice, and IP organ blocks harvested 4 days later. Biodistribution was determined by measuring gold by ICP-MS (FIG. 10). Remarkably, 84.8±8.5% of the injected dose was found at the tumors. All signals from other organs were below the limit of ICP-MS detection. This highly efficient delivery to tumors is actually in agreement with previous work from Di Pasqua et al, who found that when radiolabeled SiNPs (~100 nm, ζ-potential of −49.2 mV) were injected IP into mice bearing metastatic SKOV-3 tumors the signal in the tumors increased over time and reached 81% ID/g after 1 week which was more than 12 times that in any other organ. (9)

Figure 14A:
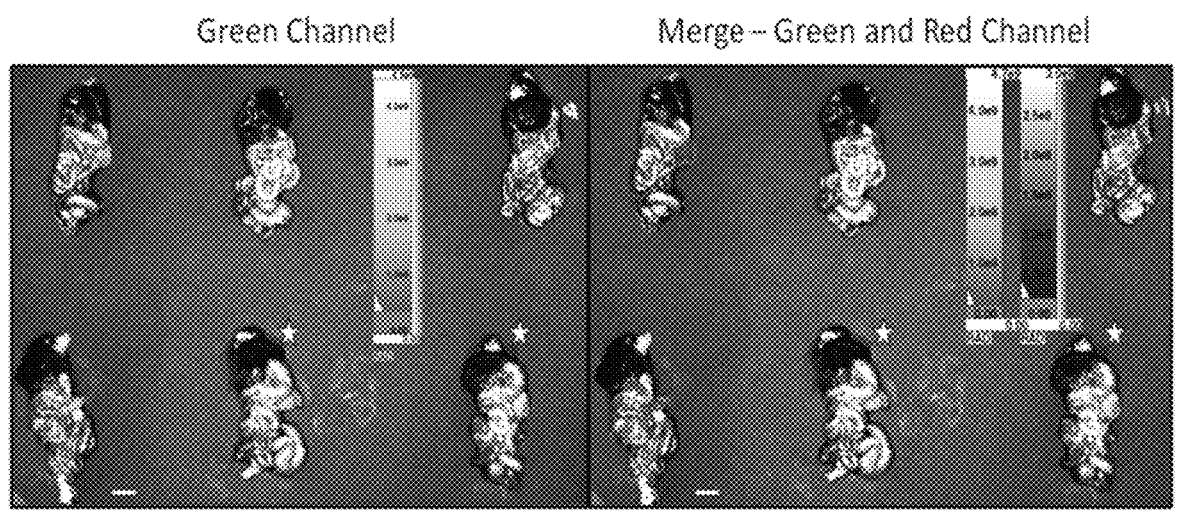
FIGS. 14A-B. SiNPs target additional ovarian cancer cell line. Human SKOV-3.eGFP ovarian cancer cells were injected IP to generate abdominal metastases (14A) Spectral Ami-X wide-field images and (14B) Leica Z16 dissection macroscope images of the IP cavity organ blocks 4 days after the IP injection of 500 nm red fluorescent labeled SiNPs red, tumors green. No SiNP controls (indicated by white stars). Scale bar=1.0 cm.
Figure 14B:
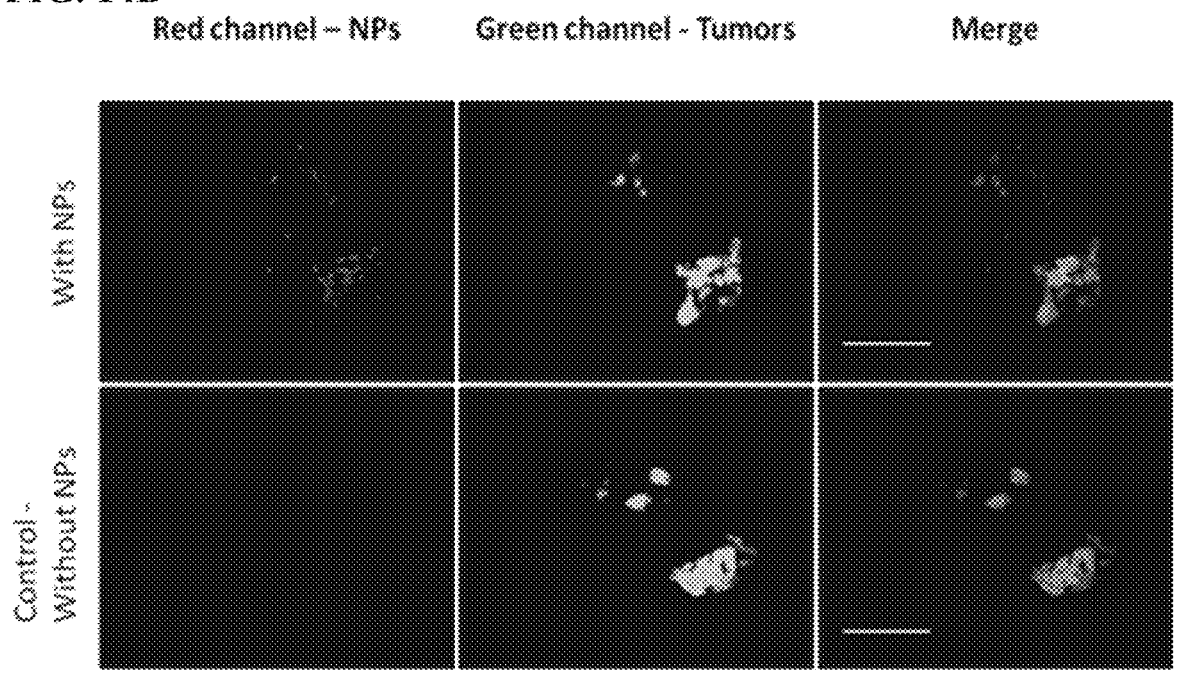

We confirmed that our SiNPs also selectively label SKOV-3 tumors (FIG. 14A, 14B) in addition to the OVCAR-8 derived tumors shown throughout the main text. Collectively, the data described thus far showed that when appropriately sized (~500 nm) and non-functionalized (hydroxyl surface) SiNPs are administered IP, highly efficient and selective labeling of ovarian tumors is achieved 4 days later.

Figure 30A:
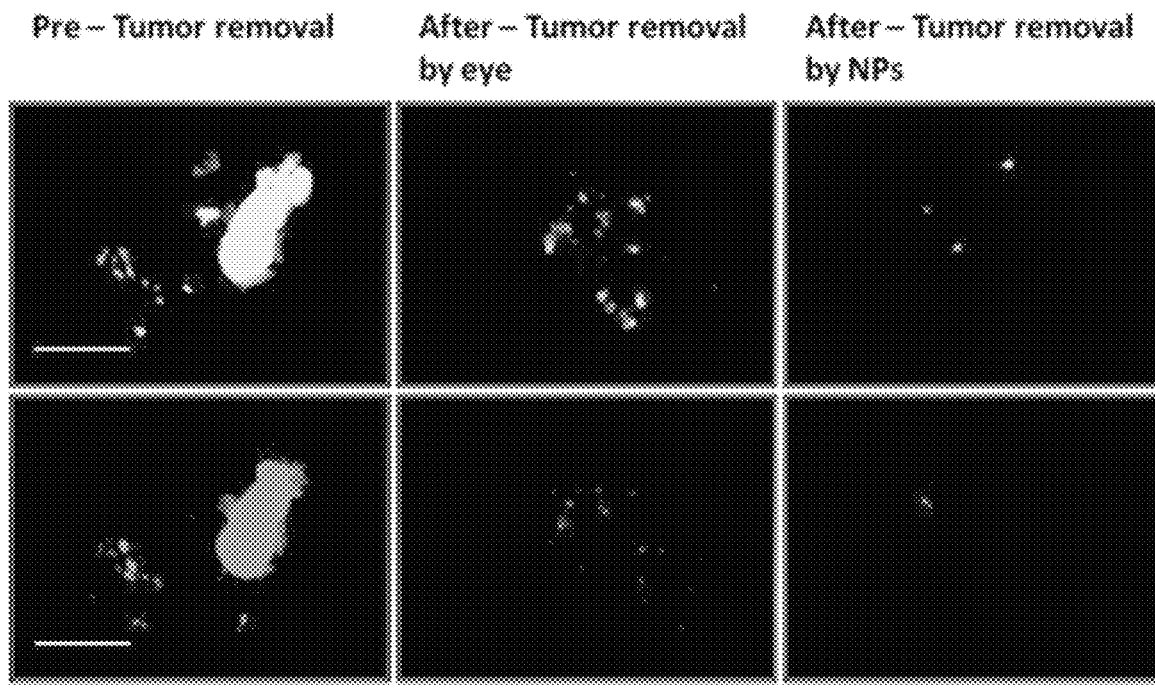
FIGS. 30A-B. Image guided surgery based on use of red fluorescent-labeled SiNPs.
Figure 30B:
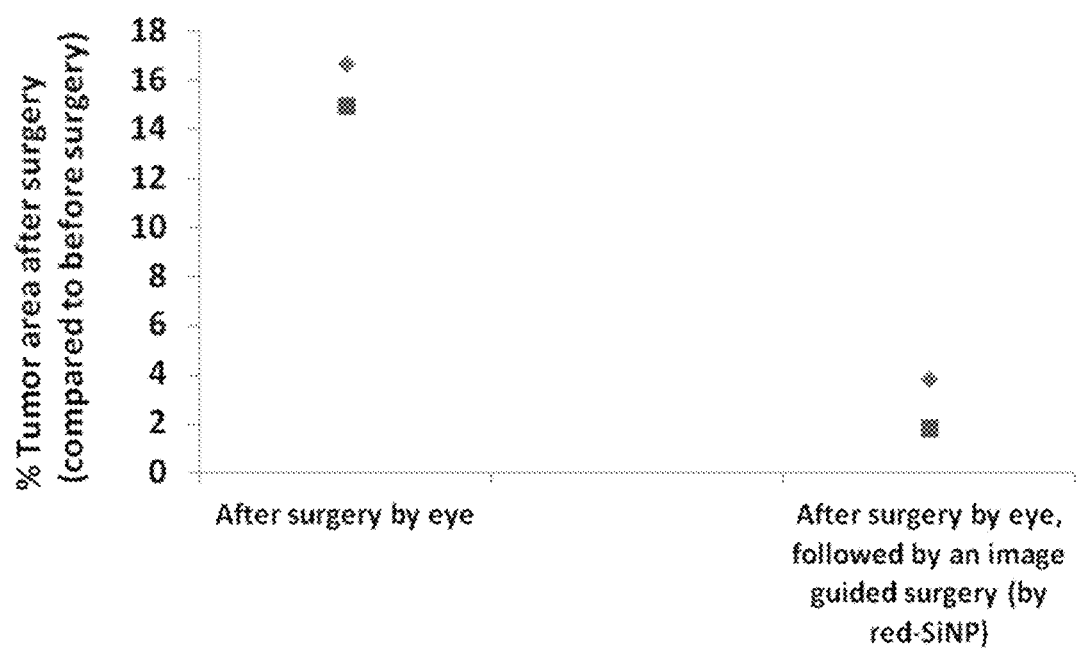

Based on the ability of the SiNPs to selectively distribute to tumors in the IP cavity, we evaluated the feasibility of using these SiNPs as intraoperative fluorescent probes in an ex-vivo surgical resection of ovarian tumors in mice. For these studies, the SiNPs were injected IP to tumor bearing mice, and IP cavity organs harvested after 4 days. In order to evaluate the potential benefit of fluorescent labeled SiNPs during surgery, the following protocol was used:

1. Image organ block using dissection macroscope; 2. Surgically resect all tumors that could be seen by eye; 3. Image the organ block for a $2^{nd}$ time; 4. Use the red SiNP signal from this imaging to guide a second round of surgical resection; and 5. Image the organ block for a $3^{rd}$ time From the three imaging rounds, it is clear that there was a significant reduction in tumor mass after the image-guided surgery compared to the initial surgical resection based on eye sight (FIG. 30A). When the area of the tumor signal (green) was quantified, it was found that 16% of the original signal remained after the initial tumor resection by eye while only 3% of the original signal remained after the second tumor resection using SiNP-guided detection (FIG. 30B). Our results demonstrate IP injection of non-functionalized, 500 nm fluorescent-labeled SiNPs enables detection and removal of small ovarian tumors not detected by the naked eye, which is currently the gold-standard in ovarian cytoreduction surgeries.

Figure 15:
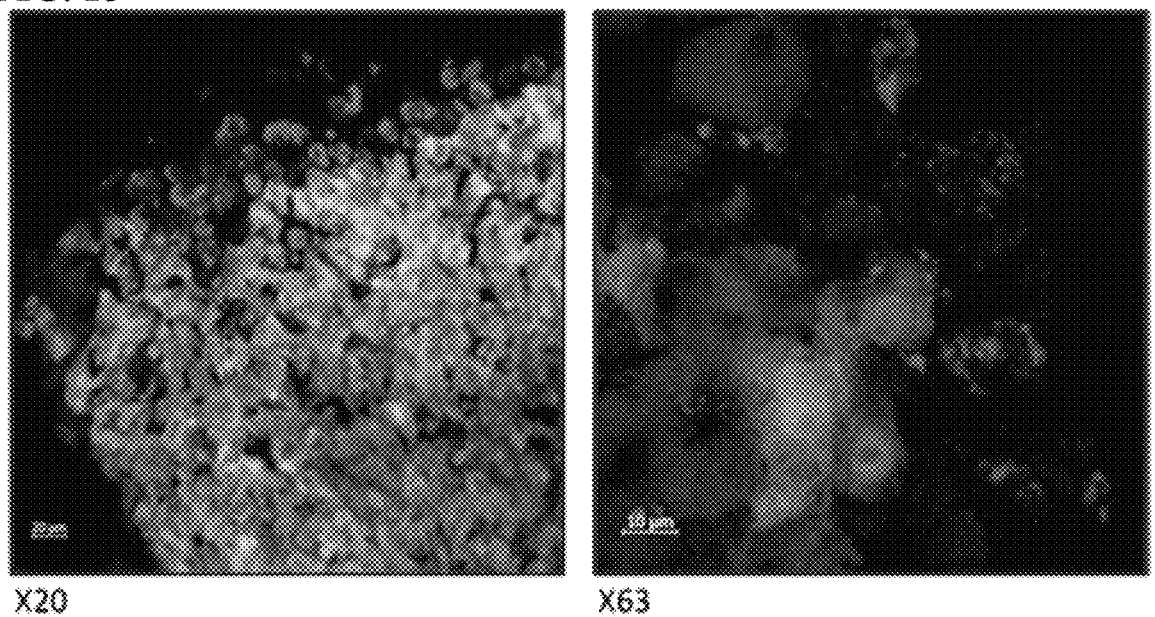
FIG. 15. Uptake of red fluorescent SiNPs by TAMs. Confocal images of representative sectioned tumors 4 days after IP injection of red fluorescent SiNPs. The red signal from the SiNPs does not colocalize with the green signal of the tumor cells. The NPs are in tumor area, but are not incorporated directly in the tumor cells. EGFP-expressing human ovarian cancer cells (OVCAR8) were injected IP. After 21 days, 500 nm red fluorescent-labeled SiNPs were injected IP and then 4 days later the animals were euthanized and IP cavity organ block removed and prepared for confocal imaging.

We next explored why SiNPs with just a hydroxyl surface (i.e. unfunctionalized) were localizing to tumors so selectively. Given our observations that SiNPs accumulate at high density only at the surface of tumors, the necessity of IP administration, and tumor localization taking several days, we hypothesized that the NPs are circulating in the IP cavity and being taken up by cells. If the targeting instead occurred through either extravasation from blood vessels or attachment to extracellular matrix, we would expect that IV administration or shorter time periods would work, respectively. To further clarify the location of the SiNPs at the tumor foci, tumors from treated mice were sectioned and imaged by confocal microscopy at high magnification (63×, FIG. 15). Interestingly, the red SiNP signal was found to be clearly located inside cells, but did NOT co-localize with the GFP-expressing cancer cells (FIG. 15).

Figure 16:
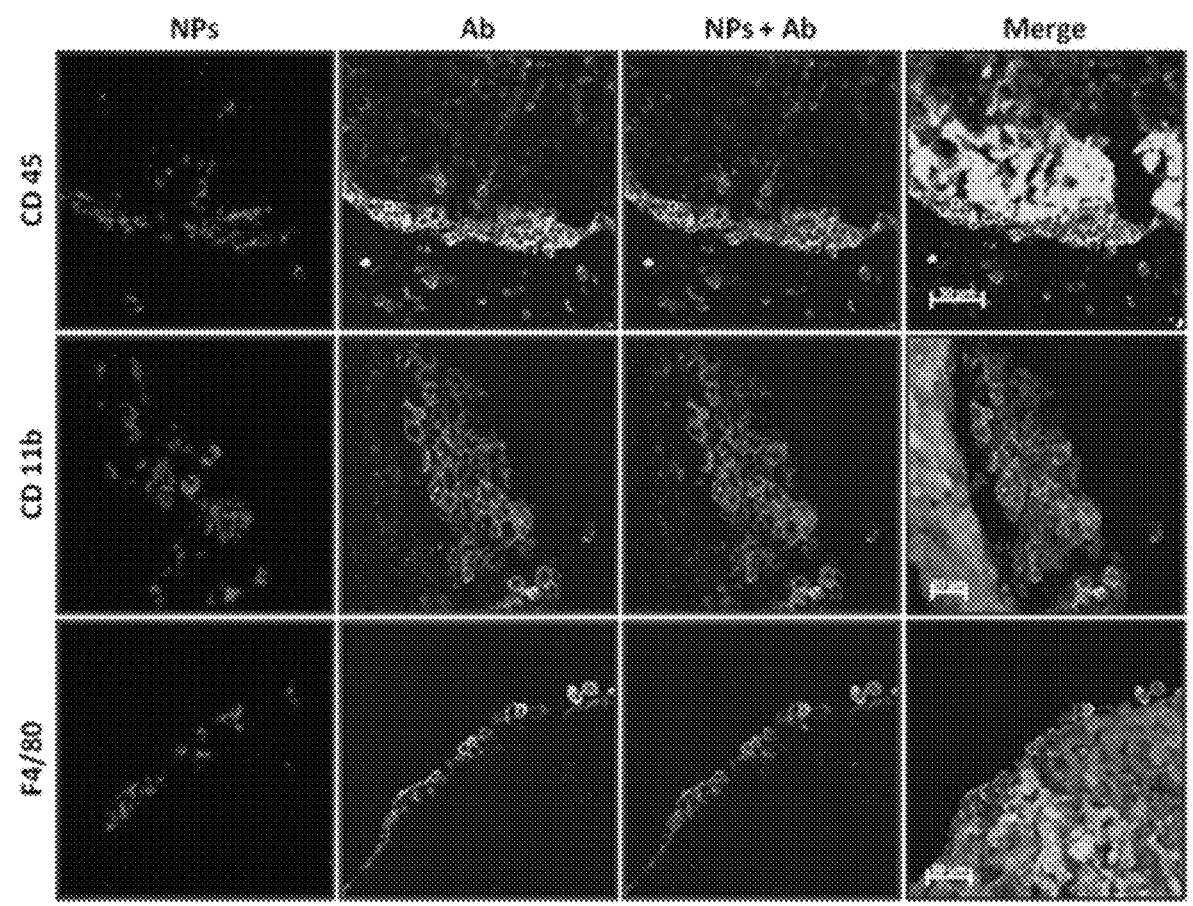
FIG. 16. Uptake of red fluorescent SiNPs by TAMs. 500 nm red fluorescent-labeled SiNPs red, tumors green, DAPI stained nuclei blue in cells (NPs). Macrophage biomarkers (Anti-CD45, Anti-CD11b and Anti-F4/80 antibody) staining yellow to identify TAMs. (Ab). Note merged images in far right panels showing co-localization of SiNPs and macrophages at tumor surface. Scale Bar=50 µm.
Figure 32:
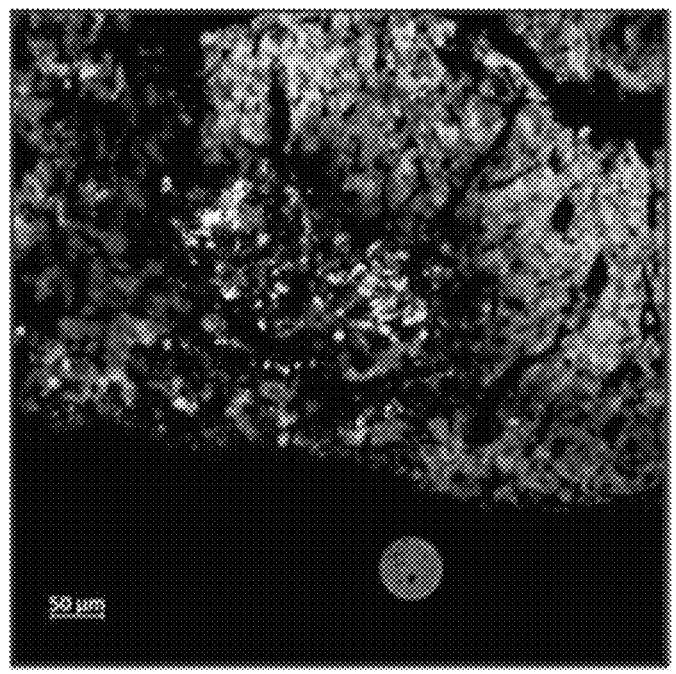
FIG. 32. Myeloid-Derived Suppressor Cells (MDSCs) immunohistochemistry. Confocal image of sectioned tumor 4 days after IP injection of red fluorescent SiNPs, eGFP tumors green, DAPI nuclei blue, Anti-GR1 antibody—Yellow.
Figure 33:
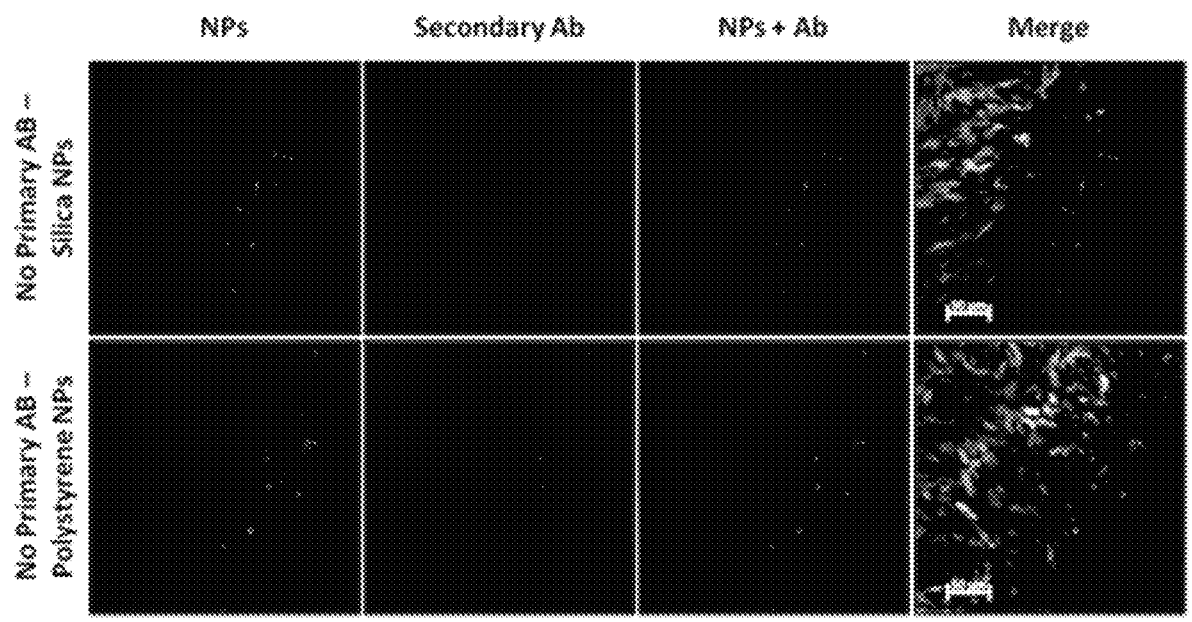
FIG. 33. Confocal imaging of no primary antibody controls.

Given the affinity of macrophages for NPs and the abundance of macrophages in tumors, we hypothesized that macrophages contained most of the SiNPs. Indeed, immunofluorescence staining of tumors from treated mice revealed that the red fluorescent SiNPs showed low co-localization with GR-1+ cells (granulocytes marker) (FIG. 32), and high co-localization with CD45+(hematopoietic cells marker)/CD11b+(myeloid cells marker)/F4/80+(murine macrophages marker) cells (FIG. 16). This marker status is indicative of macrophages and demonstrates that SiNP tumor targeting is achieved by selective uptake by tumor associated macrophages (TAMs). These results explain the distribution of SiNP on the tumor surface without penetrating into the tumor core (FIG. 6B).

Figure 17A:
FIGS. 17A-B. TAMs take up large, negatively charged red fluorescent-labeled polystyrene NPs after IP injection.
Figure 17B:
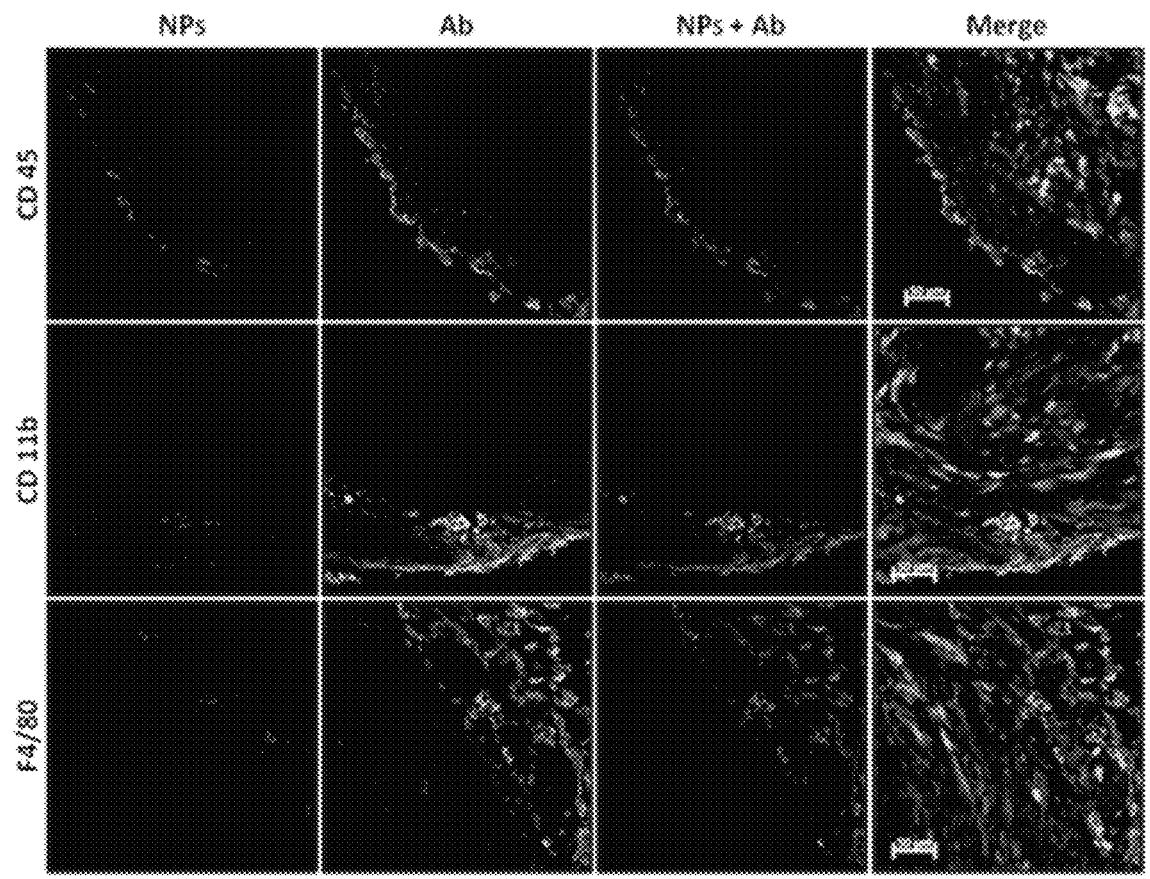
Figure 18A:
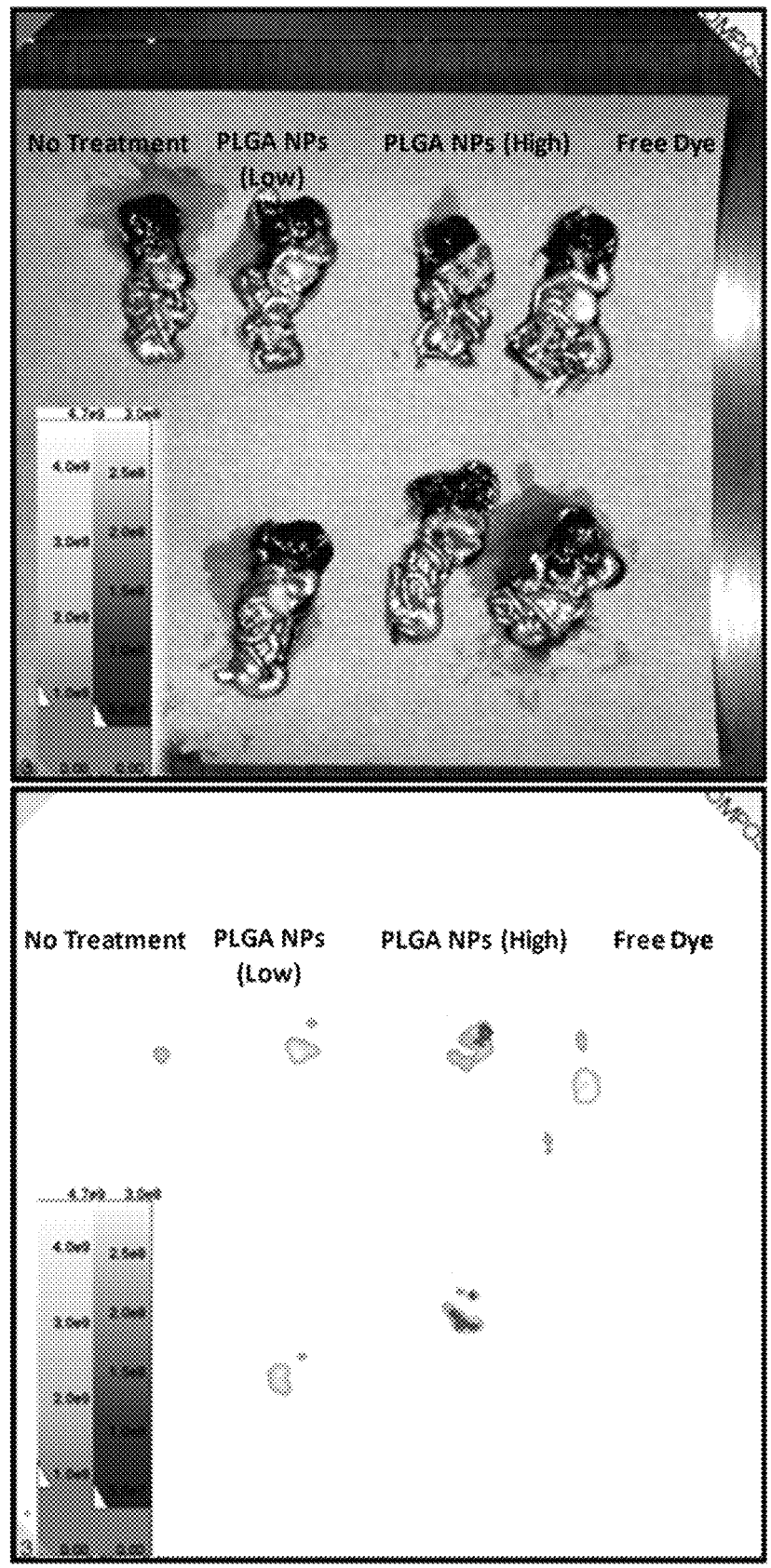
FIGS. 18A-B. Targeting of tumors using poly(lactic-co-glycolic acid) (PLGA) nanoparticles. The top image shows the organs, whereas the bottom image shows the localization of the PLGA nanoparticles. High PLGA—the fluorescence intensity was matched to the number of 500 nm red fluorescently labeled SiNPs that we usually inject (high intensity therefore more PLGA NPs needed—high number of PLGA NPs. Low PLGA refers to PLGA nanoparticles wherein the fluorescence intensity was matched to the free dye; Nile red has low solubility and florescence intensity in PBS—therefore low number of PLGA NPs. There are 6 mice in each group.
Figure 18B:
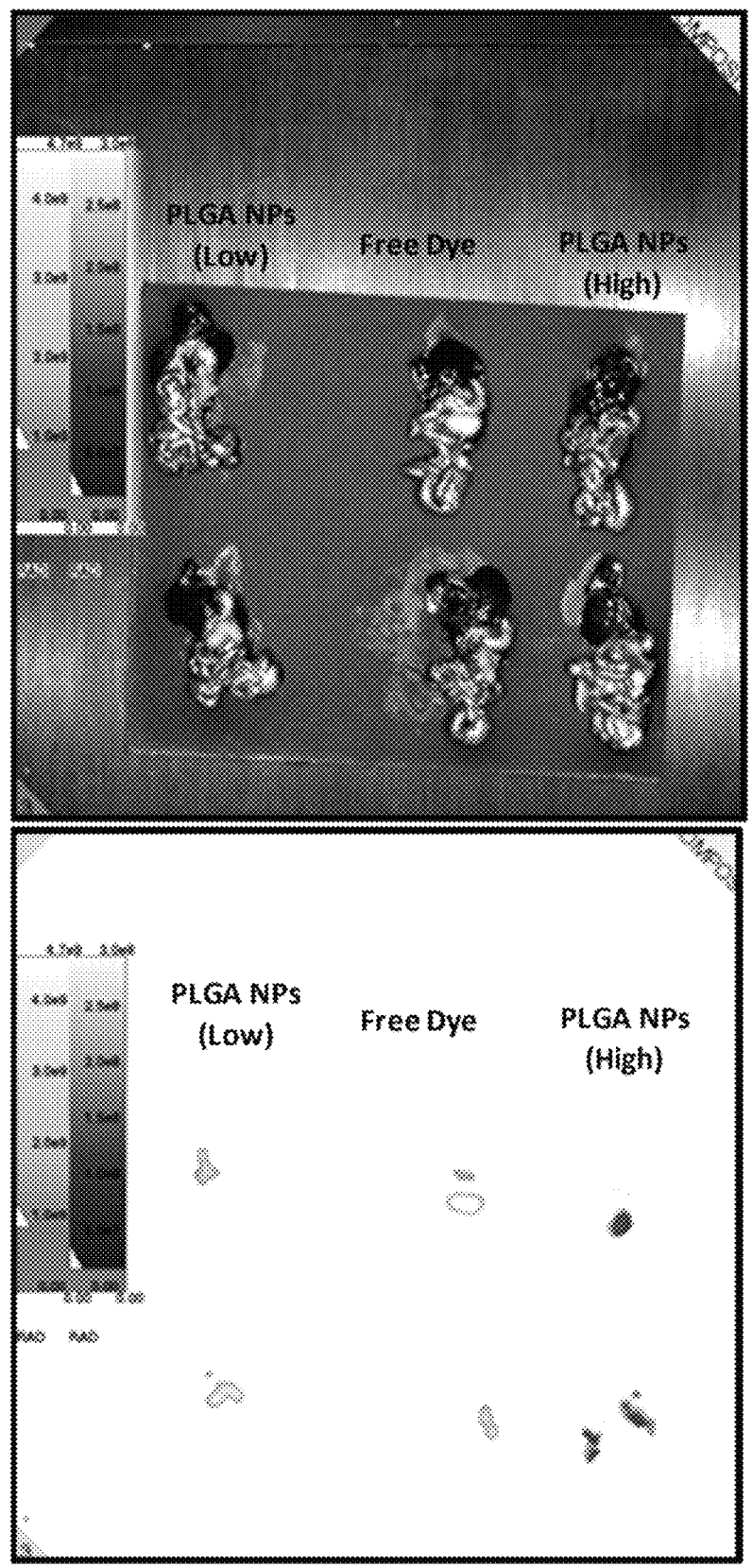
Figure 19:
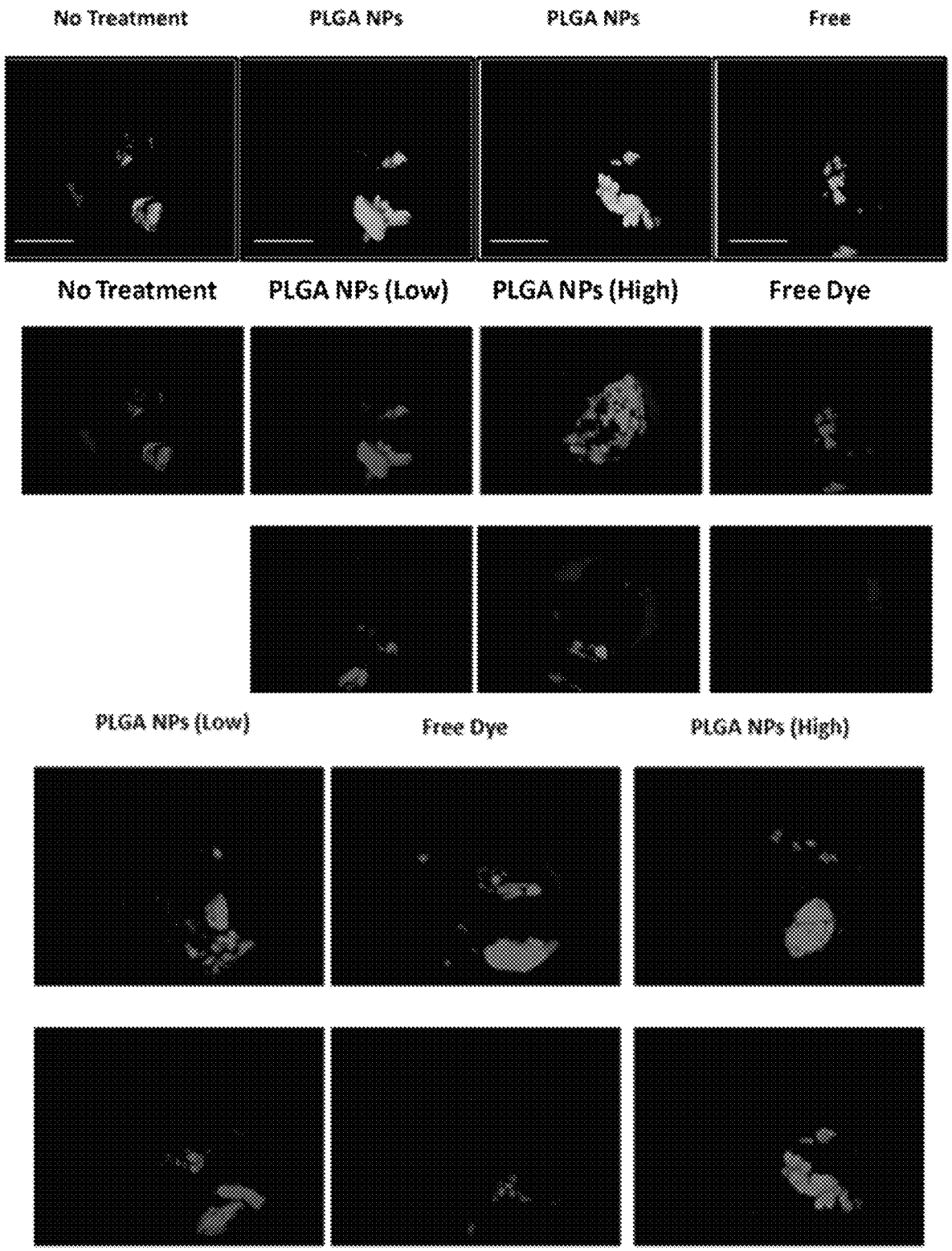
FIG. 19. Higher magnification imaging of PLGA NPs targeting TAMs at tumor sites.
Figure 20:
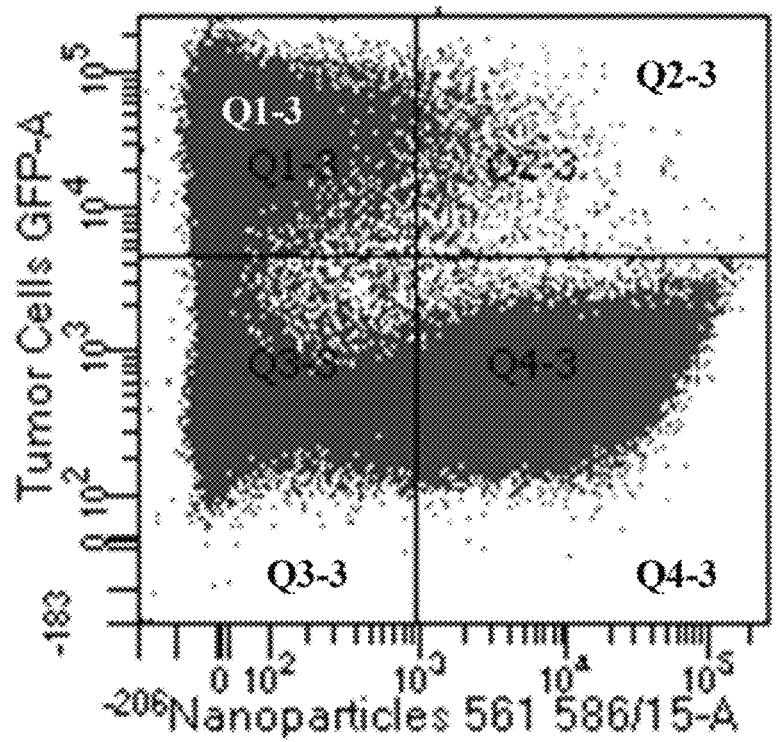
FIG. 20. EGFP-expressing human ovarian cancer cells (OVCAR8) were injected IP. After 21 days, 500 nm red fluorescent-labeled SiNPs were injected IP and then 4 days later the animals were euthanized and IP cavity tumors were removed, prepared as single cell suspension for flow cytometry. Flow cytometry analysis of cells in mice that take up SiNPs. The x-axis represents the amount of cells that uptake nanoparticles, while the y-axis depicts increasing tumor cell density. Q1 refers to tumor cells with no nanoparticles. Q2 refers to cancer cells with nanoparticles in the tumor. Q3 refers to non-cancerous cells, without nanoparticles. Q4 refers to cells with nanoparticles. This shows that almost all cells that uptake the SiNPs (97.5%) are not cancer cells.
Figure 21:
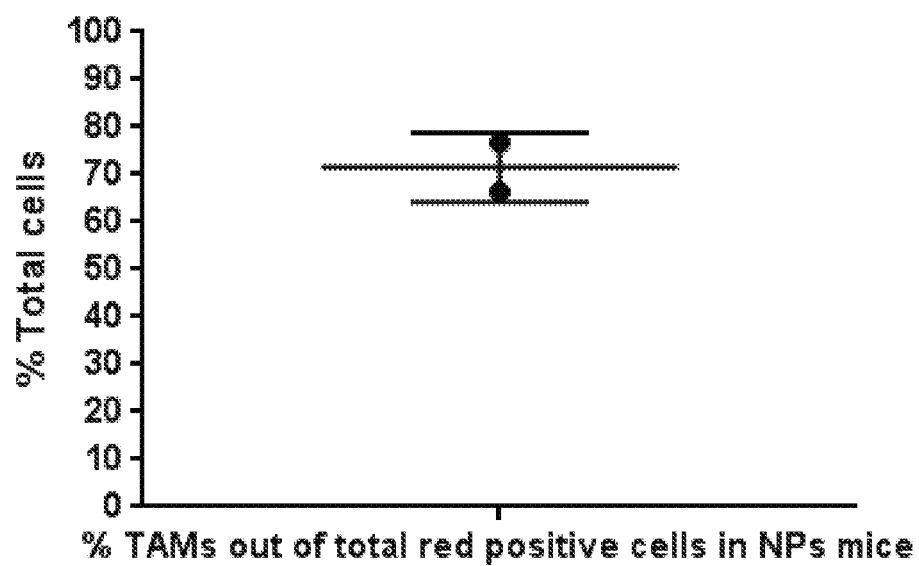
FIG. 21. Percentage of TAMs in red positive cells. EGFP-expressing human ovarian cancer cells (OVCAR8) were injected IP. After 21 days, 500 nm red fluorescent-labeled SiNPs were injected IP and then 4 days later the animals were euthanized and IP cavity tumors were removed, prepared as single cell suspension and stained with antibodies to CD45, CD1 b, f4-80 cell surface markers for flow cytometry. Flow cytometry analysis of cells in mice that take up SiNPs. ~70% of total cells that uptake the SiNPs in the tumor microenvironment are TAMs.
Figure 22:
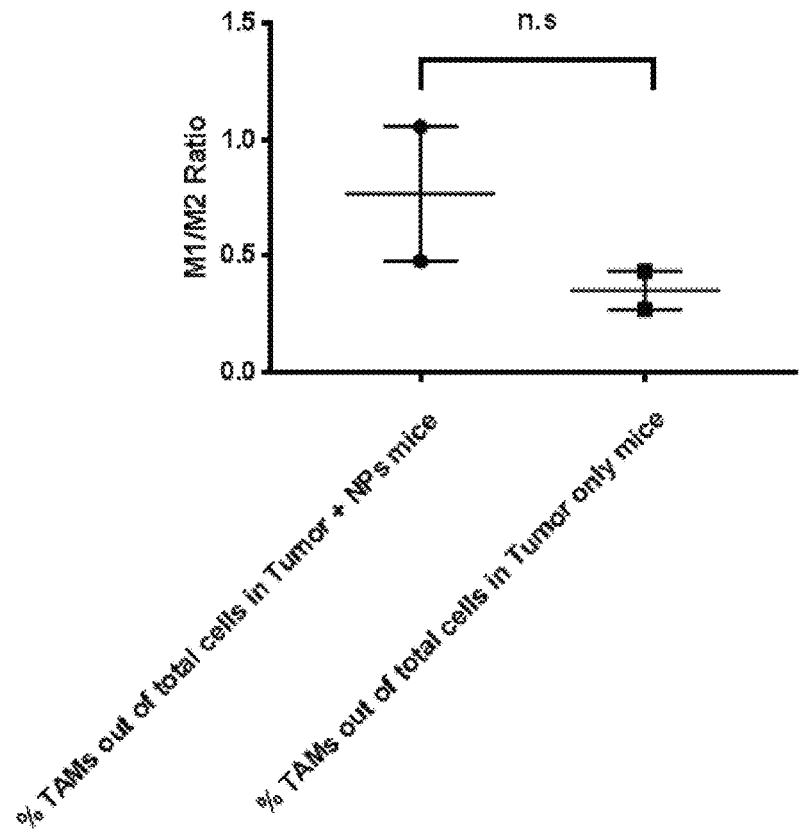
FIG. 22. Ratio of M1 TAMs (pro-inflammatory TAMs, which suppress cancer progression) to M2 TAMs (anti-inflammatory TAMs, which promote cancer progression). EGFP-expressing human ovarian cancer cells (OVCAR8) were injected IP. After 21 days, 500 nm red fluorescent-labeled SiNPs were injected IP and then 4 days later the animals were euthanized and IP cavity tumors were removed, prepared as single cell suspension and stained with antibodies to CD45, CD1 b, f4-80, CD206 and iNOS (i.e. biomarkers for macrophages) for flow cytometry. Flow cytometry analysis of cells in mice that take up SiNPs. The ratio of M1/M2 macrophages in tumor bearing mice that received the SiNP is higher than in tumor bearing mice without the NPs. The y-axis is the ratio—the % of M1 macrophages/% of M2 macrophages.
Figure 23:
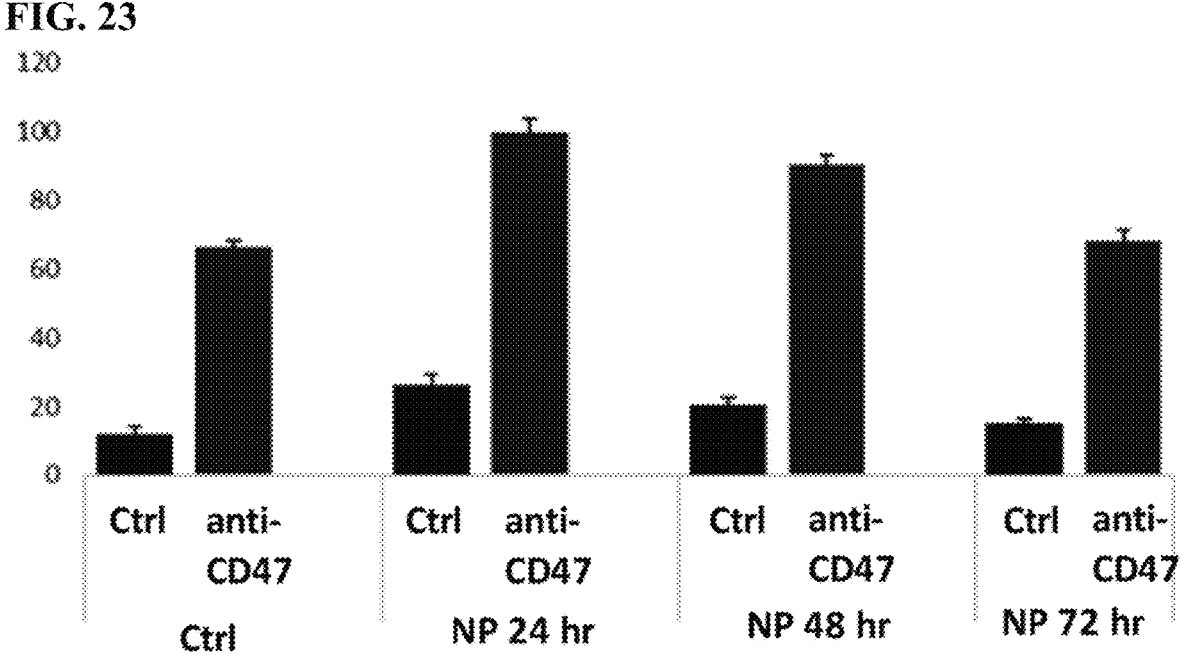
FIG. 23. Hydroxyl-SiNPs (also referred to herein as unfunctionalized silica nanoparticles) can increase phagocytosis of cancer cells by macrophages. Macrophages were treated with PBS (ctrl) or hydroxyl-SiNPs. This treatment was done without and with additional treatment with anti-CD47 antibody. The macrophages were then co-cultured with OVCAR8-GFP cells for 24 (ctrl and SiNP-treated), 48 (SiNP-treated only) or 72 hrs (SiNP-treated only). The hydroxyl-SiNPs induced the macrophages to phagocytose more cancer cells than Ctrl treatment and this effect was observed both without and with additional treatment with anti-CD47. The largest effect was for dual treatment with SiNPs and anti-CD47 antibody. The y-axis represents the percentage of cancer cells phagocytosed, normalized to 100%.

Therefore, we hypothesized that NPs of varied composition would show selective tumor targeting via TAM uptake so long as they are larger than ~100 nm, negatively charged, and IP injected. As one test of this claim, large polystyrene NPs ~800 nm in diameter and with a surface charge of −21.32 mV were injected IP into tumor-bearing mice, and IP cavity organs harvested after 4 days. Tissues were processed for confocal imaging, which confirmed that the polystyrene NPs were taken up by TAMs (FIG. 17A, 17B).

Figure 24:
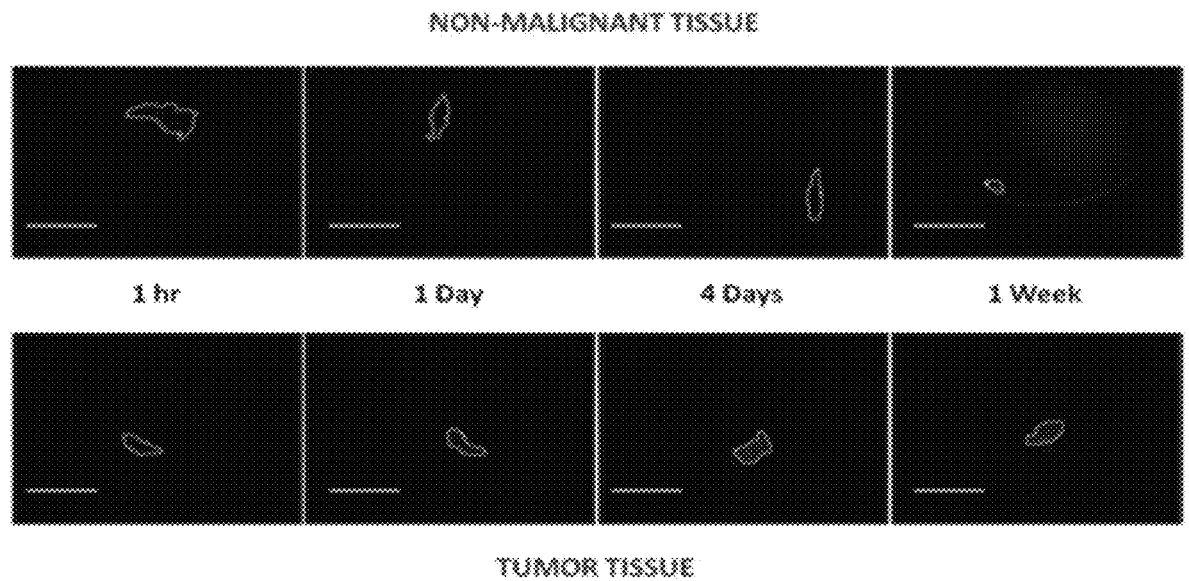
FIG. 24. Red fluorescent SiNPs can selectively detect human tumors by TAM uptake mechanism. Fresh tumors and non-malignant tissues were obtained from patients and incubated ex-vivo with red fluorescent SiNPs and imaged with Leica Z16 dissection macroscope after 1 hour, and 1, 4 and 7 days. Scale bar=1.0 cm.
Figure 25:
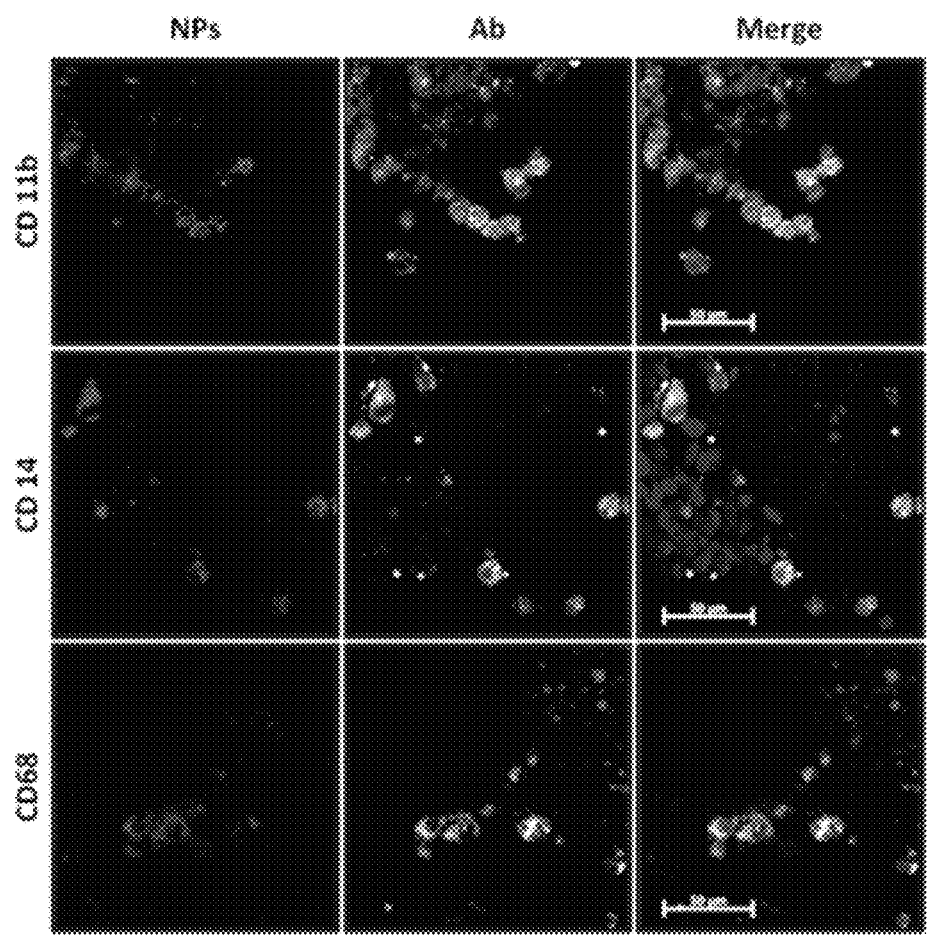
FIG. 25. Red fluorescent SiNPs can selectively detect human tumors by TAM uptake mechanism. Confocal images of representative sectioned tumors after 4 days of incubation with SiNPs (red), DAPI tumor nuclei (blue) anti-CD11b (myeloid cells marker), Anti-CD14 (monocytes and macrophages marker) and Anti-CD68 (myeloid cells marker) antibodies to identify TAMs (yellow). Scale bar=50 μm.
Figure 26:
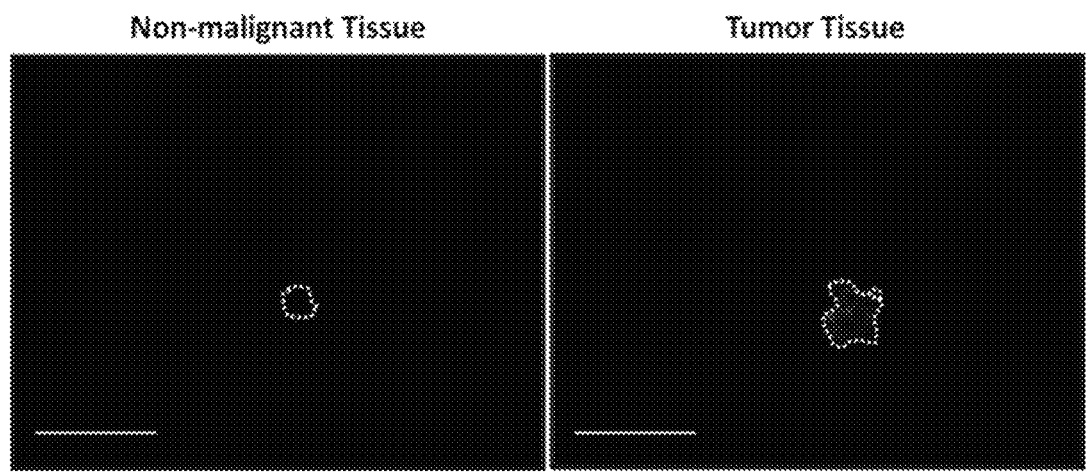
FIG. 26. The red fluorescently-labeled nanoparticles can selectively detect human tumors. Fresh tumors (A) Omentum and non-malignant tissues were obtained from patients and incubated ex-vivo with red fluorescently-labeled silica nanoparticles and imaged after 4 days. Tissues are marked in white dashed line, scale bar—1 cm (silica nanoparticles—red) (Leica Z16 dissection Macroscope).
Figure 26:
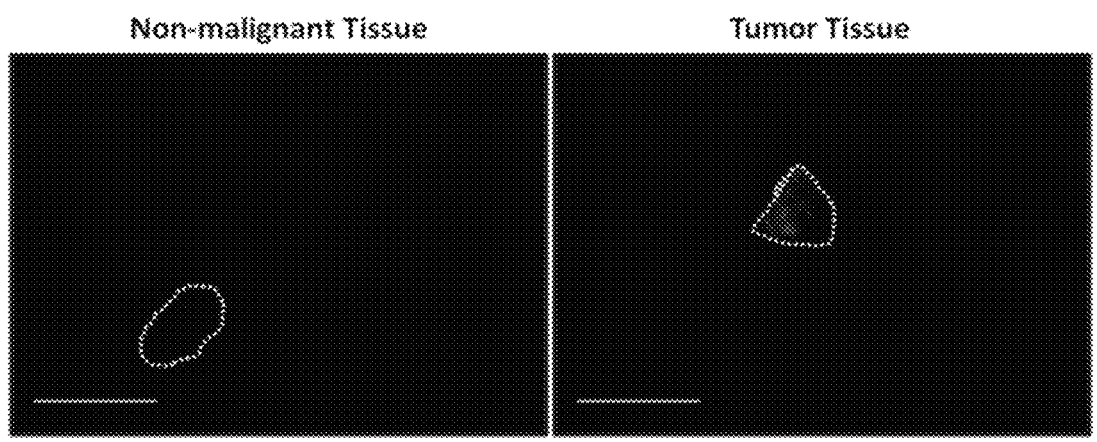
Figure 27:
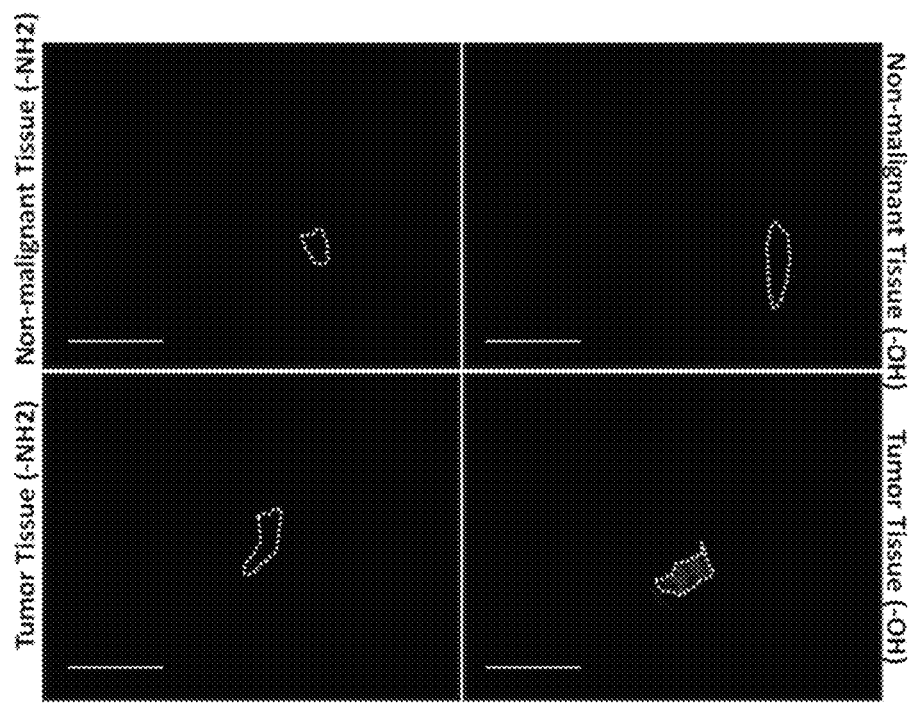
FIG. 27. The effect of surface charge on the selective tumor targeting of silica nanoparticles in human samples. Fresh tumors and non-malignant tissues were obtained from patients and incubated ex-vivo with negatively (—OH) and positively (—NH2) surface charged red fluorescently-labeled silica nanoparticles and imaged after 4 days. Tissues are marked in white dashed line, scale bar—1 cm (silica nanoparticles—red) (Leica Z16 dissection Macroscope).
Figure 28:
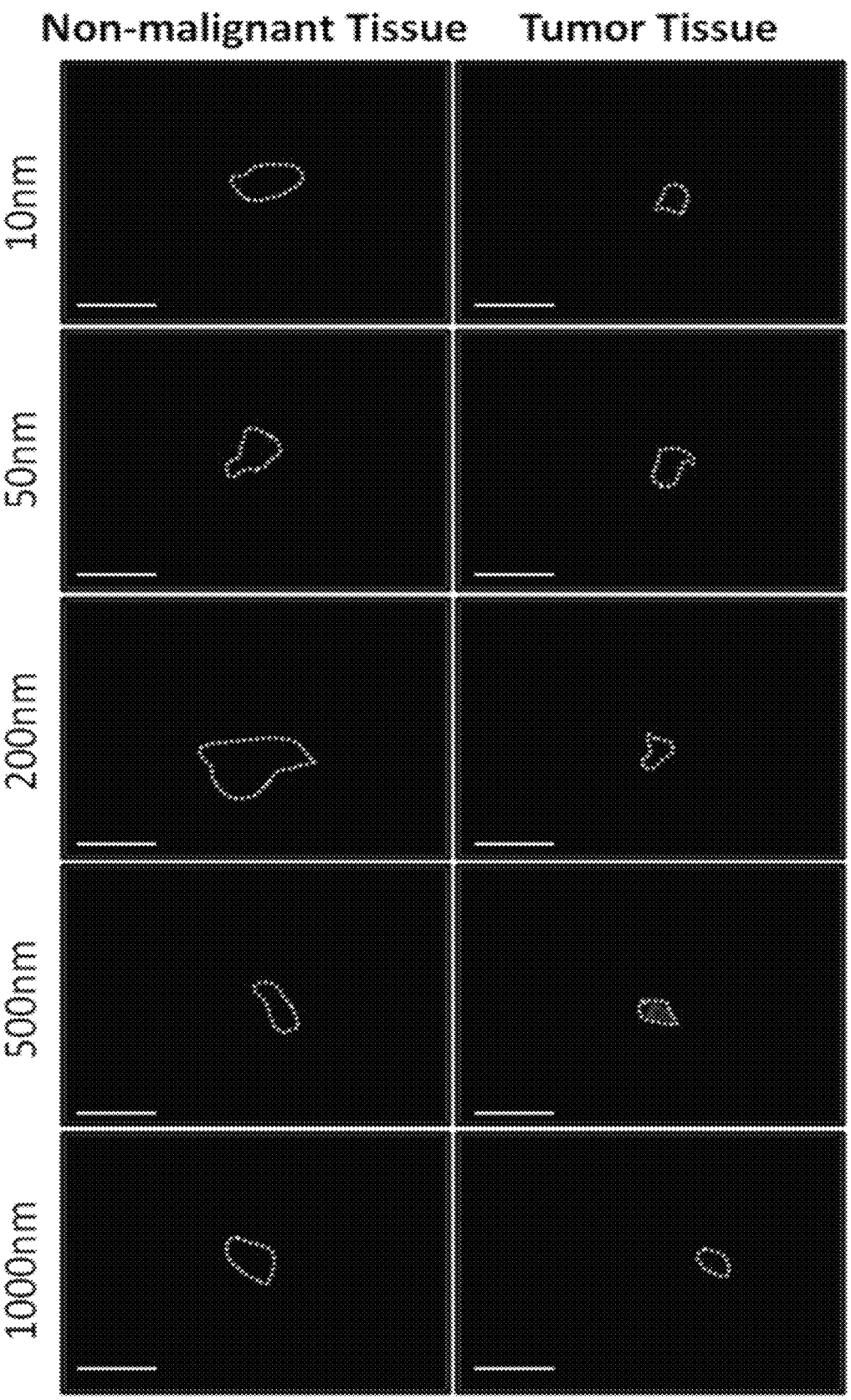
FIG. 28. The effect of silica nanoparticles' size on the selective tumor targeting of silica nanoparticles in human samples. Fresh tumors and non-malignant tissues were obtained from patients and incubated ex-vivo with 10, 50, 200, 500 and 1000 nm red fluorescently-labeled silica nanoparticles and imaged after 4 days. Tissues are marked in white dashed line, scale bar—1 cm (silica nanoparticles—red) (Leica Z16 dissection Macroscope).
Figure 29:
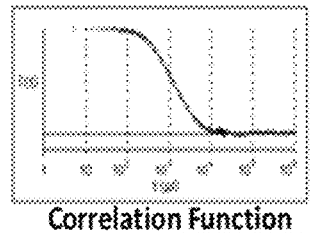
FIG. 29. PLGA nanoparticles with Imiquimod. The nanoparticle composition is 40 mg/mL PLGA 5% PVA (poly vinyl alcohol) with imiquimod.
Figure 29:
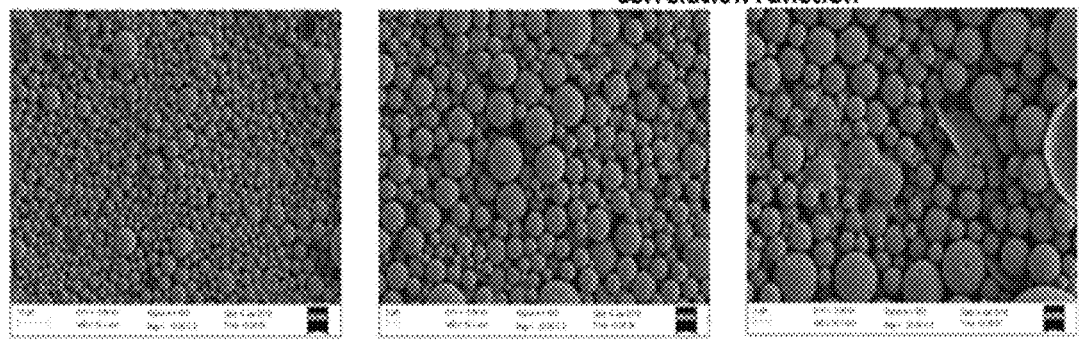

Finally, after demonstrating that 500 nm SiNPs with a hydroxyl surface (i.e. unfunctionalized) selectively label ovarian tumors in mice via uptake by TAMs and that this can be used to enhance surgical tumor reduction, we sought to determine if this phenomenon would also occur in human patients. Freshly excised tumor and non-malignant tissue samples were obtained from patients and incubated ex-vivo with fluorescent labeled SiNPs for 1 hour, and 1, 4 and 7 days. Remarkably, in all 10 cases, SiNPs selectively localized to the surface of metastatic tumor samples (collected from various locations including the diaphragm, omentum, colon and rectum) with minimal labeling of matched healthy tissue samples. Similar to the results in mice, the accumulation of SiNPs at tumor foci increased with incubation time, peaking at 4 days, with a strong signal still present at 7 days (FIG. 24). Moreover, only the anionic SiNPs targeted the human tumors (FIG. 27), and 500 nm was the optimal size (FIG. 28). In order to determine if this selective tumor accumulation was also due to uptake by TAMs, the tumors were fixed and processed for confocal imaging. The immunofluorescence staining results revealed co-localization of the red fluorescent SiNPs with CD11b+/CD14+/CD68+ cells, which are markers of human macrophages (FIG. 25).

In conclusion, several groups have shown tumor-specific targeting of non-targeted nanoparticles following IP administration and the presumption has been that this is due to uptake by tumor cells and often attributed to specific design features of the NPs. (6-10) Here we demonstrated that selective and efficient tumor labeling is achieved using simple, non-functionalized SiNPs provided they are sufficiently large, anionic, administered IP and imaging is performed at least 4 days after. We found that this is mediated by selective uptake by TAMs and the same phenomenon occurs with polystyrene NPs. Moreover, this result is observed not only in two mouse models of ovarian cancer but also in freshly excised human samples. We used these SiNPs as intraoperative fluorescent probes to improve surgery in a mouse model and in the near term we are excited about the potential to translate these particles to the clinic to enhance surgeons' abilities to remove extremely small tumors and enable accurate staging of the disease. Moreover, the ability to selectively target TAMs opens the door to a number of therapeutic strategies which will also be pursued.

The results also show that approximately 90% of the cells that uptake the unfunctionalized SiNP are positive for CD45 and CD11b.

Example 10: Materials and Methods

Nanoparticle characterization: The concentration of nanoparticles and their size (mean diameter) were measured using the NanoSight NS300 and analyzed with the nanoparticles tracking analysis software (Malvern NanoSight NS300 instrument, NTA software). Measurements were obtained by performing 3 runs of 60 seconds each, sample flow rate was controlled and kept constant (speed=30) during the acquisition using a syringe pump.

Dynamic light scattering (DLS) and Zeta potential measurements was performed on a Brookhaven 90 Plus/BI-MAS Instrument (Brookhaven Instruments, New York). DLS measurements were obtained by performing 5 runs at 30 s per run and Zeta potential measurements were obtained by performing 10 runs with 30 cycles per run.

Transmission electron microscopy (TEM) images were obtained with an FEI Tecnai T12 transmission electron microscope at an accelerating voltage of 120 keV and images were taken with a Gatan Ultrascan 2K CCD camera. The nanoparticles samples were imaged on 300 mesh carbon/formvar coated grids (Ted-Pella).

Cell Culture:

All cells were cultured and maintained at 37° C. in a humidified incubator containing 5% $CO_2$.

OVCAR8-GFP cells were cultured in Dulbecco's Modified Eagle's Medium (DMEM; Invitrogen, CA, USA) supplemented with 10% fetal bovine serum (Gemini Bio, CA, USA), 1% L-glutamine (Invitrogen) and 1% penicillin-streptomycin (Invitrogen). The cells were stably transduced with eGFP.

SKOV-3 cell line was obtained from American Type Culture Collection (ATCC) and was cultured, according to the ATCC protocol, in ATCC-formulated McCoy's 5a Medium Modified (ATCC) supplemented with 10% fetal bovine serum. The cells were stably transduced with eGFP to become GFP expressing cells (SKOV-3-GFP). When the cells reached 80% confluency, they were passaged using a 0.25% trypsin/EDTA solution (Invitrogen); media was changed every 2-3 days.

Imaging:

Spectral Ami-X In-vivo fluorescent whole-body imaging system was used to image the mice and the organs removed from the IP cavity (Spectral Instruments Imaging). The tumors were imaged at Ex: 465 nm, Em: 510 nm, and red fluorescently labeled nanoparticles were imaged at Ex: 570 nm, Em: 610 nm.

Confocal microscopic images were taken on a Zeiss LSM700 confocal microscope at 40×, 20× and 10×.

Leica Z16 dissection Macroscope was used to image the tissues that removed from the IP cavity with GFP-green filter cube (BP 527/30) and TX-red filter cube (645/75).

Au@Sinps Preparation:

Au@SiNPs were synthesized using a standard stober protocol for silica nanoparticles synthesis. 2 mL of Isopropanol were added to $9\times10^{10}$ 50 nm gold nanoparticles in 400 µL of water, and then 50 µL of ammonium hydroxide and 3.9 µL of tetraethyl-orthosilicate (TEOS) were added while stirring. After stirring for 1 hr at RT, the nanoparticles were centrifuge and washed 3 times with MilliQ water.

Amine-SiNP Nanoparticles:

A 25 mL round bottom flask with a magnetic stirring bar was flushed with nitrogen for 10 minutes. A dispersion of red silica nanoparticles (500 nm, $3.8\times10^{11}$ NPs) in 4 mL ethanol was added to the flask under nitrogen followed by the addition of 0.67 mL of aqueous ammonia. The final NP concentration was 10 g/L in the solution mixture with a final ammonia concentration of 4 vol. %. (3-Aminopropyl)triethoxysilane (APTES, 1uL) in 0.33 mL of EtOH was then added to the reaction mixture and it was stirred at room temperature overnight. The amount of APTES was calculated under the assumption that each APTES molecule takes up 0.6 $nm^2$ on the NP surface. To ensure the complete conversion of the hydroxyl groups to amine groups on the NP surface, a 7-fold excess of APTES was used in the reaction. The following day, the reaction was refluxed at 85° C. while stirring for 2 h. The resulting NPs in the dispersion were collected and washed by repeated centrifugation at 21,000 g, 1 min (3 washes in EtOH, followed by 3 washes in MilliQ water). SiNP—$NH_2$ was redispersed in MilliQ water and stored at 4° C.

PEG-SiNP nanoparticles: A water dispersion of SiNP—$NH_2$ containing $1.9 \times 10^{11}$ NPs was exchanged to PBS solution by 3 repeated centrifugation cycles at 21,000 g, 1 min in PBS. A 25-fold molar excess of sulfo-SMCC solution in PBS was added to the SiNP—$NH_2$ and the mixture was shaken at 37° C. for 1 hr. To remove the salts and excess sulfo-SMCC, SiNPs were pelleted and washed 3 times with MilliQ water by centrifugation (21,000 g, 1 min). The resulting SiNP-Mal particles were redispersed in MilliQ water and washed 3 times with PBS to convert their solvent to PBS followed by the addition of a PEG-SH solution in PBS. The mixture was placed in a shaker and incubated at 37° C. overnight. It was assumed that each maleimide group on the NP surface takes up 0.6 $nm^2$ and each maleimide functional group reacts with one thiol group on the PEG-SH molecules. To maximize PEG coverage on the NP surface, 10-fold molar excess of PEG-SH to the number of maleimide groups on the SiNP surface was used in the reaction. Upon reaction completion, PEGylated SiNPs were collected and washed by repeated centrifugation at 21,000 g for 1 min (3 times with MilliQ water). PEGylated SiNPs were resuspended in MilliQ water and stored at 4° C.

Animal Experiments:

All animals were maintained under specific pathogen-free conditions at the City of Hope Animal Resource Center, and all procedures were reviewed and approved by the City of Hope Animal Care and Use Committee.

Different Surface Counting and Charge:

Female, athymic nude mice (Charles River) that were 7 weeks old were inoculated with 2 million OVCAR8-GFP cells via intraperitoneal injection. After 21 days, mice (n=5 per group) were IP injected with: $1.37*10^{10}$ 500 nm red fluorescently-labeled hydroxyl-SiNP (Micromod Partikeltechnologie GmbH) in 1 mL PBS, $1.37*10^{10}$ Amine-red-fluorescently labeled SiNP in 1 mL PBS or $1.37*10^{10}$ PEG-red-fluorescently labeled SiNP in 1 mL PBS. Control mice received 1 mL PBS injection. After 4 days the mice were euthanized, the organs in the IP cavity were removed and a fluorescent whole-body imaging system was used (Spectral Ami-X, Spectral Instruments Imaging). The tumors and adjacent healthy tissues were then remove and prepared for confocal imaging.

Kinetics of Attachment:

Female, athymic nude mice (Charles River) that were 7 weeks old were inoculated with 2 million OVCAR8-GFP cells via intraperitoneal injection. After 21 days, mice (n=4 per group) were IP injected with $1.37*10^{10}$ 500 nm Red-fluorescently labeled SiNP (Micromod Partikeltechnologie GmbH) in 1 mL PBS. Control mice received 1 mL PBS injection. After 1, 5, 24 hours and 4 days the mice were euthanized, the organs in the IP cavity were removed and a fluorescent whole-body imaging system was used (Spectral Ami-X, Spectral Instruments Imaging). The tumors and adjacent healthy tissues were then remove and prepared for confocal imaging.

Different Size Assessment:

Female, athymic nude mice (Charles River) that were 7 weeks old were inoculated with 2 million OVCAR8-GFP cells via intraperitoneal injection. After 21 days, mice (n=5 per group) were IP injected with 10 nm, 50 nm, 200 nm, 500 nm and 1000 nm Red-fluorescently labeled SiNP (Micromod Partikeltechnologie GmbH) in 1 mL PBS (HD size measured by DLS: 24.6 nm, 54.7 nm, 194.8 nm, 443.9 nm and 982.9 nm and zeta potential measured: −24.22 mV, −23.19 mV, −37.12 mV, −54.59 mV, −73.71 mV). Control mice received 1 mL PBS injection. All the nanoparticles samples were compared and normalized based on their fluorescence intensity as measured by a fluorimeter, and not by nanoparticles number (as was done in other experiments) or mass. Since both the Spectral Ami-X and the Leica Z16 dissection Macroscope measure the fluorescence intensity, normalizing the injected dose by nanoparticles number will be favored for the large nanoparticles, and normalizing the groups by mass will be favored for the small nanoparticles. After 4 days the mice were euthanized, the organs in the IP cavity were removed and a fluorescent whole-body imaging system was used (Spectral Ami-X, Spectral Instruments Imaging). The organs from the IP cavity were also imaged by Leica Z16 dissection Macroscope. The tumors and adjacent healthy tissues were then remove and prepared for confocal imaging.

Administration Route Assessment:

Female, athymic nude mice (Charles River) that were 7 weeks old were inoculated with 2 million OVCAR8-GFP cells via intraperitoneal injection. After 21 days, mice (n=5 per group) were IP injected with $1.37*10^{10}$ Red-fluorescently labeled SiNP (Micromod Partikeltechnologie GmbH) in 1 mL PBS. Control mice received 1 mL PBS injection. The IV administration group was IV injected to the tail vain with $1.52*10^9$ (1 mg/mL) 500 nm Red-fluorescently labeled SiNP in 0.2 mL PBS. Control mice of that group received 0.2 mL PBS injection. The IV administration group received a lower amount of nanoparticles since it is not recommended to inject IV more than 0.2 mL and higher concentrations than 1 mg/mL. After 4 days the mice were euthanized, the organs in the IP cavity were removed and a fluorescent whole-body imaging system was used (Spectral Ami-X, Spectral Instruments Imaging). The organs from the IP cavity were also imaged by Leica Z16 dissection Macroscope. The tumors and adjacent healthy tissues were then remove and prepared for confocal imaging.

Different Ovarian Cancer Cell Lines:

Female, athymic nude mice (Charles River) that were 7 weeks old were inoculated with 2 million OVCAR8-GFP or Skov-3-GFP cells via intraperitoneal injection. After 21 days, mice (n=5 per group) were IP injected with $1.37*10^{10}$ 500 nm Red-fluorescently labeled SiNP (Micromod Partikeltechnologie GmbH) in 1 mL PBS. Control mice received 1 mL PBS injection. After 4 days the mice were euthanized, the organs in the IP cavity were removed and a fluorescent whole-body imaging system was used (Spectral Ami-X, Spectral Instruments Imaging). The organs from the IP cavity were also imaged by Leica Z16 dissection Macroscope. The tumors and adjacent healthy tissues were then removed and prepared for confocal imaging.

In Vivo Biodistribution Study:

Female, athymic nude mice (Charles River) that were 7 weeks old were inoculated with 2 million OVCAR8-GFP cells via intraperitoneal injection. After 21 days, mice (n=4 per group) were IP injected with 1.37*10$^{10}$ Au@SiNPs in 1 mL PBS. Control group received 1 mL PBS injection. After 4 days the mice were euthanized and the liver, spleen, kidneys, stomach, lungs, intestines and tumors were collected from the peritoneal cavity of each animal from each treatment group and placed into 50 mL or 15 mL metal-free plastic tubes. The samples were stored in a −20° C. freezer until preparation for ICP-MS analysis. For ICP-MS analysis, the samples were digested directly in the tubes by adding a mixture of concentrated acids (68% $HNO_3$, 1% HCl, 0.2% HF) and incubating overnight in an oil bath at 80° C. (Table 2). As a control for the total amount of Au@SiNPs injected per mouse (100% injected dose), the same volume and concentration of Au@SiNPs injected was similarly digested. The samples were serially diluted 1000-fold with a 2% $HNO_3$ 1% HCl solution to minimize the final concentration of HF, and then analyzed on an Agilent 8800 ISIS in no gas mode to determine gold concentration. The total amount of gold was calculated by multiplying the measured concentration (ppb) with the total volume of sample after dilutions, then normalized to the 100% injected dose of Au@SiNPs.

Polystyrene In-Vivo Study:

Female, athymic nude mice (Charles River) that were 7 weeks old were inoculated with 2 million OVCAR8-GFP cells via intraperitoneal injection. After 21 days, mice (n=5 per group) were IP injected with polystyrene nanoparticles loaded with nile red (SPHERO™ Fluorescent Particles FP-3056-2, Sphereotech, IL, USA). These particles had an effective particle diameter of 798 nm (0.0137 polydispersity index value) and surface charge of (−21.32±3.20 mV) as assessed by dynamic light scattering and zeta potential measurements (n=5). Control mice received 1 mL PBS injection. After 4 days the tumors and adjacent healthy tissues were remove and prepared for confocal imaging.

Immunofluorescent Staining:

Organ collected from the IP cavity were placed in 4% PFA solution for 3 days at 4° C. in the dark, washed with PBS 3 times, stored in 30% sucrose solution at 4° C. for 3 days. The tissues were embedded in Optimal Cutting Temperature (OCT) medium just prior to sectioning using a cryostat. The sections thickness was 10 m, and they were mounted on superfrost plus slides (Thermo Fisher Scientific, Australia) and stored at −20° C. All sections were blocked for 30 min at RT with blocking solution (PBS containing 1% BSA, 10% FBS, 0.2% Saponin). Sections were then incubated overnight at 4° C. with the primary antibodies diluted in blocking buffer: Rat anti-mouse CD11b (Biolegend), Rat anti-mouse F4/80 (Biolegend), Rat anti-mouse GR1 (bdbiosciences), Rat anti-mouse CD45 (Biolegend), Rat anti-human CD11b (Biolegend), Mouse anti-human CD68 (Biolegend), Mouse anti-human CD14 (Biolegend).

Sections were washed five times with PBST for 5 min each and incubated with the secondary antibody for 1 hour at RT: Alexa Fluor 647 Goat anti-rat (invitrogen) or Alexa Fluor 647 Goat anti-mouse (Biolegend).

Sections were then washed three times with PBST for 5 min each, and stained with Dapi solution for 5 min at room temperature (RT). Sections were then washed three times with PBST for 5 min each.

Fluorescence mounting medium (Dako) was applied before slides were cover-slipped and stored at 4° C. until imaging.

Human Tissue Procurement and Processing:

Fresh tumors and non-malignant tissues were obtained from patients who gave institutional review board (IRB)-approved informed consent [City of Hope (COH) IRB 15280] before tissue collection at the City of Hope Medical Center, the fresh tumors and non-malignant tissues were incubated in 1.5 mg/mL solution of 500 nm red fluorescently-labeled SiNP (Micromod Partikeltechnologie GmbH) in 4 mL DMEM media. 1 hr, 1, 4 and 7 days later the tissues were washed in PBS 3 times, were placed in a new plate and imaged with the Leica Z16 dissection Macroscope. The preparation of human tumors for confocal imaging was done the same way as the preparation of mice organs for confocal imaging.

Statistical Analysis:

Data are presented as mean±SEM unless otherwise stated. Statistical significance was determined using a two-tailed students t-test (* $p<0.05$) unless otherwise stated.

Materials:

ICP-MS grade nitric acid (70%), hydrochloric acid (37%), and hydrofluoric acid (50%) were purchased from BD Aristar. 50 mL and 15 mL metal-free plastic tubes were purchased from SCP Science. 100 µg mL$^1$ gold standard was purchased from Spex Certiprep.

General Methods:

A stock solution of 2% $HNO_3$ 1% HCl solution was made by adding 28 mL $HNO_3$ (70%) and 27 mL HCl (37%) to 945 mL milliQ $H_2O$ and stored in a plastic bottle. A stock solution of concentrated acid (68% $HNO_3$ 1% HCl) was made fresh by adding 0.27 mL HCl (37%) to every 10 mL $HNO_3$ (70%). To prepare the samples for ICP-MS analysis, the standard method was to add 500 µL of the acid blend, then 2 µL of HF (50%) directly into each tube containing sample. For the control, the 100% injected dose (1 mL) of Au@SiNPs solution was split into two 500 µL aliquots and similarly digested. For the tumors, liver, and intestines, additional acid was required to completely digest the organs; the additional acid was added at a fixed ratio of 500 µL acid blend plus 2 µL HF (Table 2). The tubes containing samples in acid were incubated at 80° C. in an oil bath overnight to allow maximal digestion. After digestion, the samples were serially diluted 1000× with a 2% $HNO_3$ 1% HCl solution by first diluting 10× in the same tube, then aliquoting 100 µL sample into a new 15 mL metal-free tube and diluting 100× to a final volume of 10 mL (Table 2). This dilution was chosen so that the final concentration of HF would be at the acceptable working limits for the ICP-MS instrument (0.0002%). For the intestines, undigestable material remained after overnight digestion which required a centrifugation step during serial dilution to remove. Briefly, 2 mL of sample was taken after the 10× dilution step and centrifuged at 21130 g for 5 minutes, then 100 µL of the supernatant was taken for the 100× dilution step. A standard curve ranging from 0.195 to 500 ppb (0.5 ng mL$^{-1}$) was made using a serial dilution of a 100 ppm (100 µg mL$^{-1}$) gold standard (Spex Certiprep) in a 2% $HNO_3$ 1% HCl solution. Samples were analyzed on an Agilent 8800 ISIS (discrete sampling) in no gas mode to determine gold concentration. Rinse solution was 2% $HNO_3$ and carrier solution was 2% $HNO_3$ 1% HCl. Each sample was measured by the instrument 5 times (technical replicates). A blank solution and calibration standard was measured after approximately every 10 samples to ensure that there was no carry-over between samples, and to check for instrument consistency. The total amount of gold was calculated by multiplying the measured concentration (ppb) with the calculated total volume of sample after dilutions, then normalized to the 100% injected dose of Au@SiNPs. Measurements below the lower limit of the standard curve were considered to be zero.

TABLE 2

Reagent calculations for the volumes of concentrated acid needed to digest each sample and the volume of 2% HNO3 1% HCl needed to dilute each sample. The calculated final volume after dilution was used to calculate the total amount (ng) of gold in each sample.

| Sample | vol HNO₃ HCl (mL) | vol HF (uL) | vol added (mL) | final (mL) | 10x dilution vol taken (uL) | vol added (mL) | 100x dilution Final vol (mL) |
|---|---|---|---|---|---|---|---|
| intestine | 2 | 8 | 18 | 20 | 100 | 9.9 | 2000 |
| liver | 1 | 4 | 9 | 10 | 100 | 9.9 | 1000 |
| tumor | 1 | 4 | 9 | 10 | 100 | 9.9 | 1000 |
| lung | 0.5 | 2 | 4.5 | 5 | 100 | 9.9 | 500 |
| kidney | 0.5 | 2 | 4.5 | 5 | 100 | 9.9 | 500 |
| spleen | 0.5 | 2 | 4.5 | 5 | 100 | 9.9 | 500 |
| stomach | 0.5 | 2 | 4.5 | 5 | 100 | 9.9 | 500 |
| injected NP dose (50%) | 0.5 | 2 | 4.5 | 5 | 100 | 9.9 | 500 (1000 for 100% dose) |

REFERENCES

1. "Survival rates for ovarian cancer" website http://www.cancer.org/cancer/ovariancancer/overviewguide/ovarian-cancer-overview-survival.
2. O. Z. D. S. Chi, Surgical Resection and Reconstruction for Advanced and Recurrent Gynecologic Malignancies. *Expert Review of Obstetrics & Gynecology* 3, 14 (2008).
3. D. K. Armstrong, Relapsed ovarian cancer: challenges and management strategies for a chronic disease. *The oncologist* 7 Suppl 5, 20 (2002).
4. O. W. Foley, J. A. Rauh-Hain, M. G. del Carmen, Recurrent epithelial ovarian cancer: an update on treatment. *Oncology* 27, 288 (April, 2013).
5. G. M. van Dam et al., Intraoperative tumor-specific fluorescence imaging in ovarian cancer by folate receptor-alpha targeting: first in-human results. *Nature medicine* 17, 1315 (Sep. 18, 2011).
6. Z. Lu et al., Tumor-penetrating microparticles for intraperitoneal therapy of ovarian cancer. *The Journal of pharmacology and experimental therapeutics* 327, 673 (December, 2008).
7. T. Kamei et al., Spatial distribution of intraperitoneally administrated paclitaxel nanoparticles solubilized with poly (2-methacryloxyethyl phosphorylcholine-co n-butyl methacrylate) in peritoneal metastatic nodules. *Cancer science* 102, 200 (January, 2011).
8. D. Soma et al., Intraperitoneal administration of paclitaxel solubilized with poly(2-methacryloxyethyl phosphorylcholine-co n-butyl methacrylate) for peritoneal dissemination of gastric cancer. *Cancer science* 100, 1979 (October, 2009).
9. A. J. Di Pasqua et al., Neutron-activatable holmium-containing mesoporous silica nanoparticles as a potential radionuclide therapeutic agent for ovarian cancer. *Journal of nuclear medicine: official publication, Society of Nuclear Medicine* 54, 111 (January, 2013).
10. A. H. Colby et al., Highly Specific and Sensitive Fluorescent Nanoprobes for Image-Guided Resection of Sub-Millimeter Peritoneal Tumors. *ACS nano* 11, 1466 (Feb. 28, 2017).
11. P. Cao et al., Intraperitoneal Administration of Neural Stem Cell-Nanoparticle Conjugates Targets Chemotherapy to Ovarian Tumors. *Bioconjugate chemistry*, (May 18, 2017).
12. C. Caltagirone, A. Bettoschi, A. Garau, R. Montis, Silica-based nanoparticles: a versatile tool for the development of efficient imaging agents. *Chemical Society reviews* 44, 4645 (Jul. 21, 2015).
13. E. Phillips et al., Clinical translation of an ultrasmall inorganic optical-PET imaging nanoparticle probe. *Science translational medicine* 6, 260ra149 (Oct. 29, 2014).
14. A. C. Anselmo, S. Mitragotri, Nanoparticles in the clinic. *Bioengineering & Translational Medicine* 1, 10 (2016).
15. T. A. Wynn, A. Chawla, J. W. Pollard, Macrophage biology in development, homeostasis and disease. *Nature* 496, 445 (Apr. 25, 2013).
16. S. I. Grivennikov, F. R. Greten, M. Karin, Immunity, inflammation, and cancer. *Cell* 140, 883 (Mar. 19, 2010).
17. B. Z. Qian, J. W. Pollard, Macrophage diversity enhances tumor progression and metastasis. *Cell* 141, 39 (Apr. 2, 2010).
18. S. M. Zeisberger et al., Clodronate-liposome-mediated depletion of tumour-associated macrophages: a new and highly effective antiangiogenic therapy approach. *British journal of cancer* 95, 272 (Aug. 7, 2006).
19. R. A. Franklin et al., The cellular and molecular origin of tumor-associated macrophages. *Science* 344, 921 (May 23, 2014).
20. J. Feng et al., Effects of size and targeting ligand on biodistribution of liposome nanoparticles in tumor mice. *J NUCL MED MEETING ABSTRACTS* 54, 1339 (May 1, 2013, 2013).

What is claimed is:

1. A method of delivering an anti-cancer agent or detectable agent to a tumor associated macrophage of a subject in need thereof, said method comprising intraperitoneally administering to said subject a therapeutically effective amount of an anionic non-functionalized nanoparticle composition wherein the nanoparticle comprises the anti-cancer agent or detectable agent, wherein the average longest dimension of the nanoparticle composition is from about 400 nm to about 800 nm, thereby delivering said anti-cancer agent or detectable agent to said tumor associated macrophage of said subject.

2. The method of claim 1, wherein the nanoparticle composition increases the level or activity of T cells, B cells, or macrophages.

3. The method of claim 1, wherein the average longest dimension of the nanoparticle composition is about 500 nm.

4. The method of claim 1, wherein the nanoparticle comprises silica, iron, gold, poly(lactic-co-glycolic acid) (PLGA), phospholipid, or polystyrene.

5. The method of claim 1, wherein the anti-cancer agent is imiquimod, resiquimod, or oseltamivir.

6. The method of claim 1, wherein said anticancer agent is a nucleic acid, antibody, polymer, protein, steroid, or a small molecule.

7. The method of claim 1, wherein said anti-cancer agent is a JAK2 inhibitor, a STAT3 inhibitor, an interferon, a CpG oligodeoxynucleotide (CpG ODN), a cytotoxic agent, tumor necrosis factor alpha (TNFα), tumor necrosis factor beta (TNFβ), a cyclic dinucleotide, or a Granulocyte-macrophage colony-stimulating factor (GM-CSF).

8. The method of claim 1, wherein the detectable agent comprises a fluorescent dye, an enzyme used in an ELISA, a paramagnetic molecule, a radioisotope or radionuclide, or an iodinated contrast agent.

* * * * *

SEQUENCE LISTING

<160> NUMBER OF SEQ ID NOS: 21

<210> SEQ ID NO 1
<211> LENGTH: 50
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: residues modified by phosphorothioate linkage
<220> FEATURE:
<221> NAME/KEY: misc_feature
<222> LOCATION: (16)..(19)
<223> OTHER INFORMATION: residues modified by phosphorothioate linkage -continued

```
<220> FEATURE:
<221> NAME/KEY: misc_feature
<222> LOCATION: (20)..(21)
<223> OTHER INFORMATION: (-(CH2)3-)5
<220> FEATURE:
<221> NAME/KEY: misc_feature
<222> LOCATION: (21)..(23)
<223> OTHER INFORMATION: residues modified by phosphorothioate linkage
<220> FEATURE:
<221> NAME/KEY: misc_feature
<222> LOCATION: (35)..(36)
<223> OTHER INFORMATION: (-(CH2)3-)4
<220> FEATURE:
<221> NAME/KEY: misc_feature
<222> LOCATION: (47)..(49)
<223> OTHER INFORMATION: residues modified by phosphorothioate linkage
<220> FEATURE:
<221> NAME/KEY: misc_feature
<222> LOCATION: (50)..(50)
<223> OTHER INFORMATION: (-(CH2)3-)5-NH2

<400> SEQUENCE: 1
ggtgcatcga tgcaggggggg catttcccgt aaatcgattt acgggaaatg              50

<210> SEQ ID NO 2
<211> LENGTH: 50
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: residues modified by phosphorothioate linkage
<220> FEATURE:
<221> NAME/KEY: misc_feature
<222> LOCATION: (16)..(19)
<223> OTHER INFORMATION: residues modified by phosphorothioate linkage
<220> FEATURE:
<221> NAME/KEY: misc_feature
<222> LOCATION: (20)..(21)
<223> OTHER INFORMATION: (-(CH2)3-)5
<220> FEATURE:
<221> NAME/KEY: misc_feature
<222> LOCATION: (21)..(23)
<223> OTHER INFORMATION: residues modified by phosphorothioate linkage
<220> FEATURE:
<221> NAME/KEY: misc_feature
<222> LOCATION: (35)..(36)
<223> OTHER INFORMATION: (-(CH2)3-)4
<220> FEATURE:
<221> NAME/KEY: misc_feature
<222> LOCATION: (47)..(49)
<223> OTHER INFORMATION: residues modified by phosphorothioate linkage
<220> FEATURE:
<221> NAME/KEY: misc_feature
<222> LOCATION: (50)..(50)
<223> OTHER INFORMATION: (-(CH2)3-)5-NH2

<400> SEQUENCE: 2
ggtgcatgca tgcaggggggg catttcccgt aaatcgattt acgggaaatg              50

<210> SEQ ID NO 3
<211> LENGTH: 50
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: residues modified by phosphorothioate linkage
```

```
<220> FEATURE:
<221> NAME/KEY: misc_feature
<222> LOCATION: (16)..(19)
<223> OTHER INFORMATION: residues modified by phosphorothioate linkage
<220> FEATURE:
<221> NAME/KEY: misc_feature
<222> LOCATION: (20)..(21)
<223> OTHER INFORMATION: (-(CH2)3-)5
<220> FEATURE:
<221> NAME/KEY: misc_feature
<222> LOCATION: (21)..(23)
<223> OTHER INFORMATION: residues modified by phosphorothioate linkage
<220> FEATURE:
<221> NAME/KEY: misc_feature
<222> LOCATION: (35)..(36)
<223> OTHER INFORMATION: (-(CH2)3-)4
<220> FEATURE:
<221> NAME/KEY: misc_feature
<222> LOCATION: (47)..(49)
<223> OTHER INFORMATION: residues modified by phosphorothioate linkage
<220> FEATURE:
<221> NAME/KEY: misc_feature
<222> LOCATION: (50)..(50)
<223> OTHER INFORMATION: (-(CH2)3-)5-NH2

<400> SEQUENCE: 3
ggtgcatcga tgcagggggg actcttgcca attacgtaat tggcaagagt            50

<210> SEQ ID NO 4
<211> LENGTH: 50
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: residues modified by phosphorothioate linkage
<220> FEATURE:
<221> NAME/KEY: misc_feature
<222> LOCATION: (20)..(21)
<223> OTHER INFORMATION: (-(CH2)3-)5
<220> FEATURE:
<221> NAME/KEY: misc_feature
<222> LOCATION: (21)..(23)
<223> OTHER INFORMATION: residues modified by phosphorothioate linkage
<220> FEATURE:
<221> NAME/KEY: misc_feature
<222> LOCATION: (35)..(36)
<223> OTHER INFORMATION: (-(CH2)3-)4
<220> FEATURE:
<221> NAME/KEY: misc_feature
<222> LOCATION: (47)..(49)
<223> OTHER INFORMATION: residues modified by phosphorothioate linkage
<220> FEATURE:
<221> NAME/KEY: misc_feature
<222> LOCATION: (50)..(50)
<223> OTHER INFORMATION: (-(CH2)3-)5-NH2

<400> SEQUENCE: 4
tccatgacgt tcctgatgct catttcccgt aaatcgattt acgggaaatg            50

<210> SEQ ID NO 5
<211> LENGTH: 50
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: residues modified by phosphorothioate linkage
```

-continued

```
<220> FEATURE:
<221> NAME/KEY: misc_feature
<222> LOCATION: (20)..(21)
<223> OTHER INFORMATION: (-(CH2)3-)5
<220> FEATURE:
<221> NAME/KEY: misc_feature
<222> LOCATION: (21)..(23)
<223> OTHER INFORMATION: residues modified by phosphorothioate linkage
<220> FEATURE:
<221> NAME/KEY: misc_feature
<222> LOCATION: (35)..(36)
<223> OTHER INFORMATION: (-(CH2)3-)4
<220> FEATURE:
<221> NAME/KEY: misc_feature
<222> LOCATION: (47)..(49)
<223> OTHER INFORMATION: residues modified by phosphorothioate linkage
<220> FEATURE:
<221> NAME/KEY: misc_feature
<222> LOCATION: (50)..(50)
<223> OTHER INFORMATION: (-(CH2)3-)5-NH2

<400> SEQUENCE: 5
tccatgacgt tcctgatgct catttccctt aaatcgattt aagggaaatg        50

<210> SEQ ID NO 6
<211> LENGTH: 50
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: residues modified by phosphorothioate linkage
<220> FEATURE:
<221> NAME/KEY: misc_feature
<222> LOCATION: (20)..(21)
<223> OTHER INFORMATION: (-(CH2)3-)5
<220> FEATURE:
<221> NAME/KEY: misc_feature
<222> LOCATION: (21)..(23)
<223> OTHER INFORMATION: residues modified by phosphorothioate linkage
<220> FEATURE:
<221> NAME/KEY: misc_feature
<222> LOCATION: (35)..(36)
<223> OTHER INFORMATION: (-(CH2)3-)4
<220> FEATURE:
<221> NAME/KEY: misc_feature
<222> LOCATION: (47)..(49)
<223> OTHER INFORMATION: residues modified by phosphorothioate linkage
<220> FEATURE:
<221> NAME/KEY: misc_feature
<222> LOCATION: (50)..(50)
<223> OTHER INFORMATION: (-(CH2)3-)5-NH2

<400> SEQUENCE: 6
tccatgacgt tcctgatgct actcttgcca attacgtaat tggcaagagt        50

<210> SEQ ID NO 7
<211> LENGTH: 30
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: OH-(-(CH2)3-)5
<220> FEATURE:
<221> NAME/KEY: misc_feature
<222> LOCATION: (1)..(3)
<223> OTHER INFORMATION: residues modified by phosphorothioate linkage
```

```
<220> FEATURE:
<221> NAME/KEY: misc_feature
<222> LOCATION: (15)..(16)
<223> OTHER INFORMATION: (-(CH2)3-)4
<220> FEATURE:
<221> NAME/KEY: misc_feature
<222> LOCATION: (27)..(29)
<223> OTHER INFORMATION: residues modified by phosphorothioate linkage
<220> FEATURE:
<221> NAME/KEY: misc_feature
<222> LOCATION: (30)..(30)
<223> OTHER INFORMATION: (-(CH2)3-)5-NH2

<400> SEQUENCE: 7
catttcccgt aaatcgattt acgggaaatg                                           30

<210> SEQ ID NO 8
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: residues modified by phosphorothioate linkage
<220> FEATURE:
<221> NAME/KEY: misc_feature
<222> LOCATION: (15)..(19)
<223> OTHER INFORMATION: residues modified by phosphorothioate linkage

<400> SEQUENCE: 8
ggggtcaacg ttgagggggg                                                      20

<210> SEQ ID NO 9
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: residue modified by phosphorothioate linkage
<220> FEATURE:
<221> NAME/KEY: misc_feature
<222> LOCATION: (15)..(19)
<223> OTHER INFORMATION: residues modified by phosphorothioate linkage

<400> SEQUENCE: 9
ggggtcaacg ttgagggggg                                                      20

<210> SEQ ID NO 10
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: residues modified by phosphorothioate linkage
<220> FEATURE:
<221> NAME/KEY: misc_feature
<222> LOCATION: (15)..(19)
<223> OTHER INFORMATION: residues modified by phosphorothioate linkage

<400> SEQUENCE: 10
gggggacgat cgtcggggggg                                                     20
```

```
<210> SEQ ID NO 11
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: residue modified by phosphorothioate linkage
<220> FEATURE:
<221> NAME/KEY: misc_feature
<222> LOCATION: (15)..(19)
<223> OTHER INFORMATION: residues modified by phosphorothioate linkage

<400> SEQUENCE: 11
gggggacgat cgtcggggggg                                              20

<210> SEQ ID NO 12
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: residues modified by phosphorothioate linkage
<220> FEATURE:
<221> NAME/KEY: misc_feature
<222> LOCATION: (16)..(19)
<223> OTHER INFORMATION: residues modified by phosphorothioate linkage

<400> SEQUENCE: 12
ggtgcatcga tgcagggggg                                              20

<210> SEQ ID NO 13
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: residue modified by phosphorothioate linkage
<220> FEATURE:
<221> NAME/KEY: misc_feature
<222> LOCATION: (16)..(19)
<223> OTHER INFORMATION: residues modified by phosphorothioate linkage

<400> SEQUENCE: 13
ggtgcatcga tgcagggggg                                              20

<210> SEQ ID NO 14
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: residues modified by phosphorothioate linkage
<220> FEATURE:
<221> NAME/KEY: misc_feature
<222> LOCATION: (16)..(20)
<223> OTHER INFORMATION: residues modified by phosphorothioate linkage

<400> SEQUENCE: 14
ggggacgacg tcgtggggggg g                                           21
```

```
<210> SEQ ID NO 15
<211> LENGTH: 21
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(2)
<223> OTHER INFORMATION: residues modified by phosphorothioate linkage
<220> FEATURE:
<221> NAME/KEY: misc_feature
<222> LOCATION: (16)..(20)
<223> OTHER INFORMATION: residues modified by phosphorothioate linkage

<400> SEQUENCE: 15
ggggacgacg tcgtgggggg g                                              21

<210> SEQ ID NO 16
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: residues modified by phosphorothioate linkage

<400> SEQUENCE: 16
tccatgacgt tcctgatgct                                                20

<210> SEQ ID NO 17
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(19)
<223> OTHER INFORMATION: residues modified by phosphorothioate linkage

<400> SEQUENCE: 17
tccatgacgt tcctgacgtt                                                20

<210> SEQ ID NO 18
<211> LENGTH: 24
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(23)
<223> OTHER INFORMATION: residues modified by phosphorothioate linkage

<400> SEQUENCE: 18
tcgtcgtttt gtcgttttgt cgtt                                           24

<210> SEQ ID NO 19
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(21)
<223> OTHER INFORMATION: residues modified by phosphorothioate linkage
```

```
<400> SEQUENCE: 19
tcgtcgttgt cgttttgtcg tt                                          22

<210> SEQ ID NO 20
<211> LENGTH: 22
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(21)
<223> OTHER INFORMATION: residues modified by phosphorothioate linkage

<400> SEQUENCE: 20
tcgtcgtttt cggcgcgcgc cg                                          22

<210> SEQ ID NO 21
<211> LENGTH: 25
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<222> LOCATION: (1)..(24)
<223> OTHER INFORMATION: residues modified by phosphorothioate linkage

<400> SEQUENCE: 21
tcgtcgtcgt tcgaacgacg ttgat                                       25
```